(12) United States Patent
Matsunobu et al.

(10) Patent No.: US 10,908,430 B2
(45) Date of Patent: Feb. 2, 2021

(54) MEDICAL IMAGING SYSTEM, ILLUMINATION DEVICE, AND METHOD

(71) Applicant: SONY CORPORATION, Tokyo (JP)

(72) Inventors: Goh Matsunobu, Tokyo (JP); Takashi Yamaguchi, Kanagawa (JP); Akio Furukawa, Tokyo (JP)

(73) Assignee: Sony Corporation, Tokyo (JP)

( * ) Notice: Subject to any disclaimer, the term of this patent is extended or adjusted under 35 U.S.C. 154(b) by 652 days.

(21) Appl. No.: 15/534,300

(22) PCT Filed: Dec. 15, 2015

(86) PCT No.: PCT/JP2015/006261
§ 371 (c)(1),
(2) Date: Jun. 8, 2017

(87) PCT Pub. No.: WO2016/103643
PCT Pub. Date: Jun. 30, 2016

(65) Prior Publication Data
US 2017/0343792 A1  Nov. 30, 2017

(30) Foreign Application Priority Data

Dec. 25, 2014  (JP) ................................ 2014-262323
Dec. 25, 2014  (JP) ................................ 2014-262325

(51) Int. Cl.
*A61B 6/00* (2006.01)
*G02B 27/10* (2006.01)
(Continued)

(52) U.S. Cl.
CPC ........ *G02B 27/1006* (2013.01); *A61B 5/0071* (2013.01); *A61B 5/0084* (2013.01);
(Continued)

(58) Field of Classification Search
None
See application file for complete search history.

(56) References Cited

U.S. PATENT DOCUMENTS 5,600,487 A * 2/1997 Kiyomoto ............ G02B 5/0833
                                                         359/634
5,801,808 A * 9/1998 Abraham ................. A61B 3/12
                                                         351/221
(Continued)

FOREIGN PATENT DOCUMENTS

CN     102448225 A     5/2012
EP        2436301 A1   4/2012
(Continued)

OTHER PUBLICATIONS

Office Action for JP Patent Application No. 2018-158856, dated Jul. 30, 2019, 08 pages of Office Action and 08 pages of English Translation.
(Continued)

*Primary Examiner* — Joel F Brutus
(74) *Attorney, Agent, or Firm* — Chip Law Group

(57) ABSTRACT

According to some aspects, a medical imaging system is provided. The medical imaging system includes an illumination device and a medical imaging device. The illumination device includes a first light source configured to emit first light having a wavelength range. The illumination device further includes a second light source configured to emit second light having at least one predetermined wavelength band. The at least one predetermined wavelength band is within the wavelength range. The illumination device further includes a dichroic mirror configured to attenuate a portion of the wavelength range corresponding to the at least one predetermined wavelength band and to multiplex the second light with the first light such that the portion of the wavelength range of the first light is attenu-
(Continued)

ated. The light multiplexed by the dichroic mirror is emitted from the illumination device along an optical axis and irradiates an observation site. The medical imaging device includes at least one sensor configured to receive light from the observation site.

24 Claims, 24 Drawing Sheets

(51) Int. Cl.
*A61N 5/06* (2006.01)
*A61B 5/00* (2006.01)
*G02B 27/48* (2006.01)
*G02B 27/14* (2006.01)
*G02B 19/00* (2006.01)
*A61B 1/04* (2006.01)
*A61B 1/06* (2006.01)
*A61B 1/07* (2006.01)
*A61B 1/00* (2006.01)
*G02B 23/24* (2006.01)

(52) U.S. Cl.
CPC ........... *A61N 5/062* (2013.01); *A61N 5/0603* (2013.01); *G02B 19/0047* (2013.01); *G02B 27/141* (2013.01); *G02B 27/48* (2013.01); *A61B 1/00163* (2013.01); *A61B 1/00167* (2013.01); *A61B 1/042* (2013.01); *A61B 1/043* (2013.01); *A61B 1/0638* (2013.01); *A61B 1/0661* (2013.01); *A61B 1/0669* (2013.01); *A61B 1/07* (2013.01); *G02B 23/2461* (2013.01); *G02B 23/2469* (2013.01)

(56) References Cited

U.S. PATENT DOCUMENTS

| | | | | |
|---|---|---|---|---|
| 6,464,633 | B1* | 10/2002 | Hosoda | A61B 1/0638 348/68 |
| 2001/0028441 | A1* | 10/2001 | Okamoto | A61B 3/132 351/214 |
| 2002/0062061 | A1* | 5/2002 | Kaneko | A61B 1/00009 600/118 |
| 2002/0120181 | A1 | 8/2002 | Irion | |
| 2002/0126894 | A1* | 9/2002 | Segawa | G06K 7/12 382/176 |
| 2009/0236541 | A1* | 9/2009 | Lomnes | A61B 1/043 250/458.1 |
| 2011/0063578 | A1* | 3/2011 | Inoue | G02B 27/0927 353/20 |
| 2011/0292343 | A1* | 12/2011 | Papac | A61B 3/0008 351/221 |
| 2012/0081532 | A1 | 4/2012 | Kumai | |
| 2012/0140183 | A1* | 6/2012 | Tanaka | G03B 21/28 353/20 |
| 2014/0121468 | A1* | 5/2014 | Eichenholz | A61B 1/0646 600/249 |

FOREIGN PATENT DOCUMENTS

| | | |
|---|---|---|
| JP | 10-286235 A | 10/1998 |
| JP | 2001-264697 A | 9/2001 |
| JP | 2002-136468 A | 5/2002 |
| JP | 2005-342033 A | 12/2005 |
| JP | 2005-342034 A | 12/2005 |
| JP | 2006-000157 A | 1/2006 |
| JP | 2006-337609 A | 12/2006 |
| JP | 2009-131496 A | 6/2009 |
| JP | 2011-010998 A | 1/2011 |
| JP | 2012-078504 A | 4/2012 |
| JP | 2012-081133 A | 4/2012 |
| JP | 2012-157383 A | 8/2012 |
| JP | 2013-090706 A | 5/2013 |
| JP | 2013-255655 A | 12/2013 |
| WO | 2014/152757 A2 | 9/2014 |

OTHER PUBLICATIONS

Office Action for JP Patent Application No. 2014-262323, dated Jan. 9, 2018, 06 pages of Office Action and 04 pages of English Translation.
Office Action for JP Patent Application No. 2014-262325, dated Jan. 9, 2018, 07 pages of Office Action and 05 pages of English Translation.
International Search Report and Written Opinion of PCT Application No. PCT/JP2015/006261, dated Apr. 4, 2016, 11 pages.
Office Action for EP Patent Application No. 15820300.0, dated Jul. 3, 2019, 05 pages of Office Action.
Office Action for JP Patent Application No. 2018-158635, dated Jul. 30, 2019, 07 pages of Office Action and 05 pages of English Translation.

* cited by examiner

[Fig. 1]
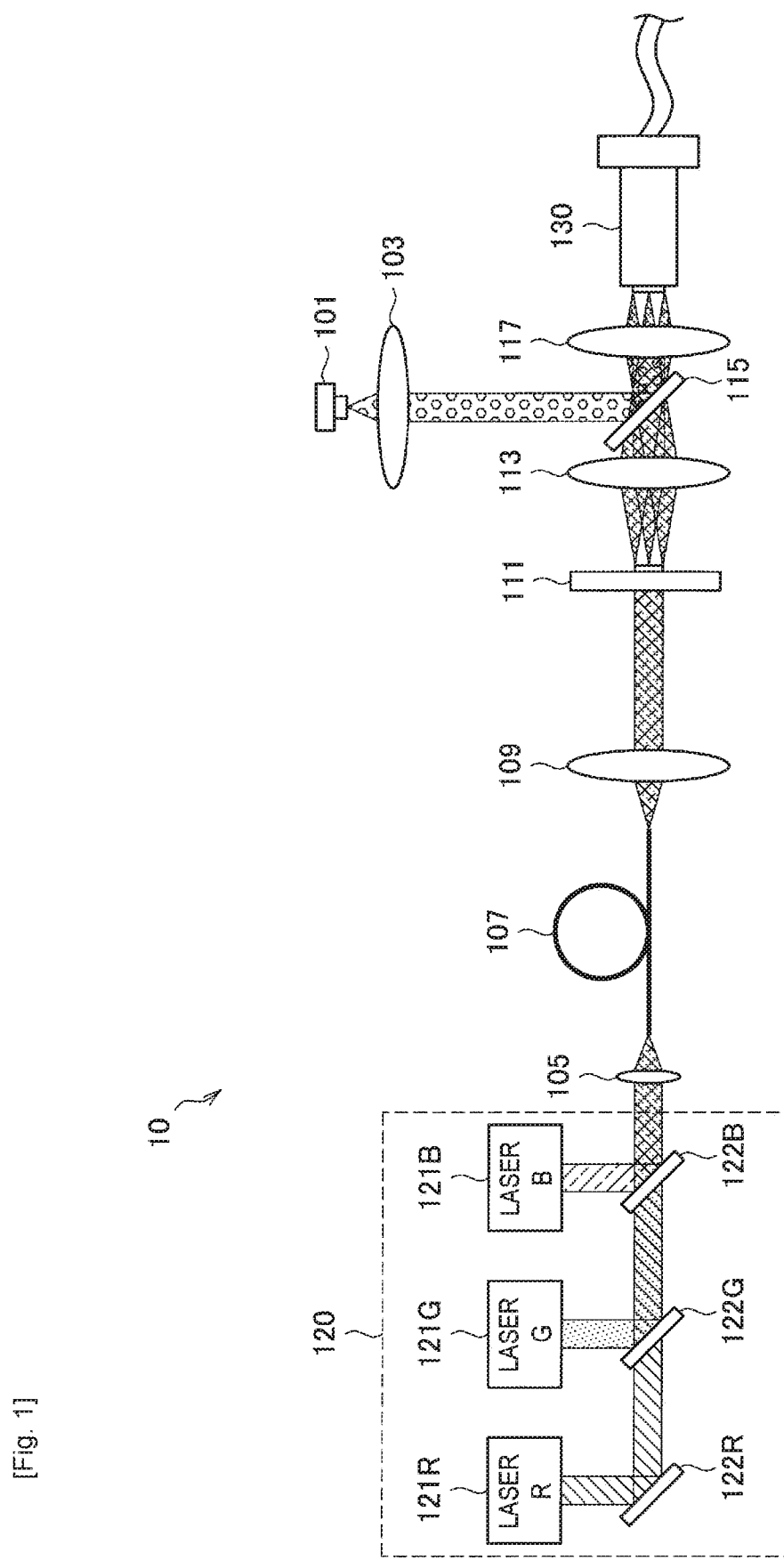

[Fig. 2]
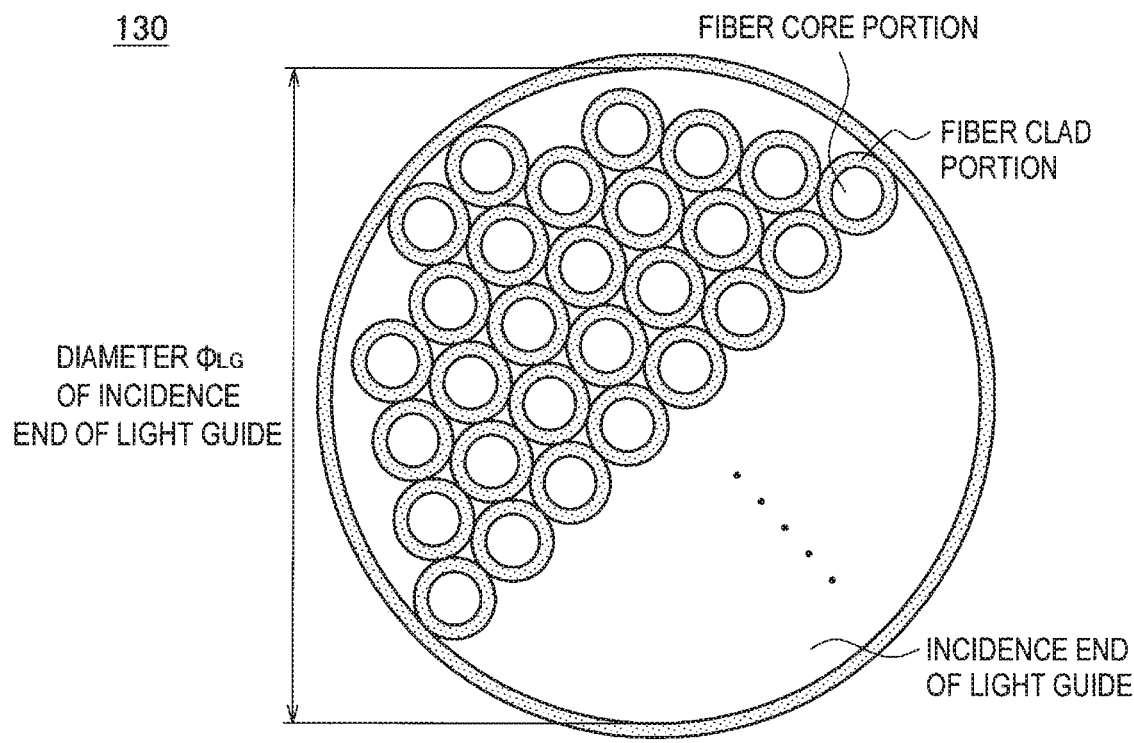

[Fig. 4]
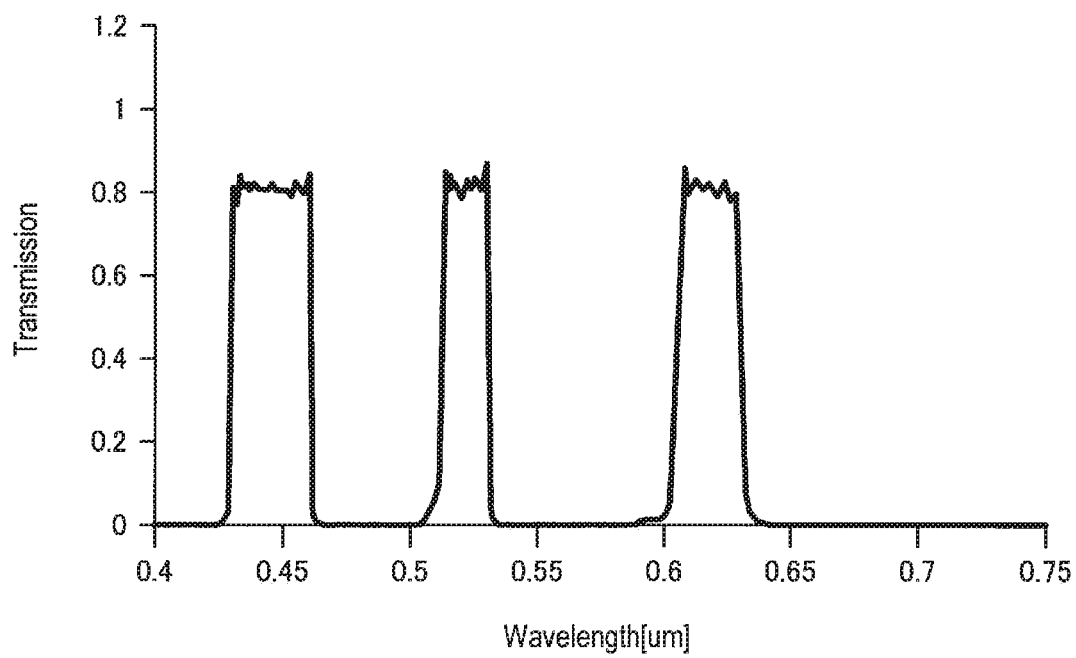
[Fig. 5]
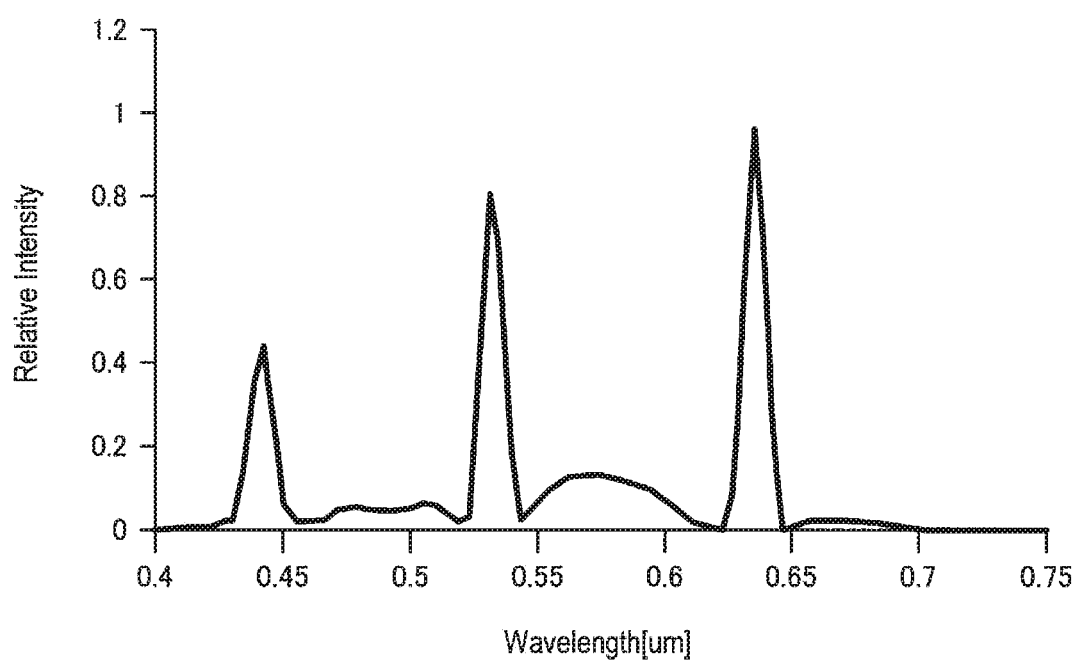

[Fig. 7]
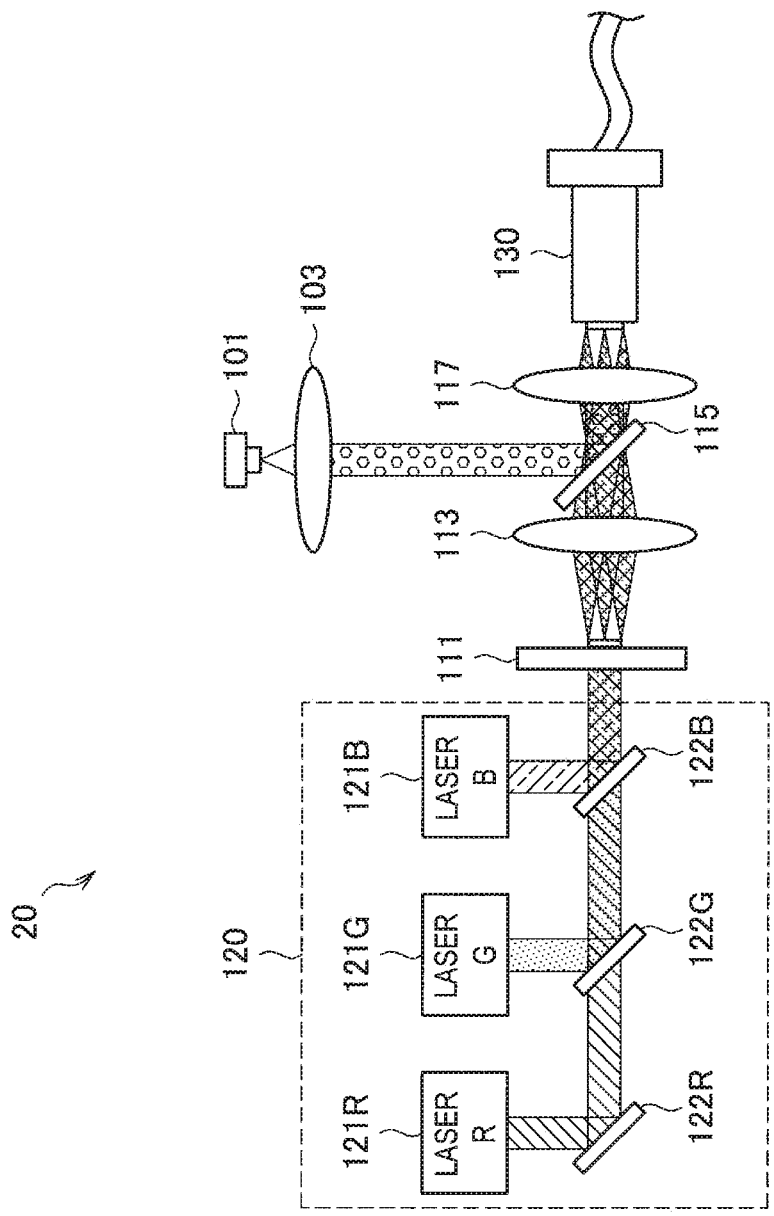

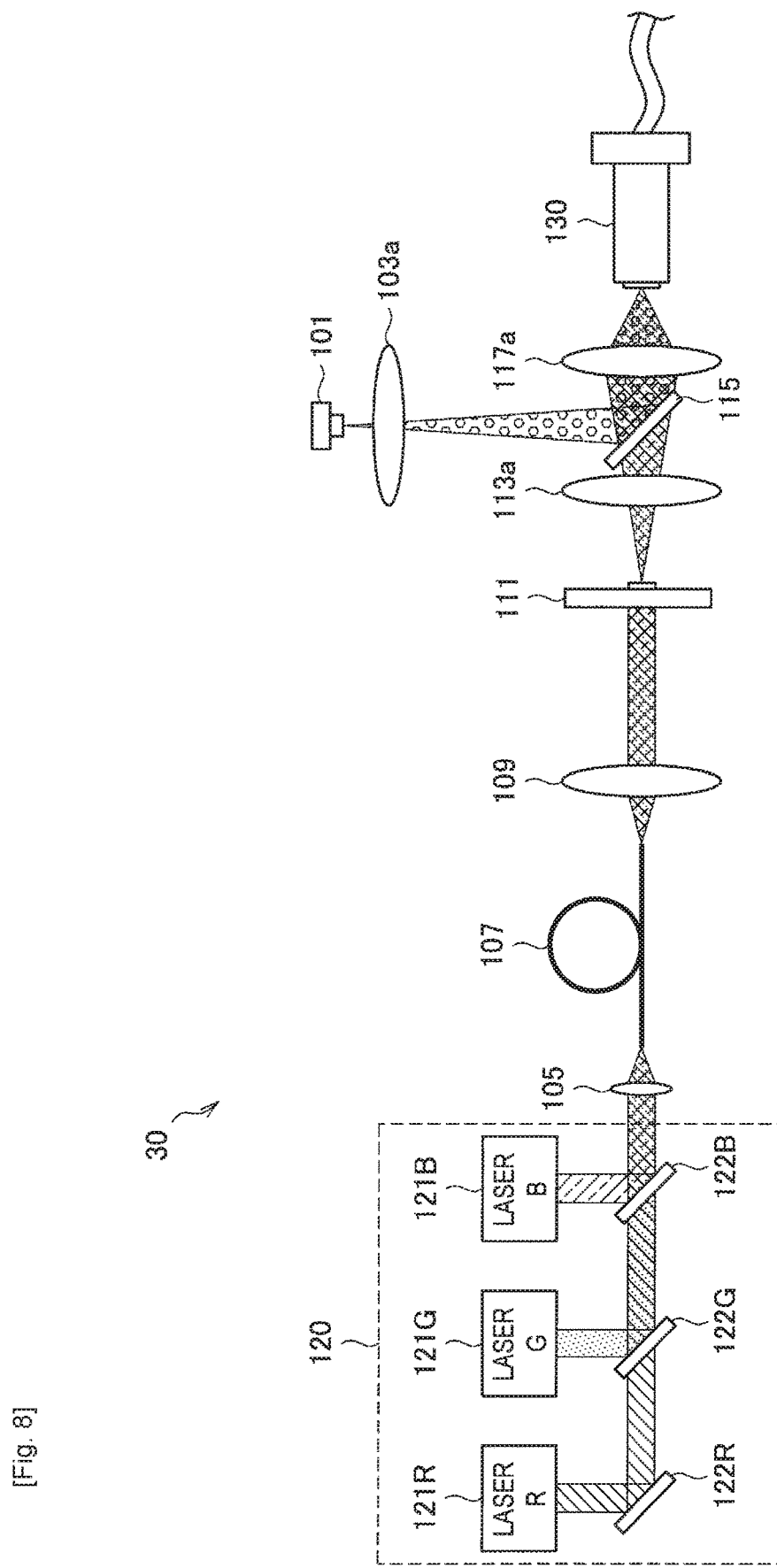
[Fig. 8]

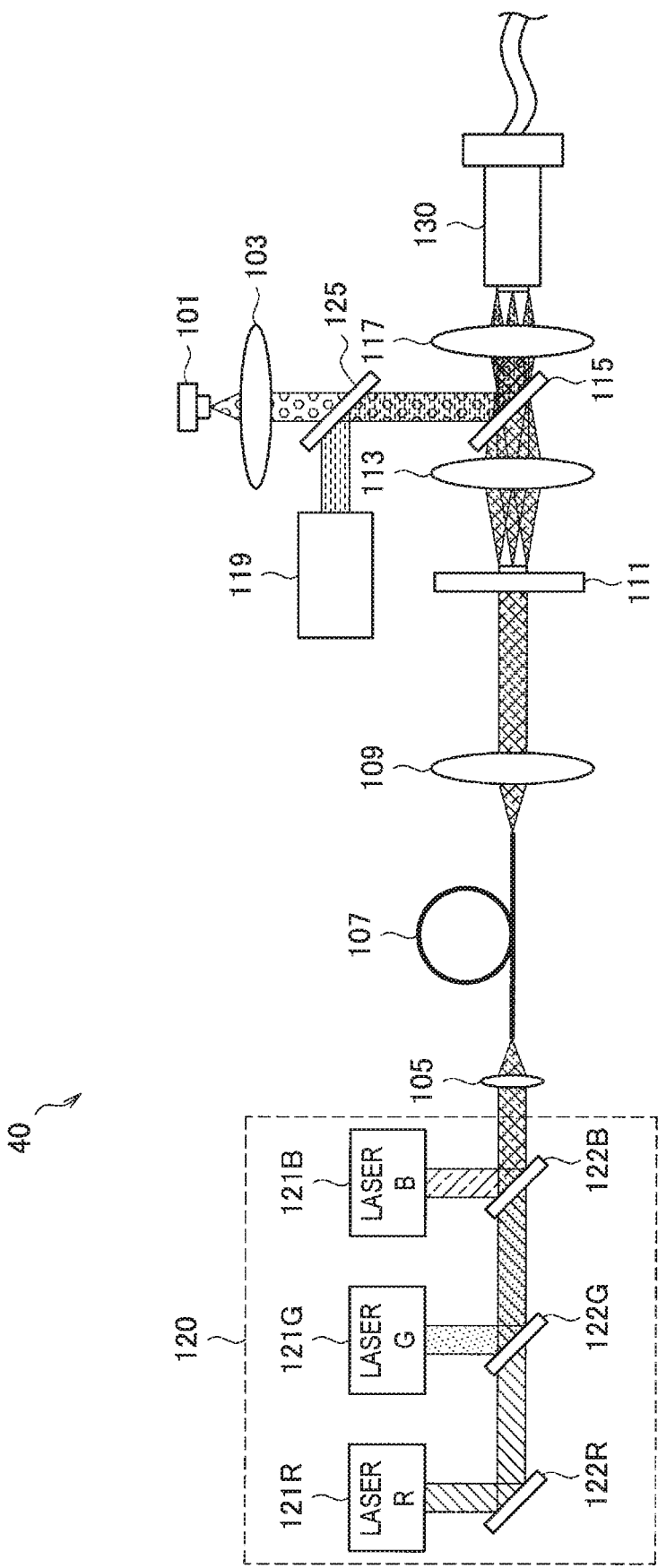
[Fig. 9]

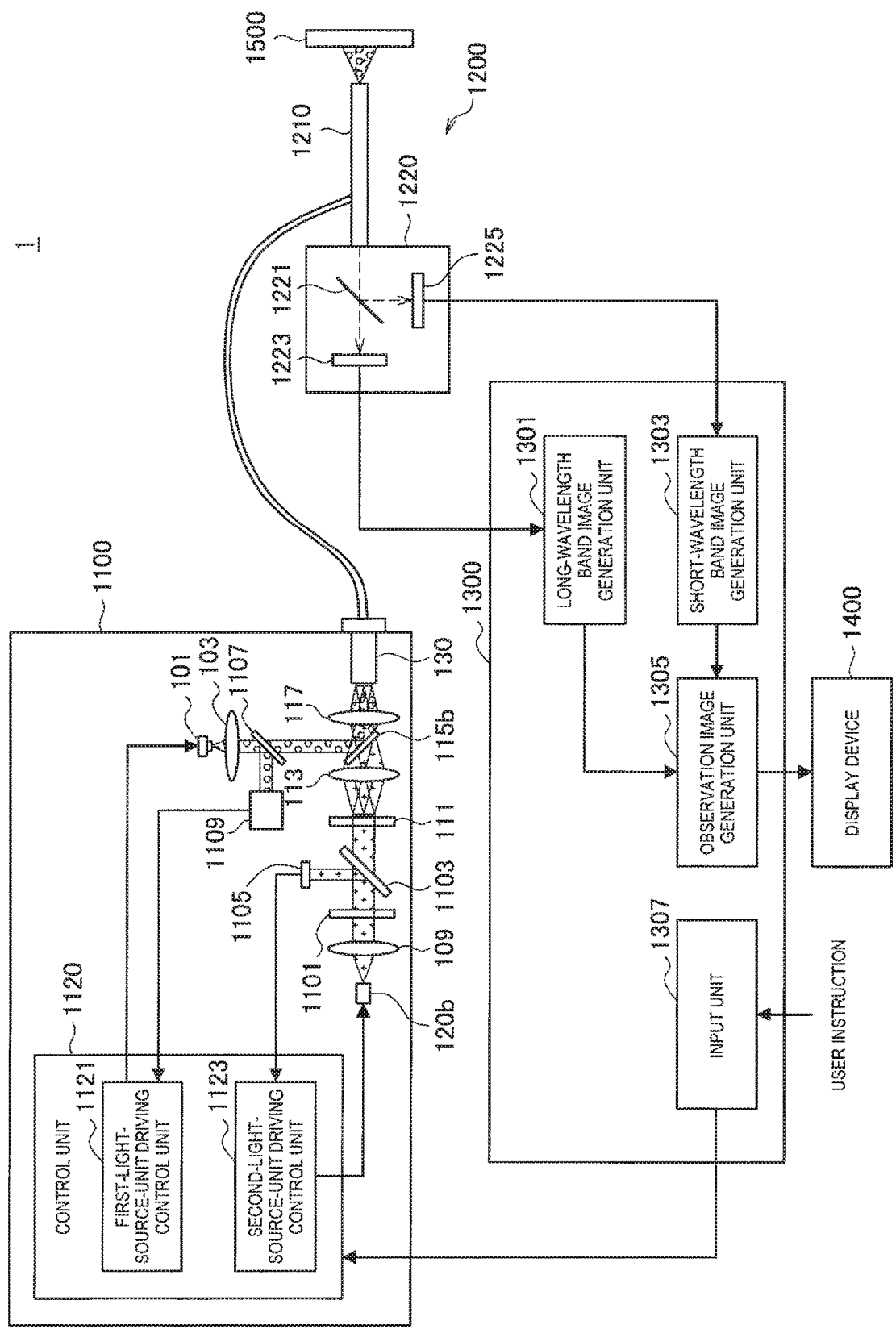
[Fig. 10]

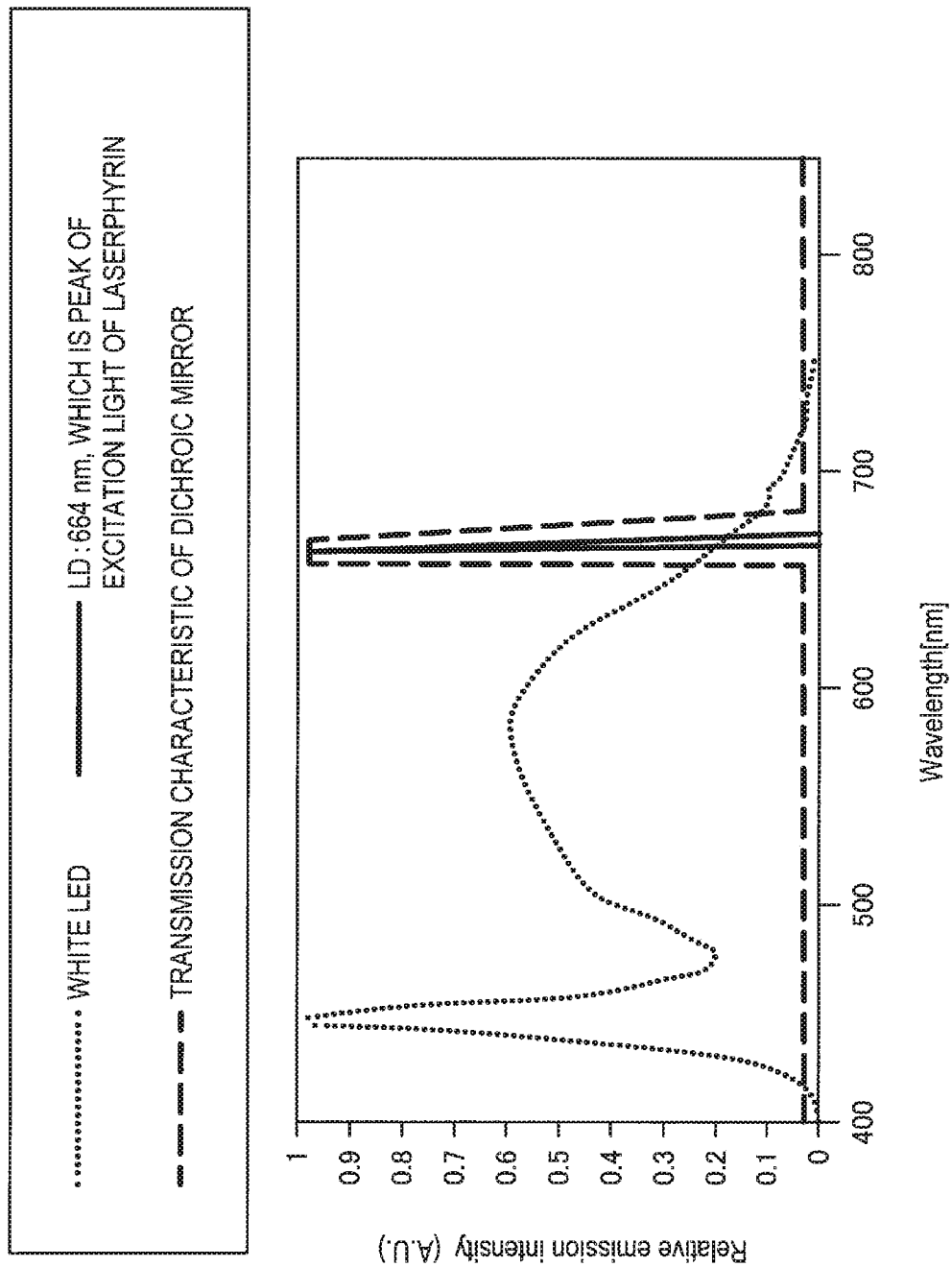
[Fig. 11]

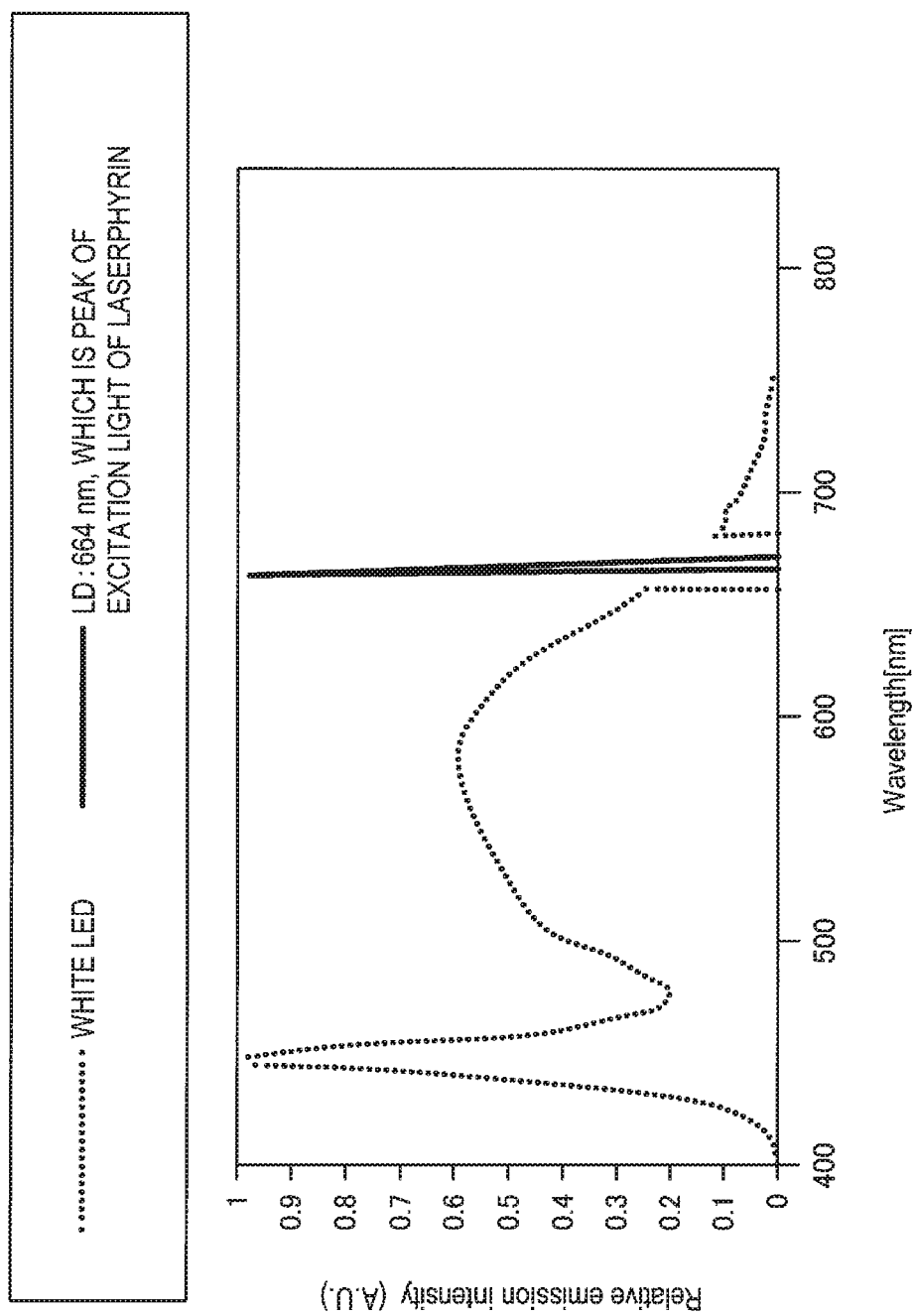
[Fig. 12]

[Fig. 13]
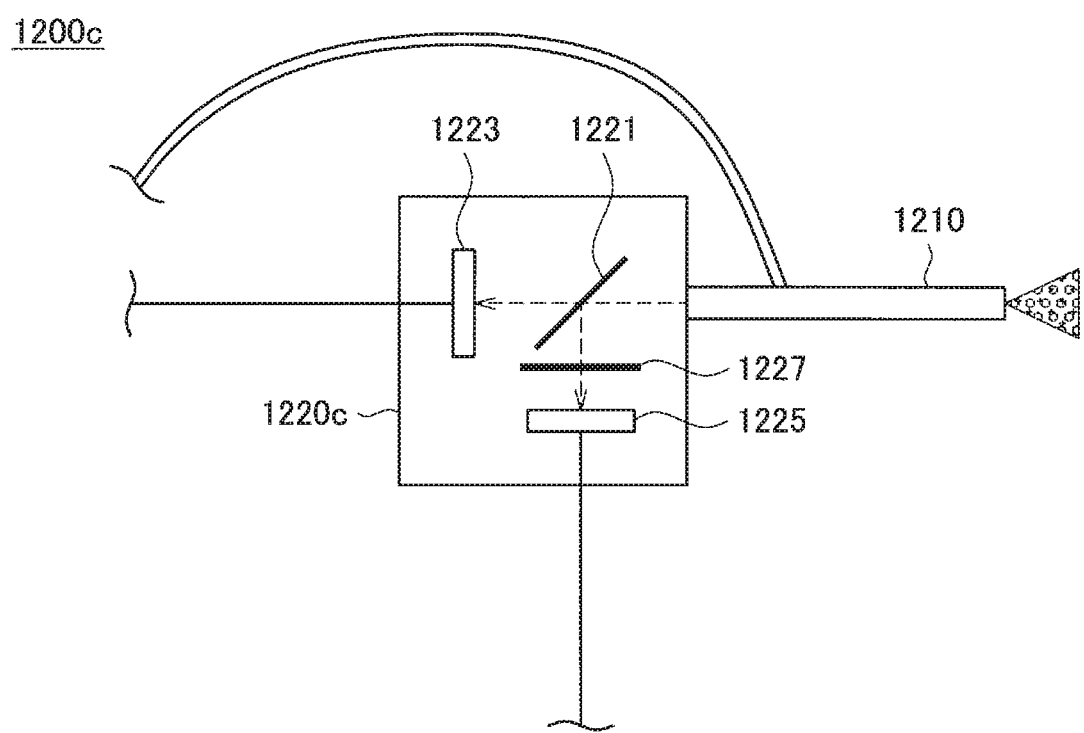

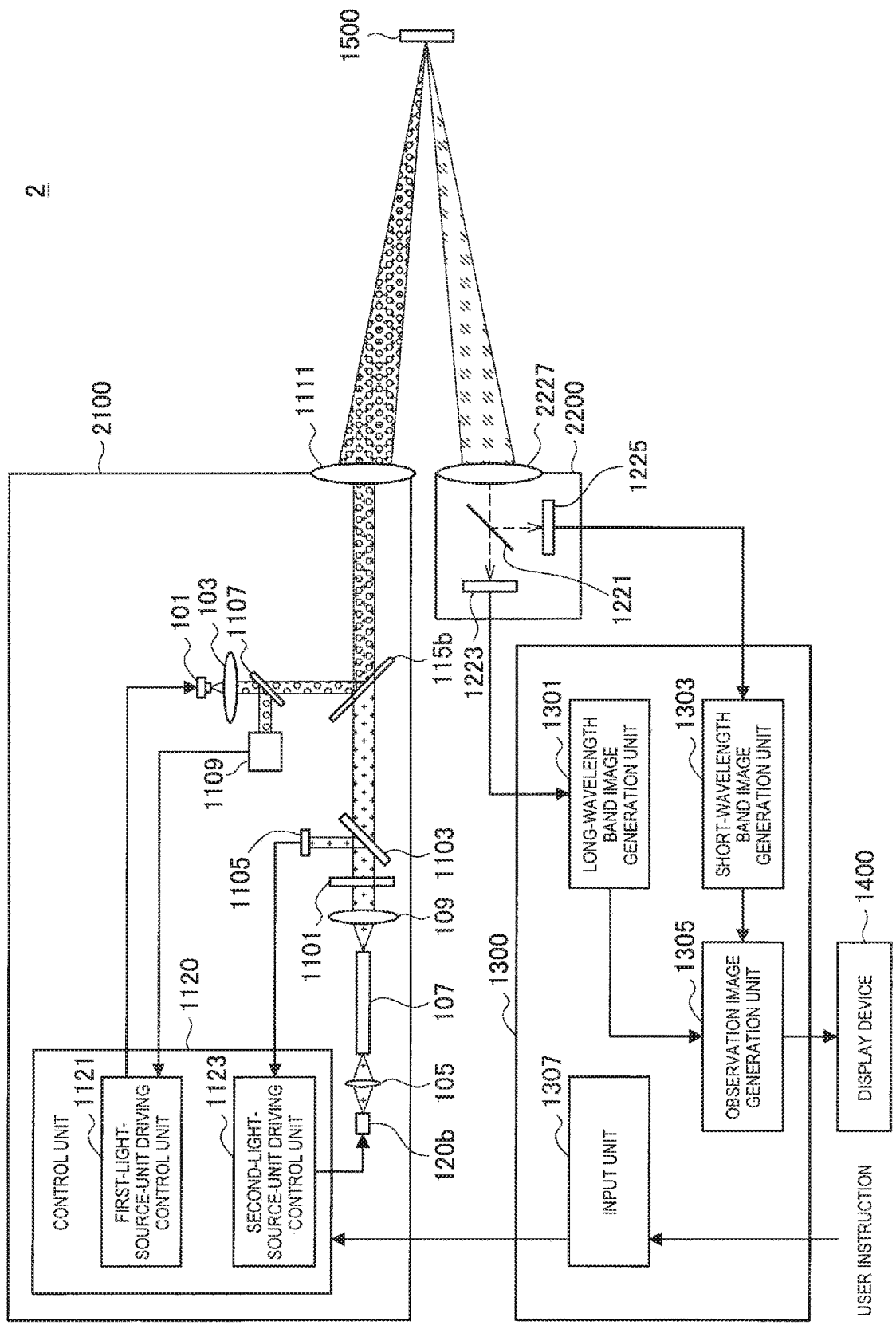

[Fig. 15]
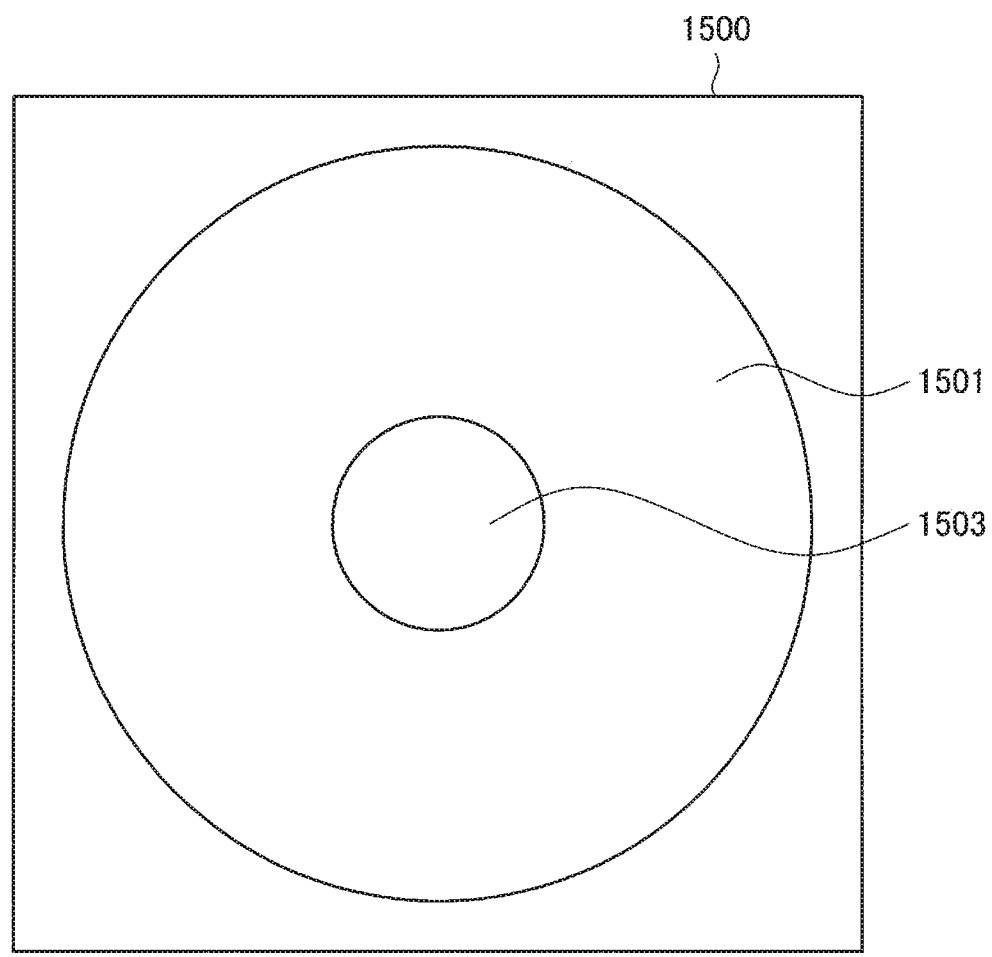

[Fig. 16]
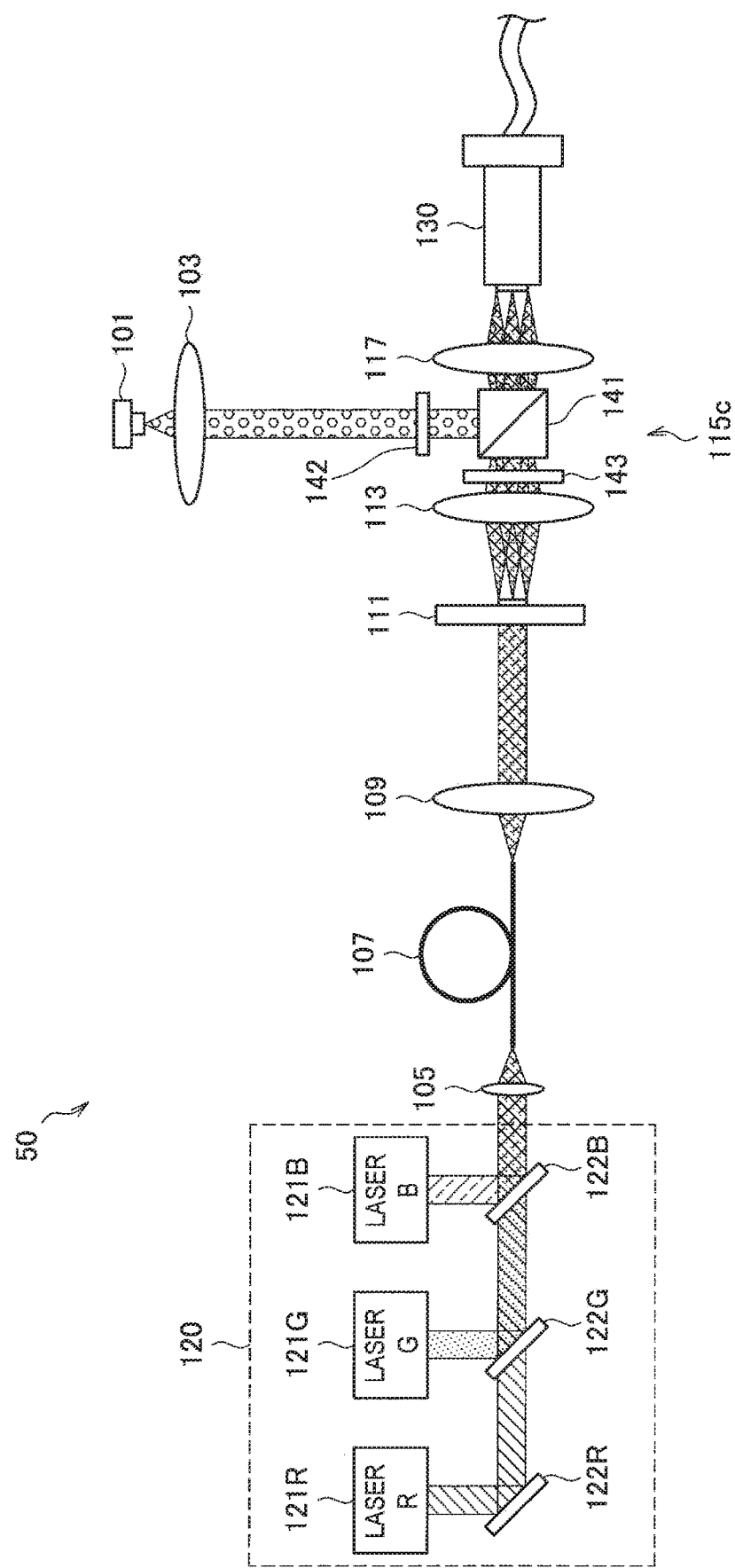

[Fig. 17]
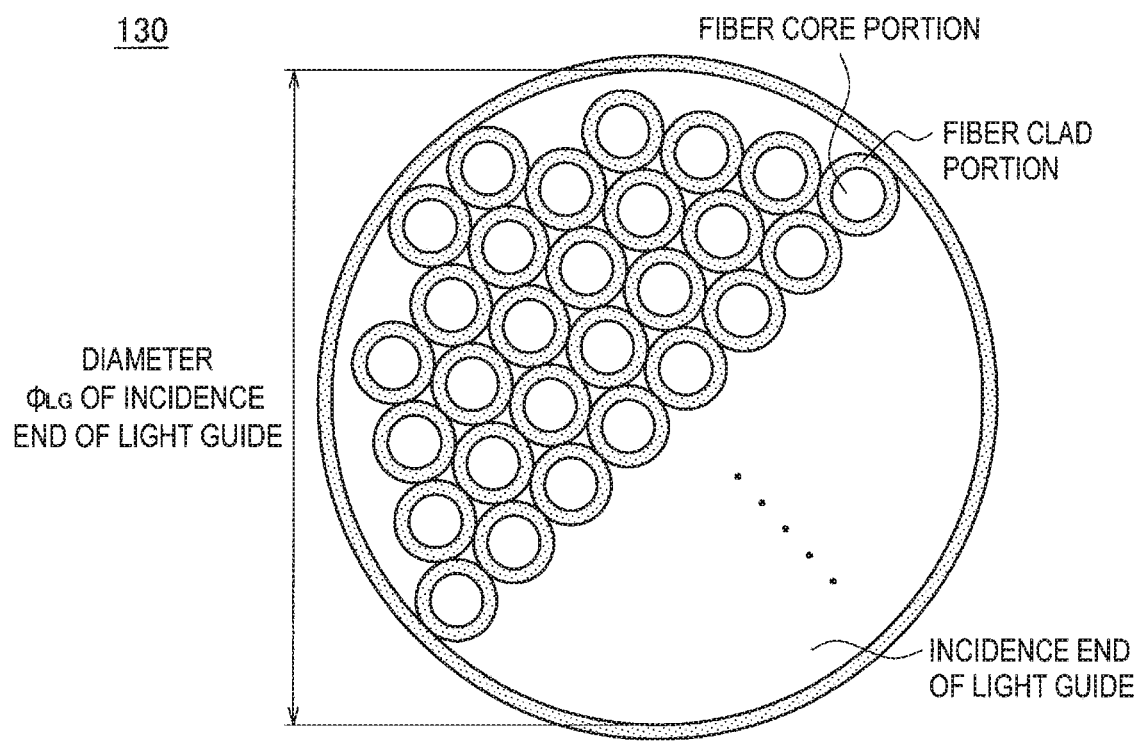
[Fig. 18]
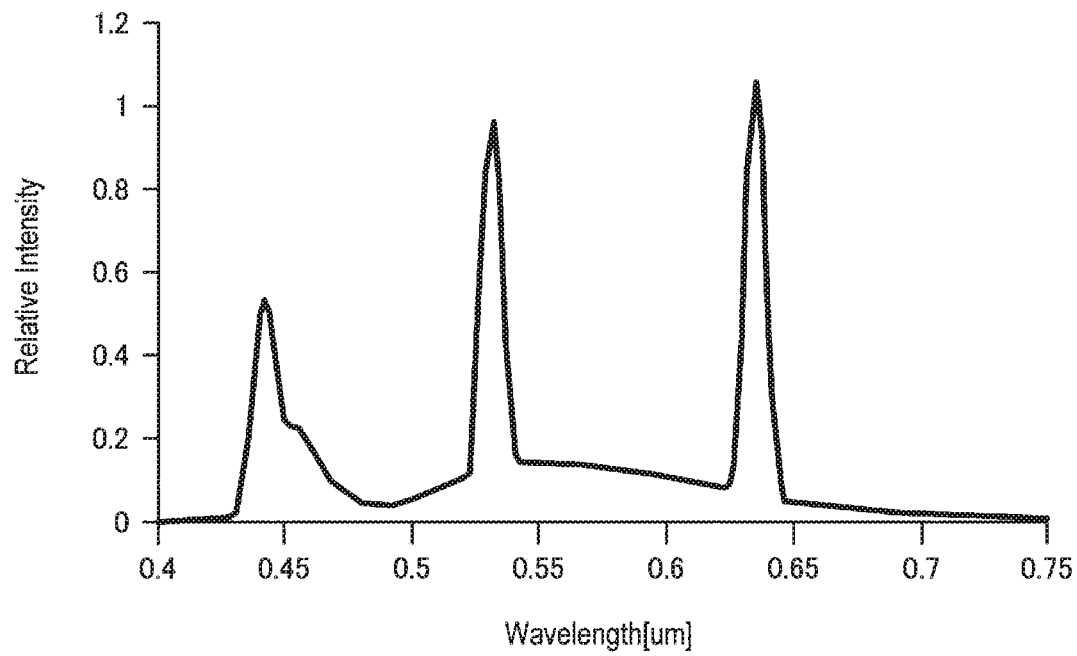

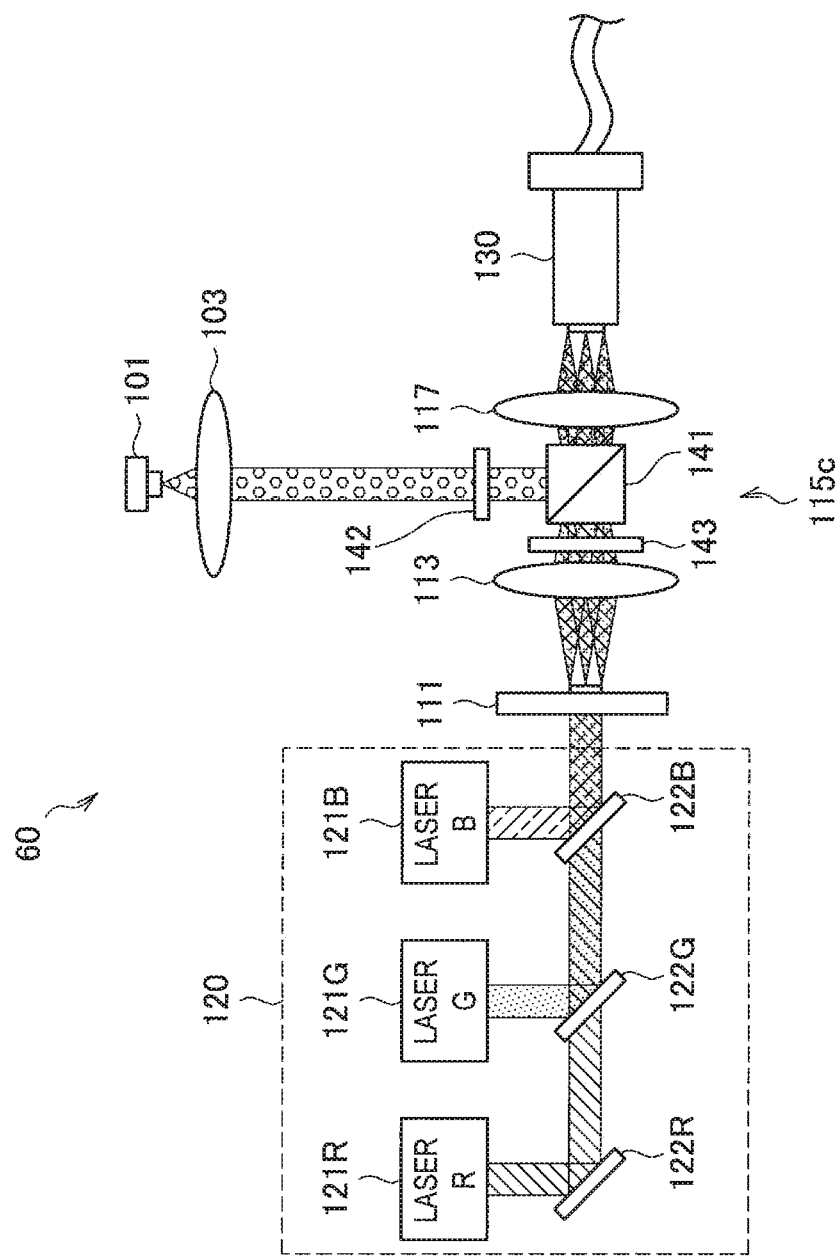
[Fig. 19]

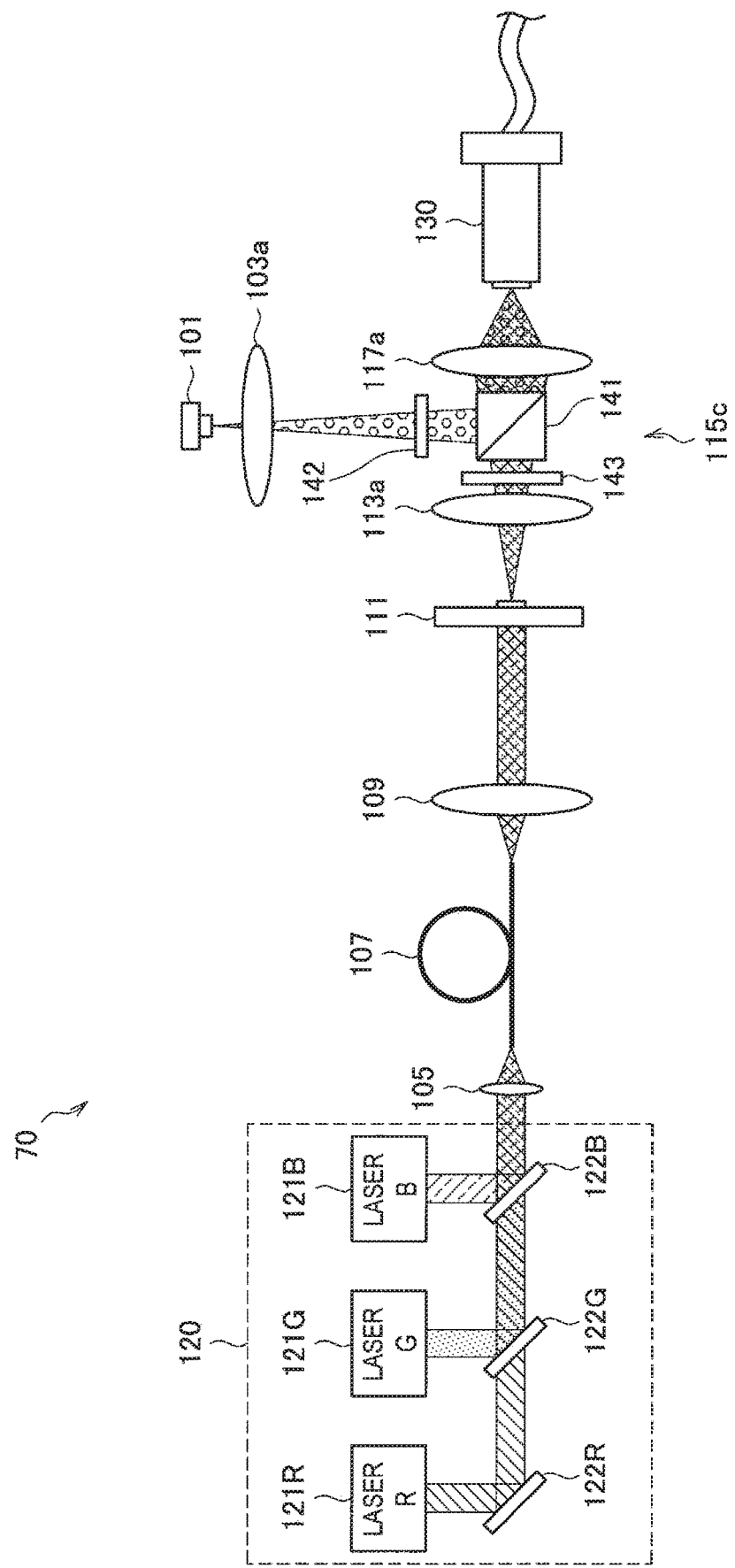

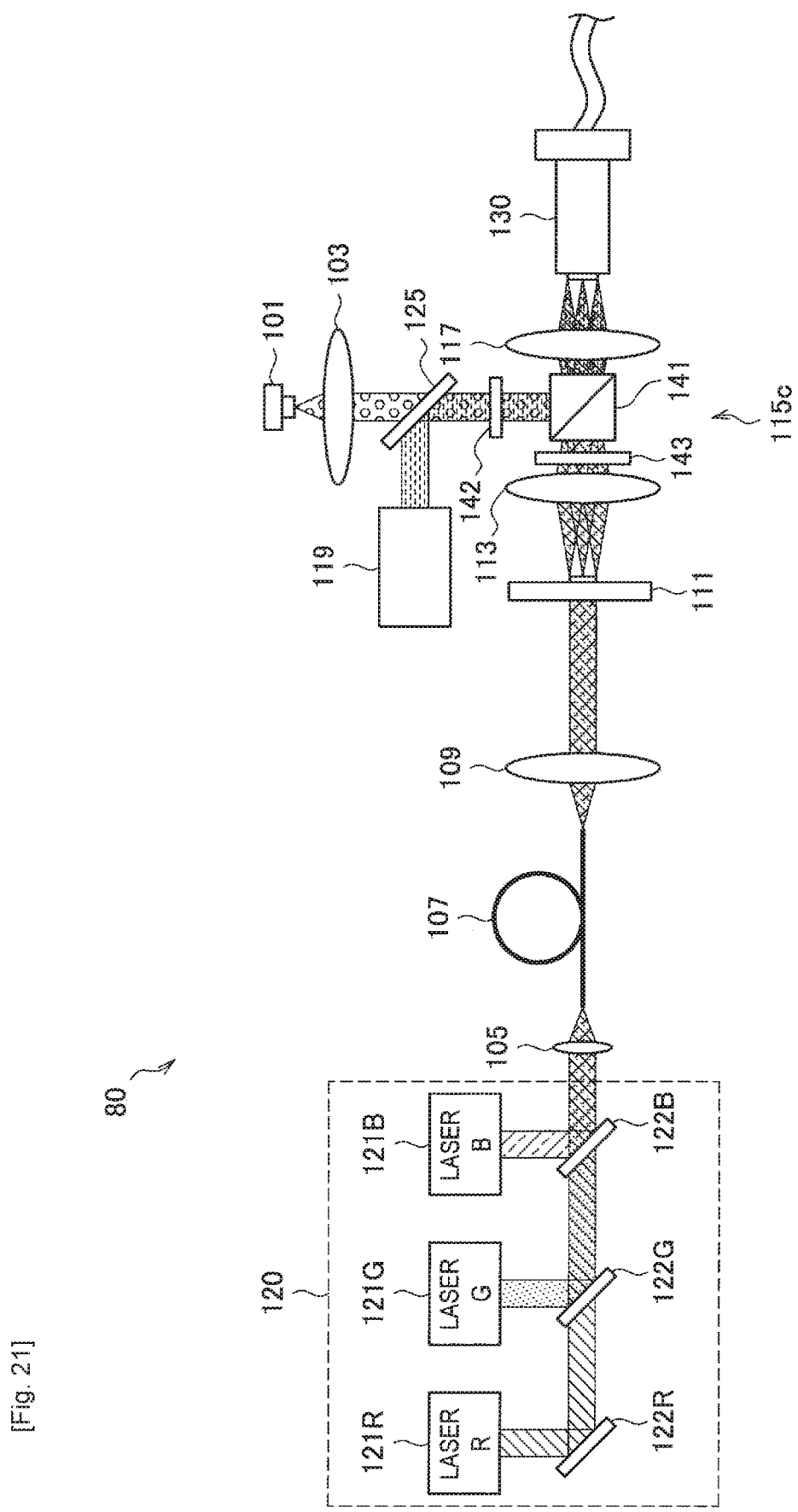
[Fig. 21]

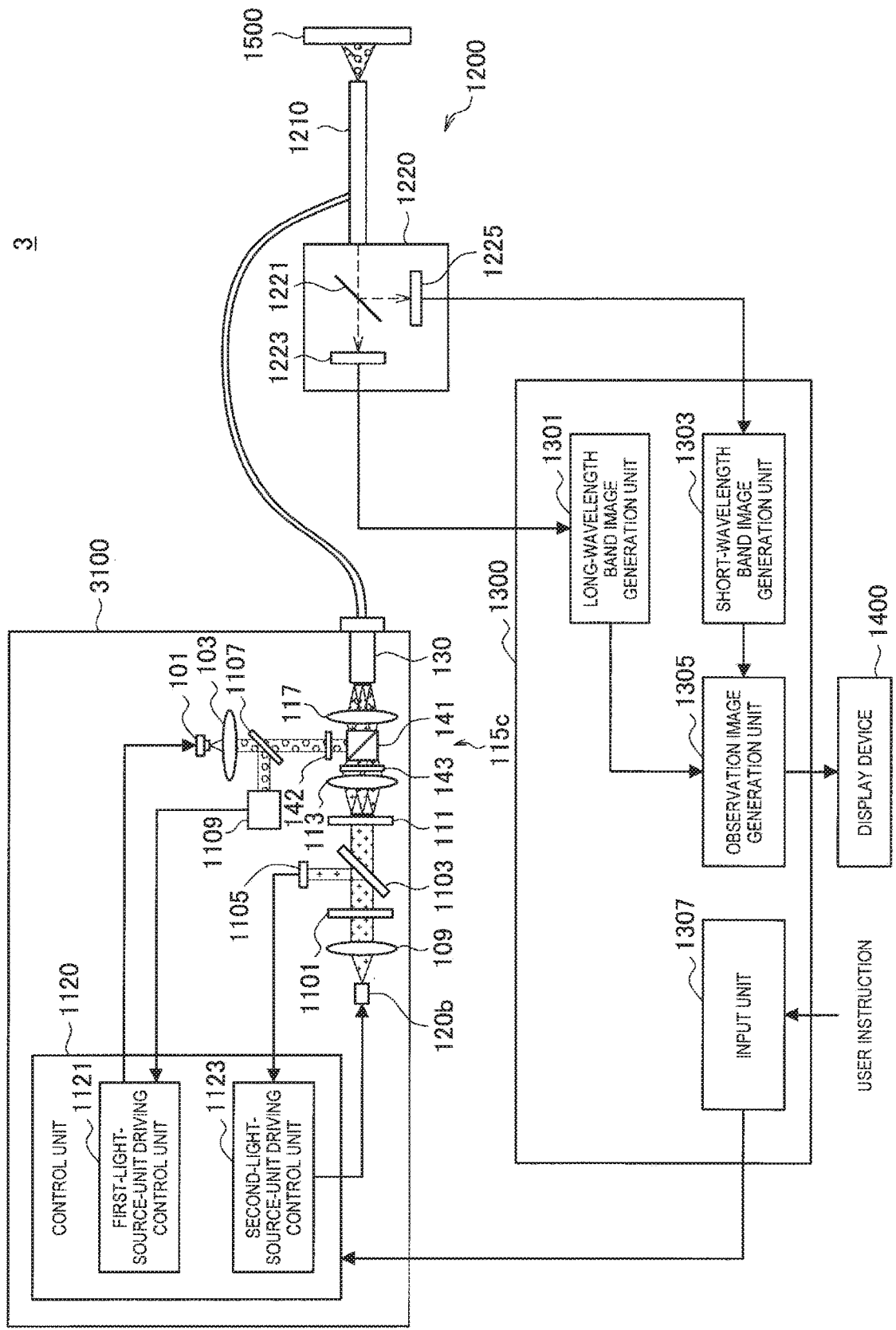
[Fig. 22]

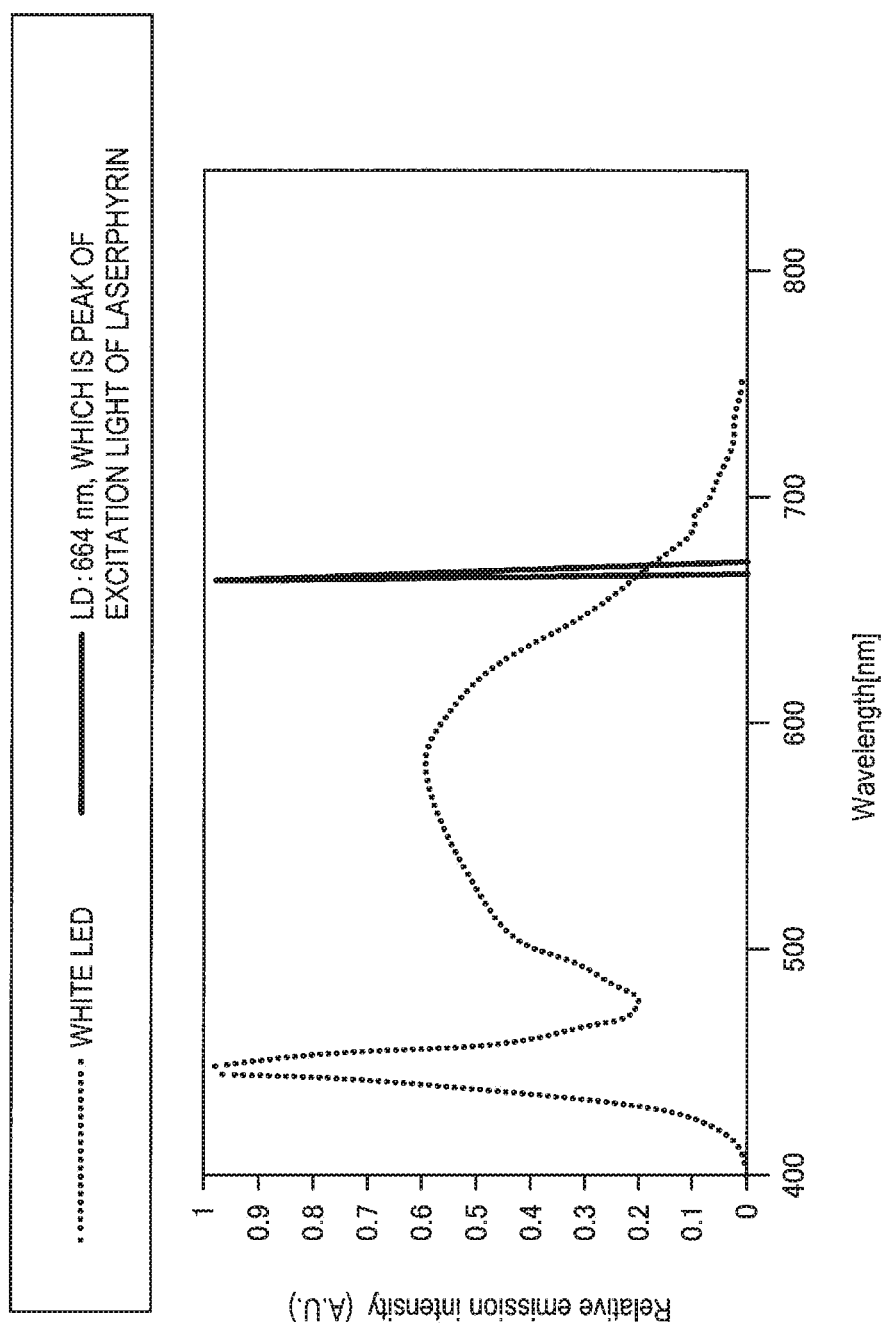
[Fig. 23]

[Fig. 24]
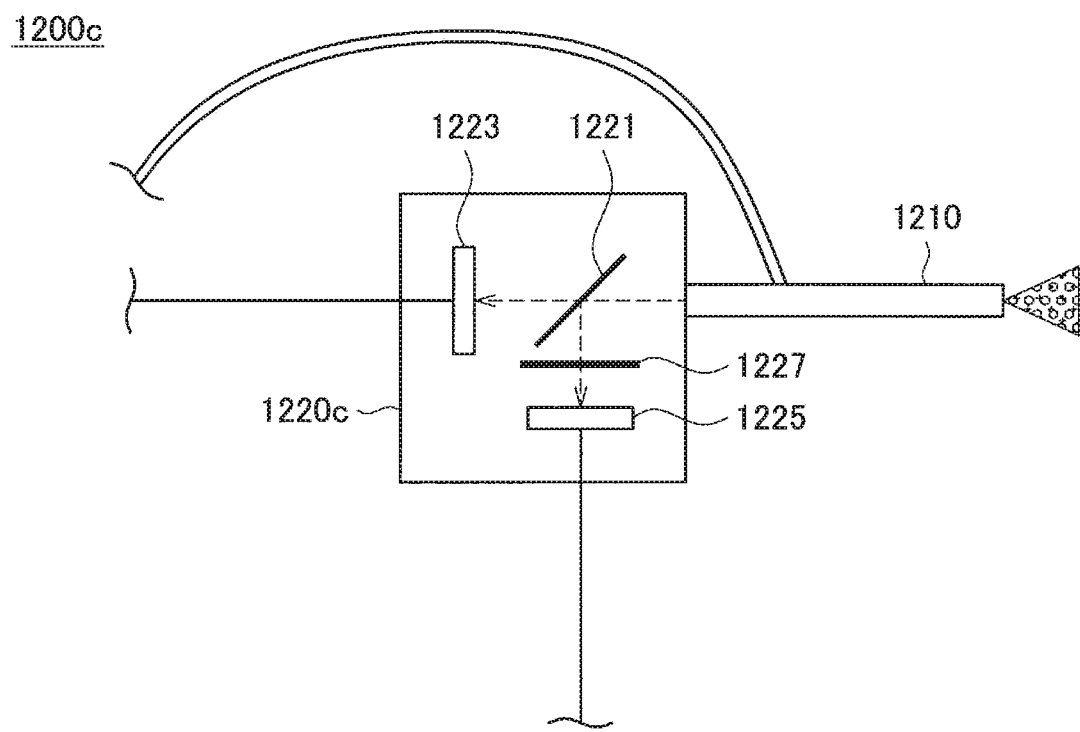

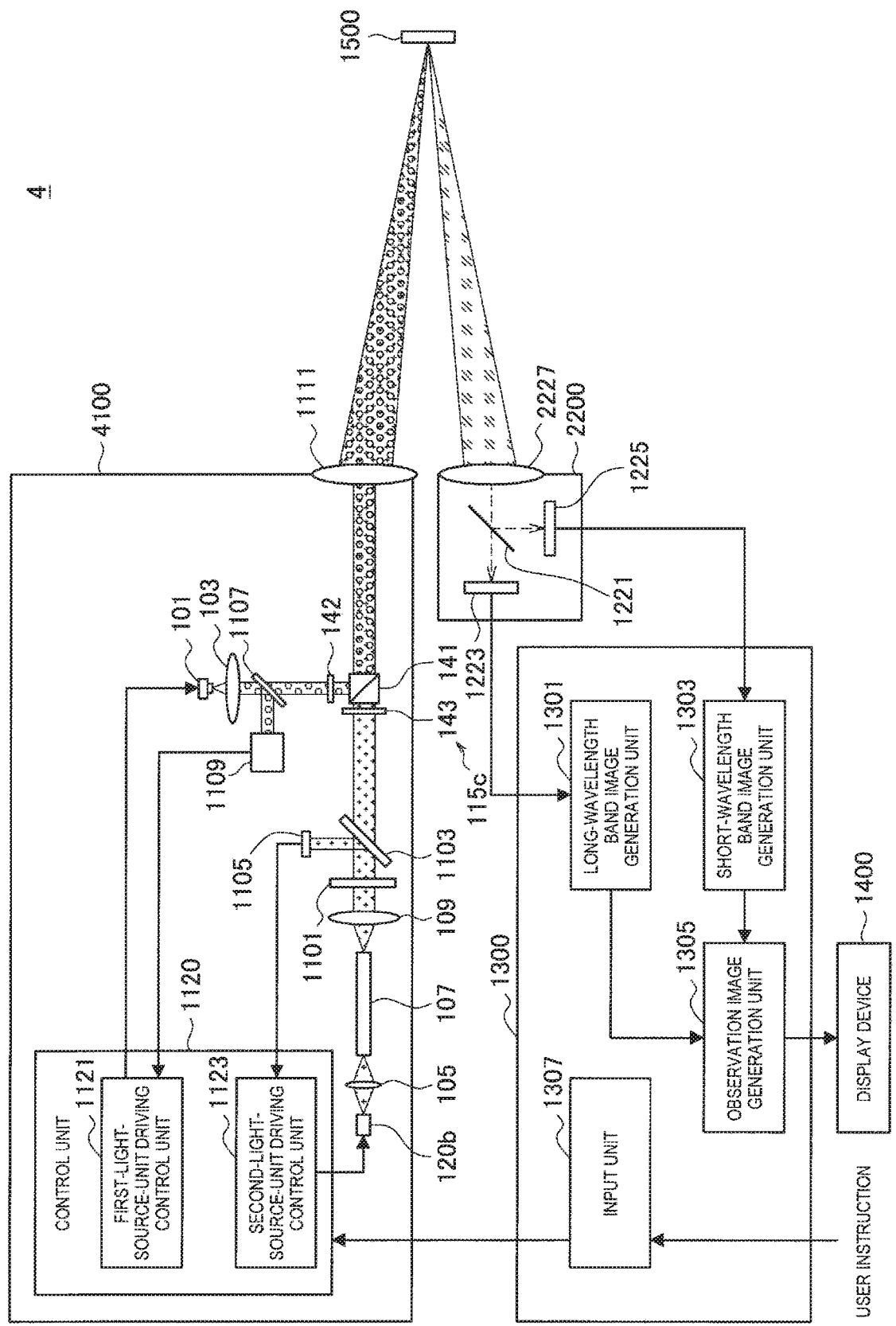
[Fig. 25]

[Fig. 26]
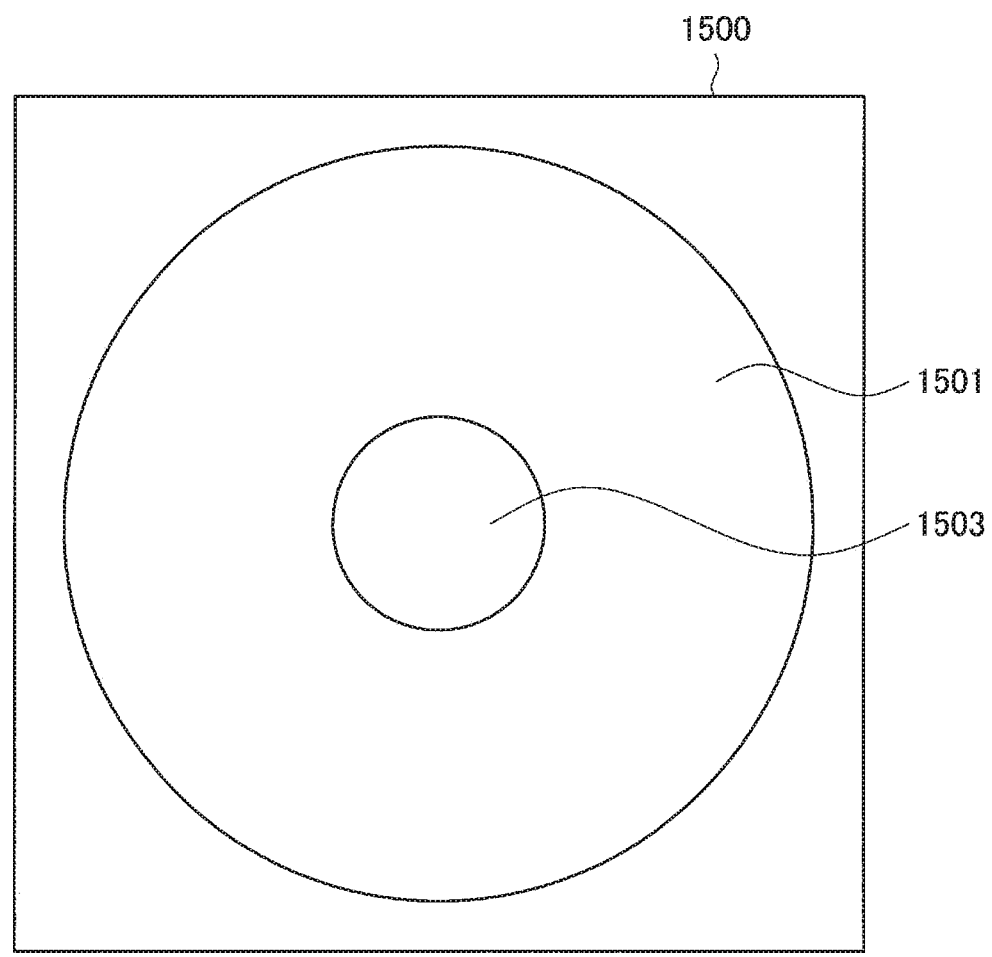

US 10,908,430 B2

MEDICAL IMAGING SYSTEM, ILLUMINATION DEVICE, AND METHOD

CROSS REFERENCE TO RELATED APPLICATIONS

This application is a U.S. National Phase of International Patent Application No. PCT/JP2015/006261 filed on Dec. 15, 2015, which claims priority benefit of Japanese Priority Patent Application No. JP 2014-262325 filed in the Japan Patent Office on Dec. 25, 2014, and Japanese Patent Application No. JP 2014-262323 filed Dec. 25, 2014. Each of the above-referenced applications is hereby incorporated herein by reference in its entirety.

TECHNICAL FIELD

The present disclosure relates to a medical imaging system, an illumination device, and a method for illuminating an observation site.

BACKGROUND ART

As a light source of an observation device such as an endoscope device or a microscope device for observing an operative field of a patient, lasers have been used in recent years in place of lamp light sources that were widely used before. Advantages of using lasers as light sources include that, for example, low power consumption can be expected due to the fact that electric-optic conversion efficiency of the light source is high, highlighted observation of a specific tissue is easy because of the narrow wavelength band of a laser when it is combined with a light absorption property of a tissue such as a blood vessel, and the like. Further advantages include that, for example, even lower power consumption can be expected when a laser is used as a light source for an endoscope device because its optical coupling efficiency with respect to a light guide is high, and due to high directionality of laser light, optical coupling efficiency with respect to a small-diameter light guide is high and thus a small-diameter endoscope insertion part can be realized.

For observation using laser light, various technologies for improving image quality of observation images have been developed. For example, when laser light is radiated to an object and the radiated field is observed, dark and bright dotted patterns appear due to high coherence of laser light. This phenomenon arises because random interference of light occurs on rough surfaces of the object and interference patterns having random intensity distribution appear. Such dotted patterns are called speckle noise, which can obstruct observation of a radiated field. Thus, in order to suppress occurrence of speckle noise and to obtain an observation image of high quality, the technologies exemplified in PTL 1 to PTL 5 mentioned below have been proposed.

For example, PTL 1 mentioned below discloses an endoscope system which uses a bundle fiber in which a plurality of optical fibers having an optical path difference length that is equal to or longer than a coherence length are bundled as a noise reducing device.

For example, PTL 2 mentioned below discloses a light source device for an endoscope which uses a plurality of modules that output intensity-modulated laser light from optical fibers and in which the optical fibers are further bundled to be optically coupled to a single optical fiber.

For example, PTL 3 mentioned below discloses an illumination device which includes a high-frequency superimposing mechanism that causes a semiconductor laser to oscillate in multiple modes by superimposing a high frequency signal on a driving current to be supplied to the semiconductor laser that is a light source.

For example, PTL 4 mentioned below discloses an endoscope in which a vibration applying mechanism which vibrates optical fibers is disposed inside an endoscope insertion part.

For example, PTL 5 mentioned below discloses an endoscope system which processes an obtained captured image and outputs the image as an observation image.

On the other hand, there is an observation device which switches to a normal observation mode in which an operative field is observed using light having a wide wavelength band such as white light and a special observation mode in which only a site within an operative field that emits fluorescence is intensively observed by detecting the fluorescence excited by light having a predetermined wavelength band (hereinafter also referred to as narrow-band light). In the observation device, radiated light is switched between white light and narrow-band light according to switching of the observation modes.

Here, when white light and narrow-band light are switched, it is desirable that the light be guided on the same optical axis and radiated to an operative field. This is because, when white light and narrow-band light are radiated along different optical paths, there is a possibility of a radiation angle of the white light and a radiation angle of the narrow-band light with respect to an operative field differing from each other, appearance of a shadow changes between an observation image (normal observation image) obtained in the normal observation mode and an observation image (fluorescence observation image) obtained in the special observation mode, and thus there is concern of visibility of an observation image for a user deteriorating.

As observation devices in which white light and narrow-band light can be switched and the light is guided on the same optical axis and radiated, those exemplified in PTL 6 to PTL 9 mentioned below have been proposed.

For example, PTL 6 mentioned below discloses an endoscope device in which white light and laser light (i.e., narrow-band light) are guided on the same optical axis via a half mirror.

For example, PTL 7 mentioned below discloses a light source device for an endoscope in which white light and laser light are multiplexed on the same optical axis by a multiplexing member including a combination of a transmission unit which transmits white light and a reflection unit which reflects laser light.

For example, PTL 8 and PTL 9 mentioned below disclose light source devices for endoscopes in which white light and laser light are guided on the same optical axis via a dichroic mirror.

CITATION LIST

Patent Literature

[PTL 1]
JP 2008-043493A
[PTL 2]
JP 2009-240560A
[PTL 3]
JP 2010-042153A
[PTL 4]
JP 2010-172651A
[PTL 5]
JP 2012-005785A

[PTL 6]
JP 2009-131496A
[PTL 7]
JP 2012-081133A
[PTL 8]
JP 2005-342033A
[PTL 9]
JP 2006-000157A

SUMMARY

Technical Problem

However, since a bundle fiber device having the lengths of element wires that are equal to or longer than a coherence length is necessary for the above-described PTL 1, a plural-fiber light source device and an intensity modulation device are necessary for the above-described PTL 2, a high-frequency superimposing circuit is necessary for the above-described PTL 3, a mechanical vibration applying mechanism is necessary for the above-described PTL 4, and an imaging processing device and another device in addition to a configuration for realizing the function as a light source are necessary for above-described PTL 5, an overall size of a device increases and an extra cost for reducing speckle noise (i.e., for high image quality) is necessary. In addition, in the technologies disclosed in the above-described PTL 6 to PTL 9, for example, reduction of speckle noise was not considered and it is difficult to say that achieving high quality of observation images was sufficiently addressed.

As described above, with respect to an observation device for observing an operative field of a patient, a technology which realizes switching of a wavelength band of radiation light according to observation applications while obtaining an observation image of higher quality has yet to be sufficiently addressed. Therefore, the present disclosure proposes a novel and improved illumination device, illuminating method, and observation device with which switching a wavelength band of radiation light and obtaining an observation image of higher quality are simultaneously achieved.

Solution to Problem

According to an aspect of the present application, a medical imaging system including an illumination device and a medical imaging device is provided. The illumination device includes a first light source configured to emit first light having a wavelength range. The illumination device further includes a second light source configured to emit second light having at least one predetermined wavelength band. The at least one predetermined wavelength band is within the wavelength range. The illumination device further includes a dichroic mirror configured to attenuate a portion of the wavelength range corresponding to the at least one predetermined wavelength band and to multiplex the second light with the first light such that the portion of the wavelength range of the first light is attenuated. The light multiplexed by the dichroic mirror is emitted from the illumination device along an optical axis and irradiates an observation site. The medical imaging device includes at least one image sensor configured to receive light from the observation site.

According to an aspect of the present application, an illumination device is provided. The illumination device includes a first light source configured to emit first light having a wavelength range. The illumination device further includes a second light source configured to emit second light having at least one predetermined wavelength band. The at least one predetermined wavelength band is within the wavelength range. The illumination device further includes a dichroic mirror configured to attenuate a portion of the wavelength range corresponding to the at least one predetermined wavelength band and to multiplex the second light with the first light such that the portion of the wavelength range of the first light is attenuated. The light multiplexed by the dichroic mirror is emitted from the illumination device along an optical axis and irradiates an observation site.

According to an aspect of the present application, a method for illuminating an observation site is provided. The method includes irradiating the observation site with light emitted by an illumination device. The light has a wavelength range. The method further includes adjusting an intensity of at least one predetermined wavelength band within the wavelength range such that the at least one predetermined wavelength band has a higher intensity than portions of the wavelength range outside the at least one predetermined wavelength band.

Advantageous Effects of Invention

According to one or more of embodiments of the present disclosure described above, switching the wavelength bands of radiation light and obtaining a higher-quality observation image can be simultaneously achieved. Note that the effects described above are not necessarily limited, and along with or instead of the effects, any effect that is desired to be introduced in the present specification or other effects that can be expected from the present specification may be exhibited.

BRIEF DESCRIPTION OF DRAWINGS

FIG. 1 is a diagram illustrating a configuration example of an illumination device according to a first embodiment.

FIG. 2 is an illustrative diagram for describing a configuration of a light guide on which output light from the illumination device illustrated in FIG. 1 is incident.

FIG. 4 shows graphs for describing characteristics of a dichroic mirror of the illumination device illustrated in FIG. 1.

FIG. 5 shows graphs for describing characteristics of a dichroic mirror of the illumination device illustrated in FIG. 1.

FIG. 7 is a diagram illustrating a configuration example of an illumination device according to a second embodiment.

FIG. 8 is a diagram illustrating a configuration example of another illumination device when white light and laser light are multiplexed as diverging light.

FIG. 9 is a diagram illustrating a configuration example of another illumination device when a light source of another wavelength band is added.

FIG. 10 is a diagram illustrating a configuration example of an endoscope device to which the illumination devices according to the first and second embodiments and respective modified examples are applied.

FIG. 11 is a graph for describing characteristics of a dichroic mirror of the endoscope device illustrated in FIG. 10.

FIG. 12 is a graph for describing characteristics of a dichroic mirror of the endoscope device illustrated in FIG. 10.

FIG. 13 is a diagram illustrating another configuration example of the endoscope device illustrated in FIG. 10.

FIG. 14 is a diagram illustrating a configuration example of a microscope device to which the illumination devices according to the first and second embodiments and the respective modified examples are applied.

FIG. 15 is an illustrative diagram for describing a radiation range of radiation light with respect to an observation site.

FIG. 16 is a diagram illustrating a configuration example of an illumination device according to a third embodiment.

FIG. 17 is an illustrative diagram for describing a configuration of a light guide on which output light from the illumination device illustrated in FIG. 16 is incident.

FIG. 18 shows graphs for describing characteristic of light multiplexed by a multiplexing member of the illumination device illustrated in FIG. 16.

FIG. 19 is a diagram illustrating a configuration example of an illumination device according to a fourth embodiment.

FIG. 20 is a diagram illustrating a configuration example of another illumination device when white light and laser light are multiplexed as diverging light.

FIG. 21 is a diagram illustrating a configuration example of another illumination device when a light source of another wavelength band is added.

FIG. 22 is a diagram illustrating a configuration example of an endoscope device to which the illumination devices according to the third and fourth embodiments and respective modified examples are applied.

FIG. 23 shows graphs for describing characteristic of light multiplexed by a multiplexing member of the endoscope device illustrated in FIG. 22.

FIG. 24 is a diagram illustrating another configuration example of the endoscope device illustrated in FIG. 22.

FIG. 25 is a diagram illustrating a configuration example of a microscope device to which the illumination devices according to the third and fourth embodiments and the respective modified examples are applied.

FIG. 26 is an illustrative diagram for describing a radiation range of radiation light with respect to an observation site.

DESCRIPTION OF EMBODIMENTS

Figures 3A, 3B, 3C:
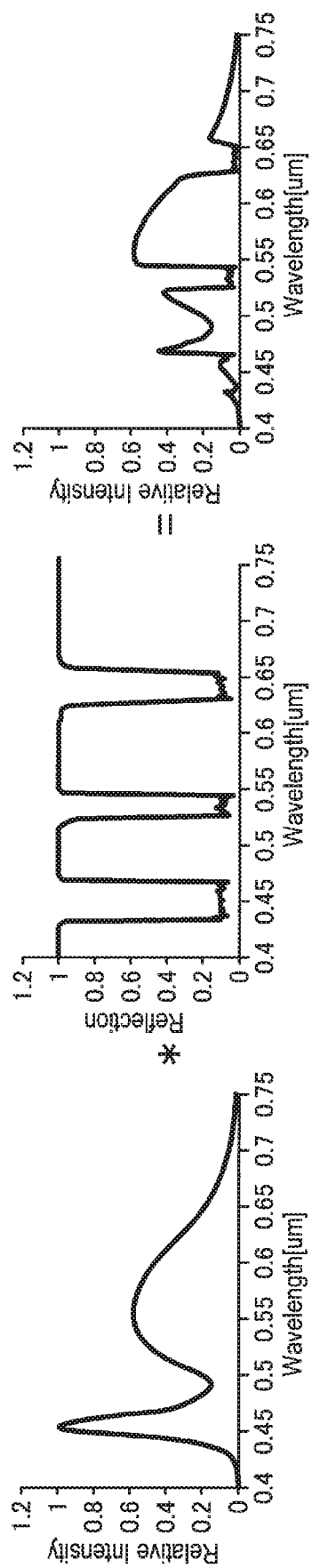
FIGS. 3(a), 3(b) and 3(c) show graphs for describing characteristics of a dichroic mirror of the illumination device illustrated in FIG. 1.

Hereinafter, preferred embodiments of the present disclosure will be described in detail with reference to the appended drawings. Note that, in this description and the appended drawings, structural elements that have substantially the same function and structure are denoted with the same reference numerals, and repeated explanation of these structural elements is omitted.

Note that description will be provided in the following order.

I. Illumination device that includes a multiplexing unit with a dichroic mirror
1. First embodiment
1-1. Configuration of an illumination device
1-2. Speckle noise reduction effect
2. Second embodiment
3. Modified examples
3-1. Modified example in which white light and laser light are multiplexed as diverging light
3-2. Modified example in which a light source of another wavelength band is added
4. Application examples
4-1. Regarding PDD and PDT
4-2. Endoscope device
4-2-1. Configuration of an endoscope device
4-2-2. Operation of the endoscope device
4-2-3. Another configuration example of the endoscope device
4-3. Microscope device
4-3-1. Configuration of a microscope device
4-3-2. Operation of the microscope device
II. Illumination device that includes a multiplexing unit with a polarization conversion element and a polarizing beam splitter
5. Third embodiment
6. Fourth embodiment
7. Modified examples
7-1. Modified example in which white light and laser light are multiplexed as diverging light
7-2. Modified example in which a light source of another wavelength band is added
8. Application example
8-1. Regarding PDD and PDT
8-2. Endoscope device
8-2-1. Configuration of an endoscope device
8-2-2. Operation of the endoscope device
8-2-3. Another configuration example of the endoscope device
8-3. Microscope device
8-3-1. Configuration of a microscope device
8-3-2. Operation of the microscope device
9. Supplement
I. Illumination Device that Includes a Multiplexing Unit with a Dichroic Mirror I. Illumination device that includes a multiplexing unit with a dichroic mirror

1. FIRST EMBODIMENT 1-1. Configuration of an Illumination Device

A configuration of an illumination device according to a first embodiment of the present disclosure will be described with reference to FIGS. 1 to 5. FIG. 1 is a diagram illustrating a configuration example of the illumination device according to the first embodiment. FIG. 2 is an illustrative diagram for describing a configuration of a light guide on which output light from the illumination device illustrated in FIG. 1 is incident. FIGS. 3(*a*), 3(*b*) and 3(*c*) to 5 are diagrams for describing characteristics of a dichroic mirror of the illumination device illustrated in FIG. 1.

Note that the illumination device according to the first embodiment and one according to a second embodiment to be described below can be properly applied to a light source unit of an observation device such as an endoscope device or a microscope device for observing an operative field of a patient. Hereinbelow, cases in which the illumination devices according to the first and second embodiments are applied to an endoscope device will be described as examples except for (4-3. Endoscope device) described below. When the illumination devices according to the first and second embodiments are applied to endoscope devices, light emitted from the illumination devices is incident on an end of a light guide that continues inside a lens barrel of an endoscope, and therefore drawings showing configurations of the illumination devices provided below also illustrate one end of the light guide on which light is incident.

Referring to FIG. 1, the illumination device 10 according to the first embodiment includes a first light source unit 101 that emits white light and a first collimator optical system 103. In addition, the illumination device 10 further includes a second light source unit 120 which includes at least one laser light source that emits light of a predetermined wavelength band, a coupling optical system 105, an optical fiber 107, a third collimator optical system 109, a diffusion member 111, a second collimator optical system 113, a dichroic mirror 115, and a condenser optical system 117. In addition, although not illustrated, the illumination device 10 includes driving control units which control driving of the first light source unit 101 and the second light source unit 120 (which correspond to a first-light-source-unit driving control unit 1121 and a second-light-source-unit driving control unit 1123 shown in FIG. 10 to be described below).

White light emitted from the first light source unit 101 becomes substantially parallel light as it passes through the first collimator optical system 103, and is incident on the dichroic mirror 115. On the other hand, laser light emitted from the second light source unit 120 passes through the coupling optical system 105, the optical fiber 107, the third collimator optical system 109, the diffusion member 111, and the second collimator optical system 113 in this order, thereby turning into substantially parallel light, and is incident on the dichroic mirror 115. The dichroic mirror 115 multiplexes the white light and the laser light, and the multiplexed light is incident on an end of a light guide 130 via the condenser optical system 117.

Here, as a laser light source included in the second light source unit 120, one that can emit light of a wavelength band which can function as excitation light in fluorescence observation can be mounted in the illumination device 10 according to an observation purpose. In addition, the illumination device 10 is configured to switch modes including a normal observation mode in which an operative field is observed using white light, a special observation mode in which, by detecting fluorescence excited by light of a predetermined wavelength band (hereinafter also referred to as narrow-band light), a site within an operative field emitting the fluorescence is intensively observed, and a normal/special observation mode in which normal observation and special observation are simultaneously performed (details thereof will be described in (4. Application examples) below). Note that fluorescence observation in the special observation mode and the normal/special observation mode may involve detecting self-fluorescence of a site radiated with excitation light, or detecting chemical fluorescence brought by various fluorescence reagents (photosensitive pharmaceutical agents) introduced into a radiated site.

In the normal observation mode, white light generated by multiplexing white light from the first light source unit 101 and laser light from the second light source unit 120 is radiated to an operative field. Accordingly, a normal observation image based on the white light is obtained. Note that, in description below, white light generated by multiplexing white light from the first light source unit 101 and laser light from the second light source unit 120 will also be referred to as multiplexed white light for the sake of convenience in order to distinguish it from white light from the first light source unit 101. In the normal observation mode, an output of laser light from the second light source unit 120 is appropriately adjusted so that multiplexed white light has a desired hue (for example, a hue similar to original white light emitted from the first light source unit 101, a hue corresponding to an arbitrary standard illuminant, or the like).

In the special observation mode, white light is not emitted from the first light source unit 101 (i.e., the white light source of the first light source unit 101 is turned off), only laser light of a wavelength band set according to an observation purpose is emitted from the second light source unit 120 (i.e., only the laser light source suitable for the observation purpose is turned on), and thus narrow-band light is radiated to an operative field. Accordingly, a fluorescence observation image based on fluorescence is obtained. In the fluorescence observation image, only a site suitable for the observation purpose, for example, a tumor or the like, is shown.

In the normal/special observation mode, multiplexed white light is radiated to an operative field as in the normal observation mode; however, an output of laser light from the second light source unit 120 is adjusted to have an intensity (i.e., intensity suitable for fluorescence observation) according to an observation purpose. Accordingly, an image in which a normal observation image and a special observation image overlap is obtained.

Each constituent member of the illumination device 10 will be described in more detail below.

At least one second light source unit 120 is provided in the illumination device 10. The second light source unit 120 includes at least one laser light source which emits laser light of a predetermined wavelength band. In the illustrated example, the second light source unit 120 includes a laser light source 121R that emits laser light of a red band (for example, laser light having the center wavelength of about 638 nm), a laser light source 121G that emits laser light of a green band (for example, laser light having the center wavelength of about 532 nm), and a laser light source 121B that emits laser light of a blue band (for example, laser light having the center wavelength of about 450 nm). Each of the laser light sources 121R, 121G and 121B is provided with a collimator optical system, and thus laser light of each wavelength band is emitted as a parallel luminous flux.

As the laser light sources 121R, 121G and 121B, various known laser light sources, for example, a semiconductor laser, a solid-state laser, and the like, can be used. Alternatively, as the laser light sources 121R, 121G and 121B, a combination of the laser light sources and a wavelength conversion mechanism may be used. In the second light source unit 120, driving of each of the laser light sources 121R, 121G and 121B can be controlled independently.

As described above, the second light source unit 120 can include the laser light sources 121R, 121G and 121B which emit light of, for example, respective wavelength bands corresponding to the three primary colors of light. By configuring the second light source unit 120 in this manner, outputs of the laser light sources 121R, 121G and 121B corresponding to the respective colors are appropriately adjusted, and thereby a color temperature of multiplexed white light can be adjusted.

The first embodiment, however, is not limited to the above example, and a type of laser light source included in the second light source unit 120 may be appropriately selected according to an observation purpose, a type of observation target, and the like. When various kinds of fluorescence observation are to be performed, for example, the second light source unit 120 can be configured to include laser light sources which emit laser light of wavelength bands corresponding to excitation light according to each fluorescence observation method. When observation using indocyanine green (ICG) fluorescence contrast radiography is performed, for example, the second light source unit 120 is configured to include at least a laser light source that emits laser light of a near-infrared band.

The second light source unit 120 further includes a dichroic mirror 122R that reflects light of a wavelength band corresponding to red laser light from the laser light source 121R, a dichroic mirror 122G that reflects light of a wavelength band corresponding to green laser light from the laser light source 121G and a dichroic mirror 122B that reflects light of a wavelength band corresponding to blue laser light from the laser light source 121B. The dichroic mirrors 122R, 122G, and 122B multiplex laser light emitted from the respective laser light sources 121R, 121G and 121B becoming a parallel luminous flux, and the light is emitted as one luminous flux toward the coupling optical system 105 in the later stage.

Note that the dichroic mirrors 122R, 122G, and 122B are examples of multiplexing members that multiplex laser light from the laser light sources 121R, 121G and 121B, and as the multiplexing members, other arbitrary members may be used. For example, as a member for multiplexing laser light from each of the laser light sources 121R, 121G and 121B, a dichroic prism may be used when multiplexing is performed based on wavelengths, a polarizing beam splitter (PBS) may be used when multiplexing is performed based on polarization, or a beam splitter may be used when multiplexing is performed based on amplitude.

The coupling optical system 105 includes, for example, a condenser lens (collector lens), and causes laser light emitted from the second light source unit 120 to be optically coupled to an incidence end of the optical fiber 107. Note that, although the coupling optical system 105 is illustrated as one convex lens in the example illustrated in FIG. 1 for the sake of convenience, a detailed configuration of the coupling optical system 105 is not limited thereto. The coupling optical system 105 may have the function of causing laser light to be coupled to the incidence end of the optical fiber 107, and may be configured to be appropriately combined with a known optical element.

The optical fiber 107 guides laser light emitted from the second light source unit 120 to the third collimator optical system 109 provided in the later stage. Since light emitted from the optical fiber 107 is a rotationally symmetric beam, as the optical fiber 107 guides laser light, luminance distribution becomes more uniform within its plane.

A type of the optical fiber 107 is not particularly limited, but as the optical fiber 107, a known multi-mode optical fiber (for example, a step-index multi-mode optical fiber) can be used. In addition, the core diameter of the optical fiber 107 is not particularly limited, and one with a core diameter of about, for example, 1 mm may be used.

In the first embodiment, the laser light is guided to the incidence end of the optical fiber 107 such that the incidence numerical apertures of the laser light from the laser light sources 121R, 121G and 121B coincide with each other at the incidence end of the optical fiber 107. At this time, it is desirable that, by optimizing the focal length of a lens that collimates laser light emitted from the laser light sources 121R, 121G and 121B, adjusting incidence positions of the laser light on the coupling optical system 105 (i.e. collector lens), or the like, laser light emitted from an emission end of the optical fiber 107 be a solid ray of light of which the amount near the central optical axis of the optical fiber 107 is equal to the amount in the peripheral part, rather than a doughnut-shaped ray of light of which the amount near the central optical axis of the optical fiber 107 is smaller than the amount in the peripheral part.

The third collimator optical system 109 is provided in the later stage of the emission end of the optical fiber 107, and converts laser light emitted from the optical fiber 107 into a parallel luminous flux. As the third collimator optical system 109 converts laser light into a parallel luminous flux, a diffusion state of the laser light in the diffusion member 111 provided in the later stage can be easily controlled. Note that, although the third collimator optical system 109 is illustrated as one convex lens in the example illustrated in FIG. 1 for the sake of convenience, a detailed configuration of the third collimator optical system 109 is not limited thereto. The third collimator optical system 109 may have the function of converting laser light into a parallel luminous flux, and may be configured to be appropriately combined with a known optical element.

The diffusion member 111 is provided near a focal position on the rear side of the third collimator optical system 109, and included in a secondary light source by diffusing the laser light that has become the parallel luminous flux output from the third collimator optical system 109. That is to say, a light emission end of the diffusion member 111 functions as a secondary light source. In addition, the angle of light emitted from the optical fiber 107 is generally uneven depending on laser light; however, divergence angles become uniform after light passes the diffusion member 111. As described above, according to the first embodiment, color unevenness at the time of radiation, which is expected to occur in, for example, the general existing illumination devices introduced in above-described PTL 6 to PTL 9, is reduced due to the diffusion member 111.

A size of the secondary light source formed by the diffusion member 111 can be controlled according to a focal length of the third collimator optical system 109. In addition, the NA of emitted light can be controlled according to a diffusion angle of the diffusion member 111. Due to these two effects, both the size of a condensing spot and the incidence NA when light is coupled to the incidence end of the light guide 130 can be controlled independently of each other. Note that, although the actual range of the periphery of a focal position on the rear side of the third collimator optical system 109 at which the diffusion member 111 is to be disposed is not particularly limited, the range is preferably set to, for example, a range of about ±10% of focal distances upstream and downstream from the focal position on the rear side of the third collimator optical system 109.

Note that a specific type of the diffusion member 111 is not particularly limited, and a known diffusion element may be used as the diffusion member 111. As examples of such a diffusion member, for example, a frosted ground glass, an opal diffuser that uses a diffusion characteristic by dispersing light diffusion materials within glass, and a holographic diffuser can be exemplified. A holographic diffuser is made by creating holograph patterns on a predetermined board, and it is particularly preferable to be used as the diffusion member 111 because a diffusion angle of emitted light can be set to an arbitrary angle.

Laser light emitted from the diffusion member 111 is guided to the second collimator optical system 113. The second collimator optical system 113 converts the light from the diffusion member 111 (i.e., light from the secondary light source) into a parallel luminous flux to cause the light to be incident on the dichroic mirror 115. Note that the dichroic mirror 115 may be a dichroic prism.

Here, the laser light that has passed through the second collimator optical system 113 may not be completely parallel light, and may be diverging light close to a parallel light state. In other words, the second collimator optical system 113 and the condenser optical system 117 to be described below may be a finite conjugate rather than an infinite conjugate. In the present specification, for the sake of convenience, light that has passed through a collimator optical system and becomes parallel light or light that is closed to a parallel light state will be referred to as substantially parallel light. That is, substantially parallel light is a concept that includes parallel light or diverging light. Note that a configuration example of the illumination device 10 when white light and laser light are multiplexed as diverging light will be described again in (3-1. Modified example in which white light and laser light are multiplexed as diverging light) in detail.

At least one first light source unit 101 is provided in the illumination device 10, and emits white light. A type of white light source included in the first light source unit 101 is not limited as long as it emits white light. As the white light source, for example, an arbitrary light source such as a white light emitting diode (LED), a laser-excited fluorescent substance, a xenon lamp, or a halogen lamp may be used. In the first embodiment, as an example, a so-called fluorescent substance-type white LED that uses a fluorescent substance excited by a blue LED is assumed to be used as the white light source of the first light source unit 101.

White light emitted from the first light source unit 101 is converted into a parallel luminous flux by the first collimator optical system 103, and is incident on the dichroic mirror 115 from a direction different from that of the laser light emitted from the diffusion member 111 (in the illustrated example, the direction in which the optical axes are substantially orthogonal to each other). Note that the white light that has passed through the first collimator optical system 103 may not be completely parallel light. In other words, the first collimator optical system 103 and the condenser optical system 117 to be described below may be a finite conjugate rather than an infinite conjugate. That is, the first collimator optical system 103 converts the white light into substantially parallel light and causes it to be incident on the dichroic mirror 115.

Note that, although the first collimator optical system 103 is illustrated as one convex lens in the example shown in FIG. 1 for the sake of convenience, a detailed configuration of the first collimator optical system 103 is not limited thereto. The first collimator optical system 103 may have the function of converting white light into substantially parallel light, and may be configured to be appropriately combined with a known optical element.

The dichroic mirror 115 multiplexes the white light emitted from the first light source unit 101 and the laser light emitted from the second light source unit 120. In the illustrated example, the dichroic mirror 115 is designed to transmit only light of the wavelength band corresponding to the laser light from the second light source unit 120 and to reflect light of other wavelength bands.

In the illumination device 10, the diffusion member 111, the second collimator optical system 113, the dichroic mirror 115, and the condenser optical system 117 are disposed substantially in a line in this order. In addition, the first light source unit 101 and the first collimator optical system 103 are disposed such that white light is incident on the dichroic mirror 115 from the direction in which the white light is substantially orthogonal to the optical axis of the laser light. Thus, the laser light that has been emitted from the diffusion member 111 and incident on the dichroic mirror 115 passes through the dichroic mirror 115 and is incident on the condenser optical system 117. In addition, of the white light incident on the dichroic mirror 115, a component other than the wavelength band of the laser light is reflected by the dichroic mirror 115 and is incident on the condenser optical system 117.

In this manner, the dichroic mirror 115 has the functions of attenuating or removing the component of light of the wavelength band corresponding to the laser light emitted from the second light source unit 120 from the white light emitted from the first light source unit 101, and multiplexing the white light, of which the component of light of the wavelength band corresponding to the laser light has been attenuated or removed, with the laser light emitted from the second light source unit 120. That is to say, the light multiplexed by the dichroic mirror 115 can be white light of which a predetermined wavelength band is complemented by the laser light. Note that details of the characteristics of the dichroic mirror 115 and the characteristic of light multiplexed by the dichroic mirror 115 will be described below with reference to FIGS. 3(a), 3(b) and 3(c) to 5.

The condenser optical system 117 is configured with, for example, a condenser lens (collector lens), and causes light multiplexed by the dichroic mirror 115 to form an image on the incidence end of the light guide 130 at a paraxial lateral magnification.

Here, an image-forming magnification of the second collimator optical system 113 and the condenser optical system 117 ([a focal length of the condenser optical system 117]/[a focal length of the second collimator optical system 113]) is set such that a size and a divergence angle of the secondary light source match the core diameter and the incidence NA of the light guide 130. In addition, an image-forming magnification of the first collimator optical system 103 and the condenser optical system 117 ([a focal length of the condenser optical system 117]/[a focal length of the first collimator optical system 103]) is set such that they match the core diameter and the incidence NA of the light guide so that white light forms an image on the incidence end of the light guide 130 with high efficiency.

FIG. 2 illustrates a configuration example of the light guide 130. In FIG. 2, an end of the light guide 130 is illustrated. The light guide 130 includes a bundle of a plurality of optical fibers each including a fiber core and a fiber clad. Here, the condenser optical system 117 according to the first embodiment is configured such that light from the secondary light source forms an image so that the light fills the area of an illumination target (the incidence end of the light guide 130 in the first embodiment) as much as possible, unlike in a general configuration. That is to say, in the first embodiment, the condenser optical system 117 can be configured to condense light from the secondary light source on the incidence end of the light guide 130 so that the size of an image of the secondary light source formed on the incidence end of the light guide 130 becomes substantially the same as the diameter of the incidence end of the light guide 130. Accordingly, speckle noise of the entire illumination device 10 can be reduced.

Speckle noise is known to depend on luminance distribution of a light source. For example, when a light source is an ideal light source, luminance distribution thereof can be regarded as a delta function, and all points on an object surface irradiated with light from the light source interfere with each other, and thus coherence becomes high. Consequently, speckle noise increases. Such a light source (point light source) is called a coherent light source, and speckle noise increases when such a coherent light source is used.

On the other hand, when an infinitely large uniform light source is assumed as a light source, luminance distribution thereof becomes uniform, interference occurs only at the same position on an object surface irradiated with light from the light source, and thus coherence becomes low. Consequently, speckle noise decreases. Such an infinitely large light source is called an incoherent light source, and speckle noise decreases when an incoherent light source is used.

A light source actually mounted in the illumination device 10 is a partially coherent light source that is spatially positioned between a coherent light source and an incoherent light source, and thus, as the size of the light source becomes seemingly larger and luminance distribution of the light source becomes more uniform, coherence and speckle noise are considered to be reduced.

Here, when light from the secondary light source is condensed on the incidence end of the light guide 130 so that an image of the secondary light source is smaller than the diameter of the incidence end of the light guide 130, only some optical fibers included in the light guide 130 contribute to light guidance, and as a result, when emitted light from the light guide 130 is radiated to an observation site, the size of the light source when the observation site is observed from a radiated face becomes seemingly small, and there is concern of speckle noise worsening.

On the other hand, when light from the secondary light source is condensed on the incidence end of the light guide 130 so that an image of the secondary light source is larger than the diameter of the incidence end of the light guide 130, vignetting of laser light arises on the incidence end face of the light guide 130, and there is concern of efficiency in light coupling decreasing.

Thus, by condensing light from the secondary light source on the incidence end of the light guide 130 so that the size of an image of the secondary light source becomes substantially the same as the diameter of the incidence end of the light guide 130 as described above, speckle noise can be reduced while improving efficiency in light coupling to the incidence end face of the light guide 130.

Here, such a configuration for reducing speckle noise is not applied to, for example, existing general illumination devices as introduced in PTL 6 to PTL 9 described above. In this manner, in the illumination device 10 according to the first embodiment, an observation image in which speckle noise is reduced more than in a general illumination device can be obtained.

Note that, although the condenser optical system 117 is illustrated as one convex lens in the example shown in FIG. 1 for the sake of convenience, a detailed configuration of the condenser optical system 117 is not limited thereto. The condenser optical system 117 may have the respective functions as described above, and may be configured to be appropriately combined with a known optical element.

Here, the characteristics of the dichroic mirror 115 and the characteristic of light multiplexed by the dichroic mirror 115 will be described with reference to FIGS. 3(a), 3(b) and 3(c) to 5. FIG. 3(a) illustrates an example of the spectrum of white light emitted from the first light source unit 101. FIG. 3(b) illustrates an example of a reflection characteristic of the dichroic mirror 115.

Referring to FIG. 3(b), the dichroic mirror 115 has a characteristic of reflecting most of the wavelength band of white light and transmitting light of the wavelength band corresponding to laser light emitted from the second light source unit 120. In the illustrated example, the dichroic mirror 115 is designed to transmit light of a wavelength band with a predetermined width including the center wavelength of red laser light of about 638 nm, light of a wavelength band with a predetermined width including the center wavelength of green laser light of about 532 nm, and light of a wavelength band of a predetermined width including the center wavelength of blue laser light of about 450 nm.

FIG. 3(c) shows an example of the spectrum of light after white light emitted from the first light source unit 101 passes through the dichroic mirror 115. As shown in FIG. 3(c), white light that has passed through the dichroic mirror 115 has an attenuated component of the wavelength bands corresponding to those of laser light emitted from the second light source unit 120. Since only wavelength bands corresponding to those of laser light are attenuated by the dichroic mirror 115, loss incurred when the white light and the laser light are multiplexed can be suppressed to the minimum level. In addition, when the white light is substantially parallel light and its incidence angle is broad, a wavelength shift occurs and the attenuated wavelength bands are also shifted due to dependence of the dichroic mirror 115 on an incidence angle, and thus the spectrum of light after being emitted from the light guide 130 tends to be more uniform than in FIG. 3(c).

Note that the characteristics of the dichroic mirror 115 shown in FIGS. 3(a), 3(b) and 3(c) are examples, and the first embodiment is not limited thereto. The characteristics of the dichroic mirror 115 can be appropriately set according to a characteristic of a laser light source used as the second light source unit 120. For example, when observation is performed using the ICG fluorescence contrast radiography, laser light of a near-infrared band (for example, laser light having the center wavelength of about 808 nm) can be used as the second light source unit 120, and thus the dichroic mirror 115 having a characteristic of transmitting light in the range corresponding to the wavelength band of the laser light is used.

FIG. 4 shows an example of a transmission characteristic of the dichroic mirror 115. As described with reference to FIG. 3(b), it is ascertained that the dichroic mirror 115 transmits light of the wavelength band corresponding to laser light emitted from the second light source unit 120 and reflects most of the wavelength band of the white light emitted from the first light source unit 101. In the illustrated example, the dichroic mirror 115 is set to transmit about 90% of light of the corresponding wavelength band for the purpose of improving use efficiency of the laser light.

FIG. 5 shows an example of the spectrum of light obtained after the dichroic mirror 115 multiplexes white light emitted from the first light source unit 101 and laser light emitted from the second light source unit 120. In the illustrated example, the spectrum obtained when red laser light, green laser light, and blue laser light are multiplexed with white light is shown. By multiplexing white light and the laser light in this manner, so-called new white light (i.e., multiplexed white light) can be generated in the first embodiment. The multiplexed white light is radiated to an operative field in the normal observation mode and the normal/special observation mode in the first embodiment. Note that, in the special observation mode, only the second light source unit 120 is driven without driving the first light source unit 101, and laser light of a wavelength band corresponding to excitation light at the time of fluorescence observation is radiated to an operative field.

In the existing general illumination devices introduced in, for example, PTLs 6, 8, and 9 described above, however, a multiplexing member guides white light and laser light onto the same optical axis, but any of white light and laser light is selectively radiated to an operative field by appropriately controlling driving of a white light source and a laser light source, or appropriately controlling removal of a filter from an optical path and disposition thereof on the optical path. That is to say, in the technologies of PTLs 6, 8, and 9, white light from the white light source is directly radiated to an operative field in the normal observation mode. In addition, white light generated when a multiplexing member multiplexes white light and laser light is radiated to an operative field in the technology disclosed in PTL 7; however, the multiplexing member has a part configured to be a transmissive unit which transmits components of all wavelength bands of the white light, and as a result, the white light from a white light source that has penetrated the transmissive unit is directly radiated to an operative field.

As described above, in the existing general illumination devices exemplified in PTL 6 to PTL 9 described above, white light from the white light source such as a halogen lamp or a white LED can be radiated directly to an operative field in the normal observation mode. Thus, although the spectrum of the white light radiated to the operative field can be adjusted to some extent by using various filters and the like, the spectrum is basically fixed to the type of the white light source, and thus it is difficult to control the spectrum of the radiated light in detail.

On the other hand, according to the first embodiment, white light generated by multiplexing white light emitted from the first light source unit 101 and laser light emitted from the second light source unit 120 can be radiated to an operative field in the normal observation mode and the normal/special observation mode as described above. In addition, the second light source unit 120 can include the laser light sources 121R, 121G and 121B which emit light of, for example, respective wavelength bands corresponding to the three primary colors of light. According to this configuration, by appropriately adjusting a mixing ratio of laser light emitted from the second light source unit 120, the spectrum of the multiplexed white light can be controlled and a color temperature thereof can be adjusted. In this manner, a color temperature can be adjusted on a light source side, rather than being adjusted by a filter or the like in a later stage of the illumination device according to the first embodiment.

Note that, at this time, a mixing ratio of laser light emitted from the second light source unit 120 may be adjusted by, for example, controlling driving currents of the respective laser light sources 121R, 121G and 121B and thereby controlling output of the laser light, or may be controlled by adjusting transmittances of the dichroic mirror 115 with respect to light of the wavelength bands of the laser light.

As an example, Table 1 below shows an example in which outputs of respective light sources for realizing a predetermined color temperature for multiplexed white light are set. When it is desired to realize white light of a standard illuminant D65 (x=0.313, y=0.329) with the illumination device 10, for example, the outputs of the white light source and the laser light sources may be set as in the example (a) of Table 1. In addition, when it is desired to realize white light of a common illuminant D50 (x=0.346, y=0.359) with the illumination device 10, for example, the outputs of the white light source and the laser light sources may be set as in the example (b) of Table 1. Note that the setting shown in Table 1 below is merely an example, and it is needless to say that the color temperature of white light can be realized using various other light sources by appropriately adjusting the outputs of the white light source and the laser light sources.

TABLE 1

| Light Source | (a) D65 | (b) D50 |
|---|---|---|
| Red Laser (638 nm) | 0.12 W | 17 W |
| Green Laser (532 nm) | 0.08 W | 0.10 W |
| Blue Laser (450 nm) | 0.08 W | 0.08 W |
| White LED | 0.50 W | 0.50 W |

The configuration of the illumination device 10 according to the first embodiment has been described above with reference to FIGS. 1 to 5. According to the first embodiment described above, since divergence angles of a plurality of laser light beams output from the second light source unit 120 become uniform by providing the diffusion member 111 on the optical path of the laser light, color unevenness during radiation of output light from the illumination device 10 is reduced. In addition, by configuring light from the secondary light source to form an image on the incidence end of the light guide 130 so that the light fills the area of the incidence end of the light guide 130 as much as possible, the condenser optical system 117 can reduce speckle noise in the illumination device 10 as a whole. In addition, by adjusting a mixing ratio of laser light of the second light source unit 120, a color temperature of multiplexed white light can be adjusted. Thus, according to the first embodiment, high-quality white light can be more uniformly used as radiation light in observation using white light (i.e., observation in the normal observation mode or the normal/special observation mode), and thus an observation image of higher quality can be obtained.

In addition, by appropriately controlling driving of the first light source unit 101 and the second light source unit 120 in the illumination device 10 according to the first embodiment as described above, the normal observation mode, the special observation mode, and the normal/special observation mode can be switched. As described above, switching of a wavelength band of radiation light and obtaining an observation image of higher quality can be simultaneously achieved according to the first embodiment.

Herein, in the configuration example described above, performance of the dichroic mirror 115 is adjusted so that the transmittance thereof with respect to light corresponding to the wavelength bands of laser light becomes about 90% as shown in FIG. 4, in order to improve use efficiency of laser light emitted from the second light source unit 120. The first embodiment, however, is not limited thereto. If a laser has extra power, for example, the transmittance of the dichroic mirror 115 with respect to light corresponding to the wavelength bands of laser light may be set to another value such as 50%. In addition, the transmittances of the dichroic mirror 115 with respect to light corresponding to the respective wavelength bands of the laser light may be set to different values.

In addition, although white light reflected by the dichroic mirror 115 is multiplexed with laser light that the dichroic mirror 115 has transmitted in the configuration example described above, the first embodiment is not limited thereto. The illumination device 10 may be configured such that, by setting reflection and transmission characteristics of the dichroic mirror 115 to be reversed with respect to the above-described characteristics, white light that the dichroic mirror 115 has transmitted and laser light reflected by the dichroic mirror 115 are multiplexed and the multiplexed light is incident on the light guide 130 via the condenser optical system 117.

In addition, the configuration shown in FIG. 1 is merely a configuration example of the illumination device 10, and a configuration of the illumination device 10 is not limited thereto. Various optical elements that can be mounted in an existing general illumination device may be further included in the illumination device 10. When a xenon lamp is used as a white light source of the first light source unit 101, for example, a filter that attenuates or removes light of a near-infrared band that can contribute to heating of a biological object during radiation or the like may be provided in the later stage of the first light source unit 101. Alternatively, a filter that attenuates or removes light of a near-infrared band or the like may be provided in the earlier stage of an image sensor used in observation of a subject. Alternatively, instead of providing such a filter, the function of the filter may be realized by the dichroic mirror 115. That is to say, the component of the near-infrared band may be attenuated or removed from white light emitted from the first light source unit 101 during multiplexing by adjusting the reflection characteristic or the transmission characteristic of the dichroic mirror 115.

1-2. Speckle Noise Reduction Effect

Figure 6A:
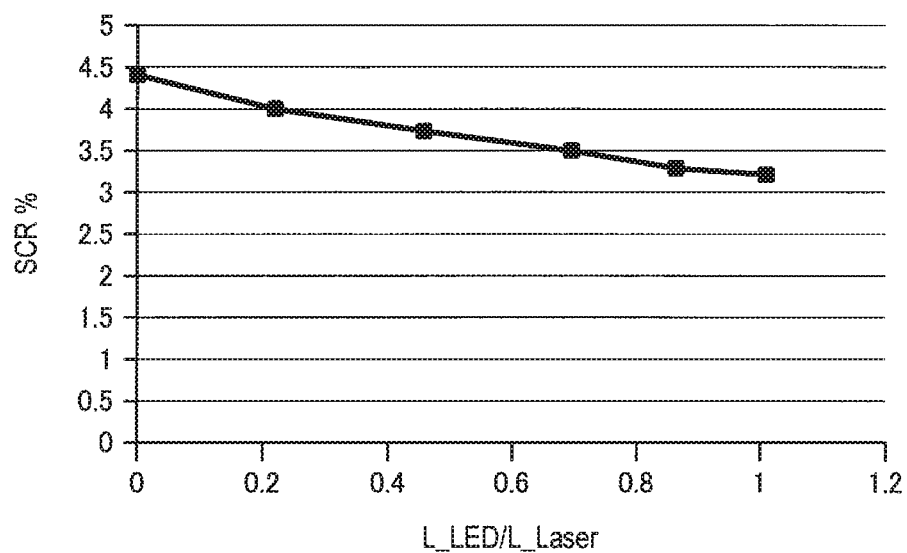
FIGS. 6(a) and 6(b) show diagrams illustrating a speckle noise reduction effect of the illumination device according to the first embodiment.
Figure 6B:
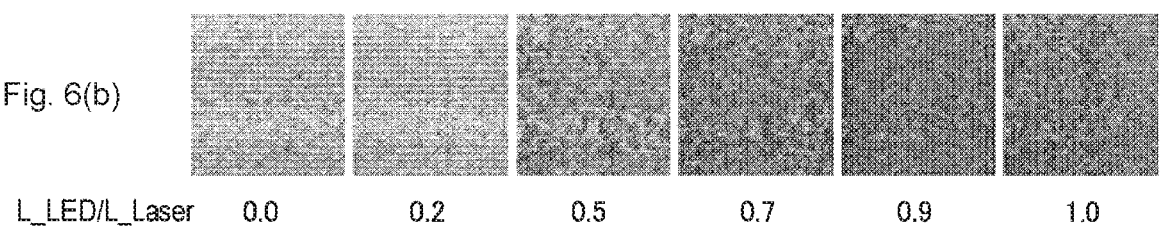

An experimental device configured the same as the illumination device 10 according to the first embodiment was prepared and, using the experimental device, speckle noise appearing when white light generated by multiplexing white light emitted from the first light source unit 101 and laser light emitted from the second light source unit 120 was radiated to an observation target was examined. The result is shown in FIGS. 6(a) and 6(b). FIGS. 6(a) and 6(b) include diagrams illustrating a speckle noise reduction effect of the illumination device 10 according to the first embodiment.

The horizontal axis of the graph shown in FIG. 6(a) represents a ratio of an output of the first light source unit 101 (L_LED) and an output of the second light source unit 120 (L_Laser) (L_LED/L_Laser). L_LED represents the total output of the white light source (white LED) included in the first light source unit 101, and L_Laser represents the total output of the laser light sources 121R, 121G and 121B included in the second light source unit 120. In addition, the vertical axis of the graph shown in FIG. 6(a) represents a speckle contrast ratio (SCR) which corresponds to a speckle amount in an observation image observed using multiplexed white light. On the other hand, FIG. 6(b) shows examples of an observation image observed using the multiplexed white light.

It is found from FIGS. 6(a) and 6(b) that the speckle amount changes according to the output ratio of the white light source and the laser light sources (L_LED/L_Laser) and the speckle amount decreases more when the output ratio is 1, i.e., the output of the white light source is substantially equal to the output of the laser light sources. It is ascertained from the result that speckle noise can be more reduced by adjusting an output ratio of the multiplexed white light source and laser light sources according to the first embodiment.

2. SECOND EMBODIMENT

Another configuration of an illumination device according to the second embodiment of the present disclosure will be described with reference to FIG. 7. FIG. 7 is a diagram illustrating a configuration example of the illumination device according to the second embodiment. Herein, the illumination device according to the second embodiment illustrated in FIG. 7 corresponds to the illumination device 10 according to the first embodiment illustrated in FIG. 1 described above from which the coupling optical system 105, the optical fiber 107, and the third collimator optical system 109 are omitted. Thus, in description regarding the second embodiment below, detailed description of overlapping points with the first embodiment will omitted and differences from the first embodiment will mainly be described.

Referring to FIG. 7, the illumination device 20 according to the second embodiment includes the first light source unit 101 which radiates white light, the first collimator optical system 103, the second light source unit 120 which includes at least one laser light source that emits light of a predetermined wavelength band, the diffusion member 111, the second collimator optical system 113, the dichroic mirror 115, and the condenser optical system 117. Here, since the configurations and functions of the respective members are the same as those of the respective members shown in FIG. 1, detailed description of the members will be omitted.

In the illumination device 20, white light emitted from the first light source unit 101 is converted into substantially parallel light by the first collimator optical system 103, and is incident on the dichroic mirror 115 as in the illumination device 10 according to the first embodiment. On the other hand, in the illumination device 20, laser light emitted from the second light source unit 120 is incident directly on the diffusion member 111, and diffused laser light (i.e., laser light from the secondary light source) is converted into substantially parallel light by the second collimator optical system 113 and is incident on the dichroic mirror 115, unlike in the illumination device 10 according to the first embodiment. As in the first embodiment, the effect of improved quality of multiplexed white light can be obtained and thus an observation image can have higher quality even in a more simplified configuration like the illumination device 20.

The configuration of the illumination device 20 according to the second embodiment has been described above with reference to FIG. 7. As described above, the same effect as in the first embodiment can be obtained in a more simplified configuration according to the second embodiment. Thus, in addition to the effect obtained in the first embodiment, miniaturization and reduction in a manufacturing cost of the illumination device 20 can be realized.

As described in (1-1. Configuration of an illumination device) above, there is the effect of more uniform luminance distribution of laser light emitted from the optical fiber 107 as the laser light is guided by the optical fiber 107. Thus, it is preferable to provide the optical fiber 107 as in the illumination device 10 according to the first embodiment in order to cause output light to have higher quality. Whether to employ the configuration of the illumination device 10 according to the first embodiment or to employ the configuration of the illumination device 20 according to the second embodiment may be appropriately decided by comprehensively taking quality of output light obtained according to applications, a manufacturing cost of a device, and the like into consideration.

3. MODIFIED EXAMPLES

A few modified examples of the first and second embodiments described above will be described. Note that, in description regarding the respective modified examples below, a case in which configurations corresponding to the respective modified examples are applied to the illumination device 10 of the first embodiment shown in FIG. 1 will be described as an example; however, the configurations corresponding to the respective modified examples can also be applied to the illumination device 20 of the second embodiment likewise.

3-1. Modified Example in which White Light and Laser Light are Multiplexed as Diverging Light A configuration of an illumination device in a modified example in which white light and laser light are multiplexed as diverging light will be described with reference to FIG. 8. FIG. 8 is a diagram illustrating a configuration example of the illumination device when white light and laser light are multiplexed as diverging light.

Herein, the illumination device according to the present modified example shown in FIG. 8 corresponds to the illumination device 10 according to the above-described first embodiment shown in FIG. 1 in which the optical characteristics of the first collimator optical system 103, the second collimator optical system 113, and the condenser optical system 117 are altered. Thus, in description regarding the present modified example below, detailed description of overlapping points with the first embodiment will be omitted, and differences from the first embodiment will mainly be described.

Referring to FIG. 8, the illumination device 30 according to the present modified example includes the first light source unit 101 which radiates white light, a first collimator optical system 103a, the second light source unit 120 which includes at least one laser light source that emits light of a predetermined wavelength band, the coupling optical system 105, the optical fiber 107, the third collimator optical system 109, the diffusion member 111, a second collimator optical system 113a, the dichroic mirror 115, and a condenser optical system 117a. Here, since the configurations and the functions of the first light source unit 101, the second light source unit 120, the coupling optical system 105, the optical fiber 107, the third collimator optical system 109, the diffusion member 111, and the dichroic mirror 115 are the same as those of the members shown in FIG. 1, detailed description of the respective members will be omitted.

In the present modified example, the first collimator optical system 103a causes white light emitted from the first light source unit 101 to be incident on the dichroic mirror 115 as diverging light rather than completely parallel light. The second collimator optical system 113a causes laser light emitted from the second light source unit 120 and diffused by the diffusion member 111 (i.e., laser light from the secondary light source) to be incident on the dichroic mirror 115 as diverging light rather than completely parallel light, along with the white light. The dichroic mirror 115 multiplexes the white light and the laser light, both of which are diverging light, and the multiplexed light is coupled to an end of the light guide 130 by the condenser optical system 117a. At this time, the condenser optical system 117a is configured to condense the light from the secondary light source on the incidence end face of the light guide 130 so that the light from the secondary light source fills the area of the incidence end of the light guide 130 as much as possible, as in the first embodiment.

Here, since it is generally necessary to increase a light emitting area of an LED in order to obtain high output, light emitted from an LED has a strong property of being isotropically discharged and does not easily become completely parallel light even when a collimator lens is used. Thus, when a white LED is used as the first light source unit 101 in the first embodiment, it is also difficult to convert white light from the first light source unit 101 into completely parallel light with the first collimator optical system 103. To overcome the difficulty of converting white light into completely parallel light described above, laser light is also set as diverging light along with the white light and both types of light are multiplexed as diverging light in the present embodiment. In light of this point, FIG. 8 can be said to more exactly illustrate the illumination device 30 as the configuration of the illumination device 10 when a white LED is used as the first light source unit 101 in the first embodiment.

In the present modified example, white light and laser light, both of which are set as diverging light, are multiplexed and the multiplexed light is coupled to the end of the light guide 130 by the condenser optical system 117a. That is to say, the first collimator optical system 103a and the condenser optical system 117a are a finite conjugate, as are the second collimator optical system 113a and the condenser optical system 117a. An optical characteristic of the condenser optical system 117a is appropriately designed such that multiplexed light is properly coupled to the incidence end face of the light guide 130 according to optical characteristics of the first collimator optical system 103a and the second collimator optical system 113a. Accordingly, in the illumination device 30 according to the present modified example, the effect of improving quality of multiplexed white light can be obtained and an observation image can be caused to have higher quality as in the first embodiment.

Note that, although each of the first collimator optical system 103a, the second collimator optical system 113a, and the condenser optical system 117a is illustrated as a convex lens for the sake of convenience in the example illustrated in FIG. 8, a detailed configuration of the optical systems is not limited thereto. The first collimator optical system 103a, the second collimator optical system 113a, and the condenser optical system 117a may each have the above-described functions, and may be configured to be appropriately combined with a known optical element.

The configuration of the illumination device 30 of the modified example in which white light and laser light are multiplexed both as diverging light has been described above. When a white LED is used as the first light source unit 101 and it is difficult to convert white light into completely parallel light as described above, for example, the illumination device 30 which exhibits the same effect as the first embodiment can be configured by appropriately adjusting the optical characteristics of the first collimator optical system 103a, the second collimator optical system 113a, and the condenser optical system 117a as in the present modified example.

3-2. Modified Example in which a Light Source of Another Wavelength Band is Added In the first and second embodiments described above, the case in which white light, red laser light, green laser light, and blue laser light are multiplexed has been described. In this configuration, red laser light, green laser light, blue laser light, or mixed light of any of the laser light is used as radiation light in the special observation mode. According to an observation purpose in the special observation mode, however, there can be a desire to use light of another wavelength band that is different from that of the laser light as radiation light. Herein, as a modified example of the first and second embodiments, a configuration of an illumination device in a case in which a light source of another wavelength band is added to the illumination device 10 according to the first embodiment will be described.

The configuration of the illumination device of the modified example to which a light source of another wavelength band is added will be described with reference to FIG. 9. FIG. 9 is a diagram illustrating a configuration example of the illumination device when a light source of another wavelength band is added thereto.

Here, the illumination device according to the present modified example illustrated in FIG. 9 corresponds to the illumination device 10 according to the above-described first embodiment shown in FIG. 1 to which a third light source unit 119 to be described below is added. Thus, in description regarding the present modified example below, detailed description regarding overlapping points with the first embodiment will be omitted and differences from the first embodiment will mainly be described.

Referring to FIG. 9, the illumination device 40 according to the present modified example includes the first light source unit 101 which radiates white light, the first collimator optical system 103, the second light source unit 120 which includes at least one laser light source that emits light of a predetermined wavelength band, the coupling optical system 105, the optical fiber 107, the third collimator optical system 109, the diffusion member 111, the second collimator optical system 113, the dichroic mirror 115, the condenser optical system 117, the third light source unit 119, and another dichroic mirror 125. Since configurations and functions of the respective members other than the third light source unit 119 and the dichroic mirror 125 are the same as the configurations and the functions of the members shown in FIG. 1, detailed description of those members will be omitted herein. In addition, the dichroic mirror 125 will be referred to also as a second dichroic mirror 125 in order to distinguish it from the dichroic mirror 115 for multiplexing white light and laser light.

As illustrated, the illumination device 40 according to the modified example is provided with the second dichroic mirror 125 in the middle of the optical path from the first light source unit 101 to the dichroic mirror 115. In addition, the third light source unit 119 is provided such that emitted light is incident on the second dichroic mirror 125 from the direction substantially perpendicular to the optical path from the first light source unit 101 to the dichroic mirror 115.

The third light source unit 119 emits light of a wavelength band that is different from that of laser light emitted from the second light source unit 120. Here, a case in which the third light source unit 119 is configured as an LED which emits ultraviolet light having the center wavelength of 410 nm will be described as an example. Note that, although not illustrated for the sake of simplification, a collimator lens or the like which causes light emitted from the third light source unit 119 to be substantially parallel light and to be incident on the second dichroic mirror 125 is provided in the later stage of the third light source unit 119.

The second dichroic mirror 125 has characteristics of transmitting white light emitted from the first light source unit 101 and reflecting ultraviolet light of around the wavelength of 410 nm emitted from the third light source unit 119. Accordingly, the second dichroic mirror 125 multiplexes white light and ultraviolet light, and the multiplexed light is incident on the dichroic mirror 115.

The dichroic mirror 115 has the same characteristic of transmitting light of a wavelength band corresponding to laser light from the second light source unit 120 as in the first embodiment. Thus, in the present modified example, light obtained by attenuating or removing a component of a wavelength band corresponding to laser light from the light which results from multiplexing of white light and ultraviolet light is reflected by the dichroic mirror 115 and the light is multiplexed with laser light. As described above, in the illumination device 40 according to the present modified example, light obtained by superimposing ultraviolet light on output light of the illumination device 10 according to the first embodiment can be output as multiplexed white light.

The configuration of the illumination device 40 of the modified example in which a light source of another wavelength band is added has been described above with reference to FIG. 9. According to the present modified example as described above, light obtained by superimposing emitted light from the third light source unit 119 on output light of the illumination device 10 according to the first embodiment can be output as multiplexed white light. Since the multiplexed white light is generated in the same manner as in the first embodiment except that the emitted light from the third light source unit 119 is added, the effect of improving quality of the multiplexed white light that is used as radiation light in the normal observation mode or the normal/special observation mode can be obtained and an observation image can be caused to have higher quality in the illumination device 40 according to the present modified example as in the first embodiment. On the other hand, in the special observation mode, by driving only the third light source unit 119, ultraviolet light can be radiated to an operative field according to an observation purpose. Since light of a wavelength band can be more properly output according to an observation purpose while realizing the effect obtained in the first embodiment in the present modified example as described above, the illumination device 40 which can correspond to greater diversity of applications is realized.

Here, when a light source of still another wavelength band is added, a configuration in which a laser light source is added to the second light source unit 120 can also be considered. For example, the same output light as that of the illumination device 40 can be obtained even if a laser light source that emits laser light of a wavelength band corresponding to ultraviolet light is added to the second light source unit 120 in the above-described example. A laser light source, however, generally tends to be more expensive than an LED and to be configured in a large size. By configuring the third light source unit 119 with an LED as in the illustrated configuration, the illumination device 40 can be realized with a lower cost in a smaller size.

Note that reflection and transmission characteristics of the second dichroic mirror 125 may be set to be reversed with respect to the above-described characteristics. In this case, ultraviolet light that the second dichroic mirror 125 transmits and white light reflected by the second dichroic mirror 125 are multiplexed and the multiplexed light is incident on the dichroic mirror 115. In addition, as in the first embodiment, reflection and transmission characteristics of the dichroic mirror 115 may be set to be reversed with respect to the above-described characteristics.

In addition, the second dichroic mirror 125 is an example of a multiplexing member for multiplexing white light and ultraviolet light, and multiplexing of white light and ultraviolet light may also be performed by a multiplexing member of another type, for example, a polarizing beam splitter, or the like.

In addition, the configurations according to the first and second embodiments and the respective modified examples described above may be combined with each other in a possible range. Herein, as described in (3-1. Modified example in which white light and laser light are multiplexed as diverging light), it is generally difficult to make emitted light from an LED into completely parallel light even if a collimator lens is used. Thus, in the configuration example illustrated in FIG. 9, when an LED is used as the first light source unit 101 and/or the third light source unit 119, emitted light from the units can be diverging light, rather than completely parallel light. Thus, when an LED is used as the first light source unit 101 and/or the third light source unit 119 in the configuration example illustrated in FIG. 9, it is preferable to appropriately adjust the optical characteristics of the first collimator optical system 103, the second collimator optical system 113, and the condenser optical system 117 in combination with the configuration example illustrated in FIG. 8 in order to deal with diverging light.

4. APPLICATION EXAMPLES

Application examples of the illumination devices 10, 20, 30, and 40 according to the first and second embodiments and the respective modified examples described above will be described. Herein, as an application example, a case in which the illumination devices 10, 20, 30, and 40 are applied to an observation device that can execute photodynamic diagnosis (PDD) and photodynamic therapy (PDT) will be described.

First, PDD and PDT will be described below. Then, an existing general observation device that can execute PDD and PDT will be described, and a disadvantage of such a general observation device will be described. Next, a configuration example and an operation example of an observation device to which the illumination device 10, 20, 30, and 40 are applied will be described.

(4-1. Regarding PDD and PDT)

PDD and PDT are for less invasive tumor diagnosis and medical treatment using photosensitive pharmaceutical agents, and have been applied to diagnosis and treatment of early liver cancer, early esophageal cancer, gastric cancer, early cervical cancer, cerebral malignancy, and the like.

In PDD, the property of a photosensitive pharmaceutical agent that emits fluorescence when it is excited by excitation light of a predetermined wavelength band is used. Since a photosensitive pharmaceutical agent administered to a patient has the property of accumulating in a tumor selectively, a tumor site can be diagnosed by radiating excitation light to an operative field and detecting fluorescence emitted from a photosensitive pharmaceutical agent.

In PDT, the property of a photosensitive pharmaceutical agent that generates active oxygen when it is irradiated with excitation light of a predetermined wavelength band is used. Since a photosensitive pharmaceutical agent administered to a patient has the property of accumulating in a tumor selectively as described above, a tumor site can be treated by radiating excitation light to an operative field to generate active oxygen mainly in the tumor site to cause degeneration of the tumor site and eventually cell death. Radiation of excitation light for performing PDD and PDT corresponds to an operation of the illumination device 10, 20, 30, or 40 in the special mode of the above-described embodiments.

When only excitation light is radiated to an operative field, a tumor site can be observed, but it is not possible to observe a normal state of the entire operative field. Thus, there is generally an observation device which can execute PDD and PDT having a function of switching or simultaneously performing radiation of white light for performing normal observation and radiation of excitation light for performing PDD and PDT.

For example, JP 2006-000157A (hereinafter referred to as Reference Literature 1) discloses a light source device for an observation device (endoscope device) that can switch radiation of white light for normal observation and radiation of laser light (excitation light) for fluorescence observation. In the technology described in Reference Literature 1, a dichroic mirror with a characteristic of transmitting white light emitted from a white light source and reflecting most excitation light from a laser light source guides white light and excitation light on the same optical axis. Then, by appropriately controlling movement of a shield plate provided in a later stage of the white light source and driving of the laser light source, the white light or the excitation light is incident on an end of a light guide. In this manner, the light source device described in Reference Literature 1 is configured to be able to switch to the normal observation mode and the special observation mode. Note that Reference Literature 1 is the same literature as PTL 9 described above.

For example, JP 2006-296516A (hereinafter referred to as Reference Literature 2) discloses an observation device (endoscope device) with which bright field observation is possible on a peripheral region of a lesion part emitting fluorescence by providing a white light source for normal observation near an intake of observation light (i.e., fluorescence) at the time of fluorescence observation. In the technology described in Reference Literature 2, the white light source that emits visible light which has an intensity of a wavelength band corresponding to fluorescence emitted from the lesion part relatively shorter than other wavelength bands or is cut by a filter is used as a light source provided in the intake of observation light, and thus the lesion part emitting fluorescence and the peripheral region thereof can be simultaneously observed. In this manner, the observation device described in Reference Literature 2 is configured to perform observation of an operative field in the normal/special observation mode.

For example, JP 2009-226067A (hereinafter referred to as Reference Literature 3) discloses an observation device having a white light source and a rotary filter in which a plurality of filters which each extract light of a predetermined wavelength band from white light emitted from the white light source are provided in different regions within a plane. In the technology described in Reference Literature 3, the rotary filter is provided with a first filter which extracts light from white light according to a wavelength band of excitation light which corresponds to a first photosensitive pharmaceutical agent, a second filter which extracts light from the white light corresponding to a wavelength band of excitation light which corresponds to a second photosensitive pharmaceutical agent, and a third filter which extracts light from the white light according to a wavelength band of visible light. In addition, radiation of excitation light and radiation of visible light are switched by controlling a rotation angle of the rotary filter and switching a filter through which white light passes. In this manner, the observation device disclosed in Reference Literature 3 is configured to switch to the normal observation mode and the special observation mode.

In the technology disclosed in Reference Literature 1, however, a use method of simultaneously radiating white light and excitation light (i.e., use method corresponding to the normal/special observation mode) is not assumed, and white light and excitation light are radiated in a time-sharing manner. Thus, it is necessary to provide a shield plate which shields white light as described above and a driving mechanism of the shield plate, and thus there is a possibility of a device becoming complicated and growing in size. In addition, in terms of a configuration of a device, white light which is incident on a light guide via a dichroic mirror is white light of which a wavelength component corresponding to excitation light is cut or attenuated and has a different hue from original white light, and thus there is concern of a high-quality observation image not being obtained at the time of normal observation. In addition, a light detector which detects an intensity of excitation light is provided in the light source device disclosed in Reference Literature 1 for the purpose of adjusting the output of a laser light source; however, since the light detector is configured such that white light can also reach the light detector, there is concern of a detection value of the light detector including an overlap of the intensity of excitation light and the intensity of white light, the output of the laser light source is not properly controlled, and therefore a high-quality observation image is not obtained at the time of fluorescence observation.

In addition, in the technology disclosed in Reference Literature 2, an optical path of white light for normal observation is different from an optical path of excitation light for fluorescence observation, and radiation angles of both types of light to an operative field are also different. Thus, a shadow appearing in an observation image due to the shape of an operative field can change between normal observation and fluorescence observation. Thus, there is a possibility of a situation in which, during fluorescence observation, a shadow is produced at a site at which a shadow is not found during normal observation. Since a portion in which a shadow is produced during fluorescence observation is one that excitation light does not reach, a portion set for fluorescence observation during normal observation is not observed during actual fluorescence observation, and thus there is concern of it being difficult to perform proper observation in response to a desire of a user.

In addition, in the technology disclosed in Reference Literature 3, a use method of simultaneously radiating white light and excitation light (i.e., a use method corresponding to the normal/special observation mode) is not assumed and white light and excitation light are radiated in a time-sharing manner as in the technology disclosed in Reference Literature 1. Although radiation of white light or excitation light is realized in a time-sharing manner using a rotary filter in the technology disclosed in Reference Literature 3 as described above, the rotary filter and a driving mechanism of the rotary filter are necessary, and thus there is a possibility of a device becoming complicated and growing in size.

As described above, in the existing general technologies, a configuration in which normal observation and/or fluorescence observation are executed in a simpler way and an observation image of higher quality can be acquired in normal observation and/or fluorescence observation was not sufficiently examined. On the other hand, according to an embodiment of the present disclosure, execution of normal observation and/or fluorescence observation with a simpler configuration and obtaining an observation image of higher quality in normal observation and/or fluorescence observation can be simultaneously achieved by applying the illumination devices 10, 20, 30, and 40 according to the first and second embodiments and the respective modified examples described above to an observation device. Configuration examples of observation devices to which the illumination devices 10, 20, 30, and 40 are applied will be described in detail below.

4-2. Endoscope Device 4-2-1. Configuration of an Endoscope Device

A configuration of an endoscope device to which the illumination devices 10, 20, 30, and 40 are applied will be described with reference to FIGS. 10 to 12. FIG. 10 is a diagram illustrating a configuration example of the endoscope device to which the illumination devices 10, 20, 30, and 40 according to the first and second embodiments and the respective modified examples are applied. FIGS. 11 and 12 are graphs for describing a characteristic of a dichroic mirror of the endoscope device illustrated in FIG. 10.

Note that, in description below, a case in which the configuration corresponding to the illumination device 20 according to the second embodiment is mounted in the endoscope device will be described as an example. The present application example, however, is not limited thereto, and configurations corresponding to other illumination devices 10, 30, and 40 may be mounted in the endoscope device.

Referring to FIG. 10, the endoscope device 1 includes an illumination device 1100, an endoscope unit 1200, an image processing device 1300, and a display device 1400. Note that, in FIG. 10, an observation site 1500 to which output light from the illumination device 1100 is radiated is also schematically illustrated.

Illumination Device 1100

The illumination device 1100 generates white light (multiplexed white light) for normal observation and excitation light for fluorescence observation. Multiplexed white light and/or excitation light generated by the illumination device 1100 are incident on the light guide 130, guided into a lens barrel 1210 to be described below by the light guide 130, and then radiated to the observation site 1500 from the front end of the lens barrel 1210.

Here, the illumination device 1100 corresponds to the illumination device 20 according to the above-described second embodiment. Several members, however, are added to illumination device when it is mounted in the endoscope device 1.

Specifically, the illumination device 1100 includes the first light source unit 101 which radiates white light, the first collimator optical system 103, a second light source unit 120b which includes at least one laser light source that emits light of a predetermined wavelength band, the diffusion member 111, the second collimator optical system 113, a dichroic mirror 115b, the condenser optical system 117, a laser line filter 1101, a half mirror 1103, a light detector 1105, another half mirror 1107, another light detector 1109, and a control unit 1120.

As described above, the illumination device 1100 corresponds to the illumination device 20 according to the second embodiment to which the laser line filter 1101, the half mirror 1103, the light detector 1105, the half mirror 1107, and the light detector 1109 are added, and in which the optical characteristics of the second light source unit 120 and the dichroic mirror 115 have been altered. Since the configurations and functions of other members are the same as those of the respective members shown in FIG. 7, detailed description of the respective members is omitted. In addition, the control unit 1120 corresponds to the control unit which controls driving of the first light source unit 101 and the second light source unit 120, not illustrated in FIG. 7.

Here, the second light source unit 120b corresponds to the second light source unit 120 of the illumination device 20 of which emissive laser light has an altered wavelength band, and the dichroic mirror 115b corresponds to the dichroic mirror 115 of the illumination device 20 of which the reflection and transmission characteristics are altered. Since other configurations and functions of the second light source unit 120b and the dichroic mirror 115b are the same as those of the members of the illumination device 20, overlapping points with regard to the second light source unit 120b and the dichroic mirror 115b described above will not be described in detail.

Note that, although illustration of the second light source unit 120b is simplified in FIG. 10, the second light source unit 120b includes at least one laser light source, the same as the second light source unit 120 illustrated in FIG. 7. As at least one laser light source included in the second light source unit 120b, however, one that can emit laser light of a wavelength band that is used as excitation light in PDD and PDT is mounted.

The laser line filter 1101 is provided between, for example, the third collimator optical system 109 and the diffusion member 111 as illustrated. The laser line filter 1101 is a so-called band-pass filter (BPF) which only transmits light of wavelength bands other than a predetermined wavelength band. The laser line filter 1101 is set to remove the spectrum except for a laser oscillation wavelength (for example, a natural emission light component of a laser light source included in the second light source unit 120b or the like). When laser light emitted from the second light source unit 120b passes through the laser line filter 1101, a component of an extra wavelength band which can be noise in an observation image is removed from the laser light, and only a component of a wavelength band corresponding to excitation light is extracted from the laser light.

The half mirror 1103 is provided in the later stage of the laser line Part of laser light demultiplexed by the half mirror 1103 is incident on the light detector 1105. The light detector 1105 has a function of detecting an intensity of light, and the value of detection is provided to a second-light-source-unit driving control unit 1123 of the control unit 1120 to be described below. The second-light-source-unit driving control unit 1123 controls driving of each laser light source of the second light source unit 120b based on the detection value so that, for example, a total output of laser light from the second light source unit 120b becomes constant. By providing the configuration for monitoring the output of laser light emitted from the second light source unit 120b as described above, the output can be set to be more stable.

The half mirror 1107 is provided on the optical path from the first light source unit 101 to the dichroic mirror 115b. Part of white light demultiplexed by the half mirror 1107 is incident on the light detector 1109. The light detector 1109 has a function of detecting an intensity of light, and the value of the detection is provided to a first-light-source-unit driving control unit 1121 of the control unit 1120 to be described below. The first-light-source-unit driving control unit 1121 controls driving of the white light source of the first light source unit 101 based on the detection value so that, for example, the output of white light from the first light source unit 101 becomes constant. By providing the configuration for monitoring the output of white light from the first light source unit 101 as described above, the output can be set to be more stable.

Note that the half mirrors 1103 and 1107 are an example of a demultiplexing member, and other demultiplexing members may be used in place of the half mirrors 1103 and 1107. In addition, as the light detectors 1105 and 1109, various known light detectors may be used.

The control unit 1120 comprehensively controls operations of the illumination device 1100. The control unit 1120 includes the first-light-source-unit driving control unit 1121 and the second-light-source-unit driving control unit 1123 as its functions. The control unit 1120 includes a processor, for example, a central processing unit (CPU), a digital signal processor (DSP), or the like, a microcomputer in which such a processor is mounted, and the like, and each of the functions of the control unit 1120 is realized when the processor executes an arithmetic operation process according to a predetermined program.

The first-light-source-unit driving control unit 1121 controls the output of light emission of the first light source unit 101. Specifically, the first-light-source-unit driving control unit 1121 can control the output of light emission by changing a driving current of the white light source (for example, a white LED) of the first light source unit 101. As described above, the first-light-source-unit driving control unit 1121 can monitor an intensity of white light based on a detection value of the light detector 1109 and can control driving of the first light source unit 101 so that the intensity of white light becomes constant.

The second-light-source-unit driving control unit 1123 controls the output of light emission of the second light source unit 120b. Specifically, the second-light-source-unit driving control unit 1123 can control the output of light emission by changing a driving current of the laser light source of the second light source unit 120b. As described above, the second-light-source-unit driving control unit 1123 can monitor an intensity of laser light based on a detection value of the light detector 1105 and control driving of the second light source unit 120b so that the intensity of laser light becomes constant.

In addition, the second-light-source-unit driving control unit 1123 may further have a function of controlling an oscillation wavelength of the laser light source to be constantly maintained by constantly maintaining a device temperature of the laser light source of the second light source unit 120b. For example, the device temperature of the laser light source can be constantly maintained by a thermoelectric cooler and a temperature-measuring element included in the laser light source, in which the second-light-source-unit driving control unit 1123 controls driving of the thermoelectric cooler based on temperature measurement information by the temperature-measuring element.

Examples of excitation light wavelengths and fluorescence wavelengths of photosensitive pharmaceutical agents used in PDD and PDT are shown in Table 2 below.

TABLE 2

| Pharmaceutical agent | Excitation light wavelength | Fluorescence wavelength |
| --- | --- | --- |
| 5-ALA | 405 nm | 635 nm |
| Laserphyrin | 664 nm | 672 nm |

In the present configuration example, the second light source unit 120b is configured to emit laser light corresponding to the excitation light wavelength of a photosensitive pharmaceutical agent to be used. In addition, the dichroic mirror 115b is configured to attenuate or cut light corresponding to the excitation light wavelength of the photosensitive pharmaceutical agent to be used from white light emitted from the first light source unit 101 and to have a characteristic of transmitting laser light (i.e., light corresponding to the excitation light wavelength of the photosensitive pharmaceutical agent to be used) emitted from the second light source unit 120.

A configuration and an operation of the endoscope device 1 when Laserphyrin is used as a photosensitive pharmaceutical agent will be described below as an example. In addition, the second light source unit 120b multiplexes and emits laser light of three different wavelength bands in the configuration example described in (2. Second embodiment) described above; however, in order to simplify description, the second light source unit 120b will be described as only emitting laser light of a wavelength band corresponding to the excitation light wavelength of Laserphyrin. This corresponds to a state in which, among a plurality of laser light sources included in the second light source unit 120b, only a laser light source that can emit laser light corresponding to the excitation light wavelength of Laserphyrin is driven.

The characteristic of the dichroic mirror 115b when Laserphyrin is used as a photosensitive pharmaceutical agent will be described with reference to FIGS. 11 and 12. In FIG. 11, the spectrum of white light emitted from the first light source unit 101, the spectrum of laser light emitted from the second light source unit 120b, and the transmission characteristics of the dichroic mirror 115b are shown in the same graph.

As shown, the white light emitted from the first light source unit 101 has a wide-band light emission spectrum including the wavelength bands of approximately 400 nm to 750 nm. On the other hand, the laser light emitted from the second light source unit 120b has a narrow-band light emission spectrum in which the oscillation peak wavelength corresponds to the excitation light wavelength of Laserphyrin (664 nm).

In addition, the dichroic mirror 115b has a band-pass characteristic of transmitting light of a wavelength band of about dozens of nm around the excitation light wavelength (i.e., the peak wavelength of laser light from the second light source unit 120b). In the illustrated example, the dichroic mirror 115b has a characteristic of transmitting light of a wavelength band of about 20 nm around the excitation light wavelength of Laserphyrin (664 nm).

FIG. 12 shows the spectrum of light multiplexed by the dichroic mirror 115b. As illustrated, white light emitted from the first light source unit 101 has components attenuated at bandwidths of about 20 nm around 664 nm that is the excitation light wavelength of Laserphyrin, and thus has a shape of a broadband spectrum divided into two from about 400 nm to 654 nm and about 674 nm to 750 nm. On the other hand, with respect to laser light emitted from the second light source unit 120b, the spectrum shape formed after the laser light has passed through the laser line filter 1101 is maintained. Light obtained after the dichroic mirror 115b multiplexes the white light emitted from the first light source unit 101 and the laser light emitted from the second light source unit 120b has the spectrum in which the spectrums thereof overlap with each other. That is to say, the multiplexed light can be said to be white light (i.e., multiplexed white light) generated by attenuating the component of the wavelength band corresponding to the excitation light wavelength of Laserphyrin from the white light emitted from the first light source unit 101 and complementing the attenuated component with the laser light emitted from the second light source unit 120b.

Endoscope Unit 1200

The endoscope unit 1200 includes the lens barrel 1210 and an imaging unit 1220. In the present configuration example, the endoscope unit 1200 is configured as a rigid endoscope. The lens barrel 1210 has a substantially cylindrical shape, in which the light guide 130 (i.e., a light guiding member) extends to the front end thereof. When the lens barrel 1210 is inserted into the body cavity of a patient and light guided through the light guide 130 (i.e., output light from the illumination device 1100) is radiated thereto from the front end part, the white light and/or excitation light is radiated to the observation site 1500.

When the white light and/or excitation light is radiated to the observation site 1500, reflected light in the reverse direction is guided inside the lens barrel 1210 in the reverse direction, and then reaches the imaging unit 1220. In FIG. 10, propagation of the light in the imaging unit 1220 is schematically illustrated with dashed-line arrows.

The imaging unit 1220 includes an optical filter 1221, a first image sensor 1223, and a second image sensor 1225. Upon reaching the imaging unit 1220, the reflected light from the observation site 1500 is incident on the optical filter 1221.

The optical filter 1221 is a spectroscopic element such as a dichroic mirror, and is configured to transmit light of a wavelength of, for example, 670 nm or longer and cause the light to be incident on the first image sensor 1223, and to reflect light of a wavelength band shorter than 670 nm and cause the light to be incident on the second image sensor 1225. Thus, the first image sensor 1223 does not receive excitation light of Laserphyrin (the wavelength of 664 nm), but receives fluorescence of Laserphyrin (the wavelength of 672 nm). In this manner, the optical filter 1221 is configured to cause only fluorescence of a pharmaceutical agent among excitation light of the pharmaceutical agent and fluorescence of the pharmaceutical agent to be incident on one image sensor (the first image sensor 1223 in the illustrated example).

The first image sensor 1223 and the second image sensor 1225 are image sensors with which color imaging is possible. Although types of the first image sensor 1223 and the second image sensor 1225 are not limited, various known image sensors, for example, a charge coupled device (CCD) image sensor, a complementary metal-oxide-semiconductor (CMOS) image sensor, and the like can be used as the first image sensor 1223 and the second image sensor 1225.

The output of the first image sensor 1223 is input to a long-wavelength band image generation unit 1301 of the image processing device 1300 to be described later. In addition, the output of the second image sensor 1225 is input to a short-wavelength band image generation unit 1303 of the image processing device 1300 to be described later.

Image Processing Device 1300

The image processing device 1300 generates a captured image (observation image) of the observation site 1500 based on reflected light from the observation site 1500 detected by the imaging unit 1220. The image processing device 1300 includes the long-wavelength band image generation unit 1301, the short-wavelength band image generation unit 1303, and an observation image generation unit 1305, and an input unit 1307 as its functions. The image processing device 1300 includes a processor, for example, a CPU or a DSP, a microcomputer in which such a processor is mounted, or the like, and each function of the image processing device 1300 is realized as the processor executes an arithmetic operation process according to a predetermined program. For example, the image processing device 1300 may be an information processing device such as a personal computer (PC) in which a processor or a microcomputer is mounted.

The long-wavelength band image generation unit 1301 generates an image of the observation site 1500 based on an output signal from the first image sensor 1223. The image generated by the long-wavelength band image generation unit 1301 is hereinafter also referred to as a first image. Since the first image sensor 1223 receives light of a wavelength of 670 nm or longer using the optical filter 1221, the long-wavelength band image generation unit 1301 generates the first image based on light of a relatively long wavelength band of which the wavelength is 670 nm or longer. In this manner, the long-wavelength band image generation unit 1301 generates the first image based on light of a wavelength band that is a longer wavelength band than the excitation light wavelength including the fluorescence wavelength.

The short-wavelength band image generation unit 1303 generates an image of the observation site 1500 based on an output signal from the second image sensor 1225. The image generated by the short-wavelength band image generation unit 1303 is hereinafter also referred to as a second image. Since the second image sensor 1225 receives light of a wavelength shorter than 670 nm using the optical filter 1221, the short-wavelength band image generation unit 1303 generates the second image based on light of a relatively short wavelength band of which the wavelength is shorter than 670 nm. In this manner, the short-wavelength band image generation unit 1303 generates the second image based on light of a wavelength band that is a shorter wavelength band than the fluorescence wavelength including the excitation light wavelength.

The observation image generation unit 1305 generates an observation image based on at least any of the first image generated by the long-wavelength band image generation unit 1301 and the second image generated by the short-wavelength band image generation unit 1303. The image generated by the observation image generation unit 1305 becomes the observation image of the observation site 1500 that is finally visible to a user. Here, specific processes of the observation image generation unit 1305 differ according to observation modes. Details of the processes of the observation image generation unit 1305 will be described again in (4-2-2. Operation of the endoscope device) below. The observation image generation unit 1305 transmits information regarding the generated image to a display device 1400.

The input unit 1307 is an input interface that receives operation inputs of the user. The input unit 1307 is configured with an input device operated by the user, for example, a mouse, a keyboard, a touch panel, a button, a switch, a lever, or the like. The user can input various kinds of information and various instructions to the endoscope device 1 via the input unit 1307.

For example, the user can input an instruction to select any of the normal observation mode, the special observation mode, and the normal/special observation mode as an observation mode to the endoscope device 1 via the input unit 1307. Information regarding the selected observation mode is input to the observation image generation unit 1305 and the first-light-source-unit driving control unit 1121 and the second-light-source-unit driving control unit 1123 of the illumination device 1100, and the observation image generation unit 1305, the first-light-source-unit driving control unit 1121, and the second-light-source-unit driving control unit 1123 generate an image or drive the first light source unit 101 and the second light source unit 120b according to the selected observation mode.

In addition, for example, the user can input an instruction regarding intensity of emitted light from the first light source unit 101 and the second light source unit 120b of the illumination device 1100 to the endoscope device 1 via the input unit 1307. Information regarding the input intensity is input to the first-light-source-unit driving control unit 1121 and the second-light-source-unit driving control unit 1123 of the illumination device 1100, and the first-light-source-unit driving control unit 1121 and the second-light-source-unit driving control unit 1123 drive the first light source unit 101 and the second light source unit 120b so that the instructed intensity is realized.

Display Device 1400

The display device 1400 displays images generated by the observation image generation unit 1305 of the image processing device 1300. A type of the display device 1400 is not limited, and the display device 1400 may be, for example, a CRT display device, a liquid crystal display device, a plasma display device, an EL display device, or the like. The user performs diagnosis or treatment of the observation site 1500 by visually recognizing an image displayed on the display device 1400.

The configuration example of the endoscope device 1 to which the illumination device 20 is applied has been described above with reference to FIGS. 10 to 12. Note that the configuration of the endoscope device 1 illustrated in FIG. 10 is merely an example, and a detailed configuration of the endoscope device 1 may be appropriately modified within the scope in which the above-described functions are realized. For example, the endoscope device 1 may be further provided with various optical elements included in an existing general endoscope device in addition to the illustrated configuration.

In addition, the functions of the control unit 1120 of the illumination device 1100 and the functions of the image processing device 1300 may not necessarily be provided in each device as illustrated, and the functions may be executed by either device. For example, some or all of the functions of the control unit 1120 may be provided in the image processing device 1300. Alternatively, some or all of the functions of the image processing device 1300 may be provided in the illumination device 1100. In addition, an input of an instruction regarding driving of the illumination device 1100 is performed via the input unit 1307 provided in the image processing device 1300 in the above-described example; however, the same function as the input unit 1307 may be provided in the illumination device 1100 and the user may input various instructions to the illumination device 1100 via the input unit.

4-2-2. Operations of the Endoscope Device

Operations of the endoscope device 1 according to observation modes mentioned above will be described. In the endoscope device 1, any of the normal observation mode, the special observation mode, and the normal/special observation mode can be selected as an observation mode.

Normal Observation Mode

In the normal observation mode, light of a broadband corresponding to visible light in the range of approximately 400 nm to 750 nm is radiated to the observation site 1500 and an image of the observation site 1500 is acquired. When the user inputs an instruction to select the normal observation mode as an observation mode via the input unit 1307, the first-light-source-unit driving control unit 1121 and the second-light-source-unit driving control unit 1123 of the illumination device 1100 drive the first light source unit 101 and the second light source unit 120b together according to the instruction.

At this moment, output light from the illumination device 1100 becomes light generated by multiplexing white light from the first light source unit 101 and laser light from the second light source unit 120b (multiplexed white light) as illustrated in FIG. 12. Here, in the normal observation mode, the output of the laser light from the second light source unit 120b can be appropriately adjusted so that the multiplexed white light has a similar hue to the original white light emitted from the first light source unit 101. That is to say, the output of the laser light can be adjusted so that the component of the wavelength band attenuated or removed by the dichroic mirror 115b is complemented by the laser light from the second light source unit 120b to reproduce the original white light.

In the imaging unit 1220, light of a wavelength of 670 nm or longer is incident on the first image sensor 1223 and light of a wavelength shorter than 670 nm is incident on the second image sensor 1225 as described above. Thus, the long-wavelength band image generation unit 1301 of the image processing device 1300 generates an image as the first image based on light of a red band with a wavelength of 670 nm or longer. In addition, the short-wavelength band image generation unit 1303 generates an image as the second image based on light of a red band, a green band, and a blue band with a wavelength shorter than 670 nm.

In the normal observation mode, the observation image generation unit 1305 generates a combined image by summing up the RGB values of the first image generated by the long-wavelength band image generation unit 1301 and the RGB values of the second image generated by the short-wavelength band image generation unit 1303. The combined image generated in this way is a normal observation image corresponding to radiation light of a visible light band (about 400 nm to 750 nm).

Note that, although the case in which the first light source unit 101 and the second light source unit 120b are driven together in the normal observation mode has been described in the example described above, an operation of the endoscope device 1 in the normal observation mode is not limited thereto. For example, as long as white light from which light of a wavelength band near 664 nm that is a wavelength corresponding to excitation light of Laserphyrin has been removed or reduced by the dichroic mirror 115b does not cause trouble with observation of the observation site 1500, only the first light source unit 101 may be driven.

In addition, although the case in which the output of the laser light from the second light source unit 120b is adjusted so that the multiplexed white light has a similar hue to the original white light emitted from the first light source unit 101 has been described in the above-described example, an operation of the endoscope device 1 in the normal observation mode is not limited thereto. For example, by appropriately adjusting the output of white light from the first light source unit 101 and the output of laser light from the second light source unit 120b, multiplexed white light may be adjusted in a possible range so that the light has a predetermined hue set in advance by a user (for example, a similar hue to white light from various standard illuminants). In addition, for example, the second light source unit 120b may be configured to be capable of emitting red laser light, green laser light, and blue laser light which correspond to the three primary colors of light in addition to laser light of the wavelength band which corresponds to the excitation light wavelength of Laserphyrin, like the second light source unit 120 of the illumination devices 10, 20, 30, and 40. In this case, by appropriately controlling the output of the laser light of each color, the color temperature of the multiplexed white light can be adjusted so that the hue of white light from any of various light sources is reproduced. Note that such adjustment of color temperature of multiplexed white light using red laser light, green laser light, and blue laser light may also be performed in the normal/special observation mode to be described below.

Special Observation Mode

In the special observation mode, narrow-band light corresponding to the excitation light wavelength of Laserphyrin that is a photosensitive pharmaceutical agent is radiated to the observation site 1500 and an image based on fluorescence from the observation site 1500 is acquired. The special observation mode is an observation mode used when PDD and PDT are performed.

When a user inputs an instruction to select the special observation mode as an observation mode via the input unit 1307, only the second light source unit 120b is driven by the second-light-source-unit driving control unit 1123 of the illumination device 1100 according to the instruction.

At this time, the output light from the illumination device 1100 is light without the spectrum of white light in the spectrum shown in FIG. 12, i.e., laser light having the excitation light wavelength of Laserphyrin as the center wavelength. Note that, generally in PDT, excitation light with a stronger intensity is radiated to the observation site 1500 than in PDD. Thus, when PDT is performed in the special observation mode, the output of laser light from the second light source unit 120b is set to be stronger than when PDD is performed.

In the imaging unit 1220, light having a wavelength of 670 nm or longer is incident on the first image sensor 1223 and light having a wavelength shorter than 670 nm is incident on the second image sensor 1225 as described above. Thus, the long-wavelength band image generation unit 1301 of the image processing device 1300 generates an image based on light in a red band with a wavelength of 670 nm or longer as the first image.

Here, since the fluorescence wavelength of Laserphyrin is 672 nm, the first image generated by the long-wavelength band image generation unit 1301 is an image based on fluorescence of Laserphyrin, i.e., an image in which a tumor that is an observation target in the special observation mode is selectively visible. Thus, in the special observation mode, the observation image generation unit 1305 outputs the first image generated by the long-wavelength band image generation unit 1301, i.e., the fluorescence observation image to the display device 1400.

Normal/Special Observation Mode

In the normal/special observation mode, by simultaneously performing radiation of white light for normal observation and radiation of excitation light for special observation, recognition of the shape of an operative field based on a normal observation image and fluorescence observation of a tumor based on a special observation image can be simultaneously performed. In this manner, by performing observation in the normal/special observation mode, the position of a tumor in an operative field can be easily determined.

When a user inputs an instruction to select the normal/special observation mode as an observation mode through the input unit 1307, the first-light-source-unit driving control unit 1121 and the second-light-source-unit driving control unit 1123 of the illumination device 1100 drive the first light source unit 101 and the second light source unit 120b together according to the instruction. At this time, the output light from the illumination device 1100 is light generated by multiplexing the white light from the first light source unit 101 and laser light from the second light source unit 120b (multiplexed white light) as shown in FIG. 12. Unlike in the normal observation mode, however, the output of the laser light from the second light source unit 120b is adjusted to a value according to PDD and PDT in the normal/special observation mode. Note that, in this case, when PDT is performed, the output of laser light from the second light source unit 120b is set to be stronger than when PDD is performed, like in the special observation mode.

In the imaging unit 1220, light of a wavelength of 670 nm or longer is incident on the first image sensor 1223 and light of a wavelength shorter than 670 nm is incident on the second image sensor 1225 as described above. Thus, the long-wavelength band image generation unit 1301 of the image processing device 1300 generates an image as the first image based on light of a red band with a wavelength of 670 nm or longer. In addition, the short-wavelength band image generation unit 1303 generates an image as the second image based on light of a red band, a green band, and a blue band with a wavelength shorter than 670 nm.

Here, since the fluorescence wavelength of Laserphyrin is 672 nm, the first image generated by the long-wavelength band image generation unit 1301 is an image based on fluorescence of Laserphyrin, i.e., an image in which a tumor is selectively visible. On the other hand, a red component of the second image generated by the short-wavelength band image generation unit 1303 is considered to be based on a component corresponding to the excitation light wavelength of Laserphyrin of radiation light. The red component of the second image can be said to be a component that hinders fluorescence observation of a tumor.

Thus, the observation image generation unit 1305 generates a combined image in the normal/special observation mode by summing up an R value of the first image generated by the long-wavelength band image generation unit 1301 and GB values of the second image generated by the short-wavelength band image generation unit 1303. The combined image generated in this manner is an image in which a normal observation image based on the GB values of the second image and a fluorescence observation image based on the R value of the first image overlap. In the image, a tumor is displayed in red in the normal observation image based on the GB values.

Note that, although the case in which the first light source unit 101 and the second light source unit 120*b* are driven together in the normal/special observation mode has been described in the above-described example, an operation of the endoscope device 1 in the normal/special observation mode is not limited thereto. For example, by alternately executing an operation in the normal observation mode and an operation in the special observation mode described above continuously in a time sharing manner to obtain a normal observation image and a fluorescence observation image and combining the images using the observation image generation unit 1305, an image in which the normal observation image and the fluorescence observation image overlap may be acquired.

In addition, in the finally obtained image of the above-described example, a tumor can be displayed in red in the normal observation image based on the GB values. The tumor displayed in red, however, is not necessarily easily visible to the user. Thus, based on a desire of the user, another image process may be performed by the observation image generation unit 1305 to appropriately change a display color of a tumor. Accordingly, visibility of a tumor for the user can be further improved.

The configuration and the operation of the endoscope device 1 with which the illumination device 1100 having substantially the same configuration as the illumination device 20 according to the second embodiment is incorporated have been described above. As the illumination device 1100 is used as a light source of the endoscope device 1, the following effect can be obtained as the illumination device 20.

That is to say, in the illumination device 1100, the diffusion member 111 is provided on the optical path of laser light from the second light source unit 120*b* and a radiation angle of laser light increases due to the diffusion member 111. A white LED generally used in the first light source unit 101 has a greater beam diameter and radiation angle than the laser light source (for example, semiconductor laser) used in the second light source unit 120*b*. Thus, by causing a radiation angle of laser light from the second light source unit 120*b* to increase using the diffusion member 111, white light from the first light source unit 101 and laser light from the second light source unit 120*b* can be ensured to have substantially the same beam diameter and incidence angle on the incidence end face of the light guide 130, i.e., the beam diameter and the radiation angle on the output end of the light guide 130 can be substantially the same. Thus, luminance distribution of radiation light on the observation site 1500 can be substantially the same and color unevenness or the like of the radiation light can be reduced.

In addition, in the illumination device 1100, the condenser optical system 117 is configured to cause light from the secondary light source to form an image such that the light fills the area of the incidence end of the light guide 130. Accordingly, speckle noise can be reduced for the entire illumination device 1100. Thus, an observation image of higher quality with reduced speckle noise can be obtained.

Furthermore, the endoscope device 1 can obtain the following effect.

In the illumination device 1100, white light from the first light source unit 101 and laser light from the second light source unit 120*b* are multiplexed on the same optical axis. Hence, shadows produced due to undulation of the observation site 1500 are observed in the same shape when white light from the first light source unit 101 is used as radiation light and when laser light from the second light source unit 120*b* is used as radiation light. Thus, in a portion in which no shadow is produced during normal observation, a shadow is produced during fluorescence observation, and thus a situation in which it is not possible to radiate excitation light to that portion does not occur. Therefore, a user can smoothly perform a series of operations of radiating in the special observation mode excitation light to a spot targeted in the normal observation mode, and user convenience can be improved.

In addition, in the illumination device 1100, the first light source unit 101 is configured with, for example, a white LED and the second light source unit 120*b* is configured with, for example, a semiconductor laser. When the first light source unit 101 and the second light source unit 120*b* are configured with semiconductor light emission elements as above, the output of emitted light from each of the light source units can be independently controlled at an arbitrary timing by appropriately controlling their driving currents. Thus, the output light from the illumination device 1100 can be adjusted at a higher degree of freedom.

Note that, although the case in which the second light source unit 120*b* only emits laser light of the wavelength band corresponding to the excitation light wavelength of the photosensitive pharmaceutical agent has been described in the above-described application example for the sake of simplicity, the second light source unit 120*b* of the illumination device 1100 may also emit laser light of a plurality of different wavelength bands as that of the illumination devices 10, 20, 30, and 40. When the second light source unit 120*b* is configured in this manner, the color temperature of multiplexed white light used as radiation light in the normal observation mode and the normal/special observation mode can be easily adjusted by controlling the outputs of the laser light independently of each other.

In addition, the illumination device 1100 is provided with the light detectors 1105 and 1109 for respectively detecting intensities of white light from the first light source unit 101 and laser light from the second light source unit 120*b* before multiplexing. Then, according to the intensities of the white light and the laser light monitored by the light detectors 1105 and 1109, driving of the first light source unit 101 and the second light source unit 120*b* is controlled. Thus, the intensities of the emitted light from the first light source unit 101 and the second light source unit 120*b* can be controlled with high accuracy, and quality of the output light from the illumination device 1100 can be further improved.

In addition, in the illumination device 1100, the dichroic mirror 115*b* attenuates or removes light of a predetermined wavelength band from the white light from the first light source unit 101 and multiplexes the white light with the laser light from the second light source unit 120*b* so that the attenuated or removed component of the wavelength band is complemented. In addition, in this case, the output of the laser light from the second light source unit 120*b* can be appropriately adjusted so that the multiplexed light has a similar hue to the original white light. Thus, a change in the hue of the observation site 1500 sensed by the user can be suppressed to a minimum level when the multiplexed white light is used for observation in the normal observation mode and the normal/special observation mode.

In addition, in the endoscope device 1, the imaging unit 1220 is configured such that light of the wavelength band corresponding to excitation light is not incident but light of the wavelength band corresponding to fluorescence is incident on the first image sensor 1223 by the optical filter 1221 in the special observation mode and the normal/special observation mode. In this manner, according to the present application example, with the relatively simple configuration of the optical filter 1221, a weak fluorescence component emitted from the observation site 1500 can be detected with high accuracy and thus a high-definition fluorescence observation image can be obtained.

In addition, as processes by the observation image generation unit 1305 are appropriately switched according to observation modes in the endoscope device 1, identification of an operative field based on a normal observation image in the normal observation mode, diagnosis of a tumor based on a fluorescence observation image in the special observation mode, and confirmation of the position of the tumor in the operative field based on an image in which the normal observation image and the fluorescence observation image overlap in the normal/special observation mode can be appropriately performed according to a desire of the user. In the normal/special observation mode, particularly, the image in which the normal observation image and the fluorescence observation image overlap can be obtained while white light and excitation light are radiated simultaneously, rather than in a time sharing manner. Thus, the tumor in the operative field can be observed in real time. Furthermore, in the present application example, such acquisition of an image in the normal/special observation mode can be executed with a relatively simple configuration of the optical filter 1221, the plurality of image sensors (the first image sensor 1223 and the second image sensor 1225), and the respective functions of the image processing device 1300 (the long-wavelength band image generation unit 1301, the short-wavelength band image generation unit 1303, and the observation image generation unit 1305). Therefore, without a size or cost of a device increasing, an observation image of higher quality can be obtained in the normal/special observation mode.

4-2-3. Another Configuration Example of the Endoscope Device

As a modified example of the endoscope device 1 described above, another configuration example of the endoscope device 1 will be described with reference to FIG. 13. FIG. 13 is a diagram illustrating the other configuration example of the endoscope device 1 illustrated in FIG. 10. Note that the endoscope device according to the present modified example corresponds to the endoscope device 1 illustrated in FIG. 10 in which the configuration of the endoscope unit 1200 is altered. Thus, in FIG. 13, of the configuration of the endoscope device according to the present modified example, only an endoscope unit 1200*c* is illustrated.

Referring to FIG. 13, the endoscope unit 1200*c* of the endoscope device according to the present modified example includes the lens barrel 1210 and an imaging unit 1220*c*. The configuration and the function of this lens barrel 1210 are the same as those of the lens barrel 1210 illustrated in FIG. 10. On the other hand, the imaging unit 1220*c* includes the optical filter 1221, the first image sensor 1223, the second image sensor 1225, and a second optical filter 1227. As described above, the imaging unit 1220*c* corresponds to the imaging unit 1220 of the endoscope device 1 illustrated in FIG. 10 in which the second optical filter 1227 is further provided.

As illustrated, the second optical filter 1227 is provided in the earlier stage of the second image sensor 1225. The second optical filter 1227 is a notch filter which only blocks light corresponding to the wavelength bands of laser light from the second light source unit 120*b* (for example, light of the wavelength band corresponding to the excitation light wavelength (664 nm) of Laserphyrin). By providing the second optical filter 1227, a reception amount of light of the wavelength band corresponding to the excitation light wavelength of Laserphyrin to the second image sensor 1225 can be controlled.

In the present modified example, processes of the observation image generation unit 1305 in the normal observation mode and the special observation mode are the same as those of the endoscope device 1 described above. A process of the observation image generation unit 1305 in the normal/special observation mode, however, is slightly different from the process of the endoscope device 1 described above.

Specifically, in the normal/special observation mode, the first light source unit 101 and the second light source unit 120*b* are driven together and light generated by multiplexing white light from the first light source unit 101 and laser light from the second light source unit 120*b* is radiated to the observation site 1500. At this time, the output of the laser light from the second light source unit 120*b* is adjusted to a value according to PDD and PDT.

In the imaging unit 1220*c*, light of a wavelength of 670 nm or longer is incident on the first image sensor 1223 and light of a wavelength shorter than 670 nm is incident on the second image sensor 1225. A component of the wavelength band corresponding to the excitation light wavelength of Laserphyrin is cut from the light to be incident on the second image sensor 1225.

The long-wavelength band image generation unit 1301 of the image processing device 1300 generates an image showing a tumor based on light of the red band with a wavelength of 670 nm or longer as the first image. In addition, the short-wavelength band image generation unit 1303 generates an image based on light of a red band, green band, and blue band with a wavelength shorter than 670 nm as the second image. A component of the wavelength band corresponding to the excitation light wavelength of Laserphyrin, however, is cut from the second image generated by the short-wavelength band image generation unit 1303.

In the present modified example, the observation image generation unit 1305 generates a combined image by summing up RGB values of the image generated by the long-wavelength band image generation unit 1301 and RGB values of the image generated by the short-wavelength band image generation unit 1303. Since the component of the wavelength band corresponding to the excitation light wavelength of Laserphyrin is cut from the second image generated by the short-wavelength band image generation unit 1303, merely by summing up the RGB values of both images, an image in which a normal observation image and a fluorescence observation image overlap can be obtained.

Specifically, when PDT is performed, the intensity of laser light from the second light source unit 120b is much higher than the intensity of white light from the first light source unit 101. Thus, when an image is generated based on light corresponding to the wavelength bands of laser light from the second light source unit 120b, the reception amount of light of the wavelength band is saturated, and there is a possibility of a normal image not being generated. Therefore, in the endoscope device 1 described above, a combined image is generated by summing up the R value of the first image and the GB values of the second image and cutting the component corresponding to the wavelength bands of laser light from the second light source unit 120b in the stage of a so-called image process in the normal/special observation mode. On the other hand, in the present modified example, an image in which the component of the wavelength bands of laser light is cut can be obtained by providing the second optical filter 1227 in the earlier stage of the second image sensor 1225 to block incidence of light corresponding to the wavelength band of the laser light from the second light source unit 120b on the second image sensor 1225, and simply summing up the RGB values of the first image and the RGB values of the second image.

4-3. Microscope Device 4-3-1. Configuration of a Microscope Device

A configuration of a microscope device to which the illumination devices 10, 20, 30, and 40 are applied will be described with reference to FIGS. 14 and 15. FIG. 14 is a diagram illustrating a configuration example of the microscope device to which the illumination devices 10, 20, 30, and 40 according to the first and second embodiments and the respective modified examples are applied. FIG. 15 is an illustrative diagram for describing a radiation range of radiation light with respect to the observation site 1500.

Note that a case in which the configuration of the illumination device 10 according to the first embodiment is mounted in the microscope device will be described below as an example. As will be described below, when the illumination devices 10, 20, 30, and 40 are applied to the microscope device, a radiation intensity of excitation light to the observation site 1500 is controlled with high accuracy while PDT is performed, and it is preferable to use an illumination device in which the optical fiber 107 is mounted as in the illumination device 10. The present application example, however, is not limited thereto, and a configuration of another illumination device 20, 30, or 40 may be mounted in the microscope device.

Referring to FIG. 14, the microscope device 2 includes an illumination device 2100, an imaging unit 2200, the image processing device 1300, and the display device 1400. Note that, in FIG. 14, the observation site 1500 to which output light from the illumination device 2100 is radiated is also schematically illustrated.

Illumination Device 2100

The illumination device 2100 generates white light (multiplexed white light) for normal observation and excitation light for fluorescence observation. White light and/or excitation light generated by the illumination device 2100 are projected to the outside via the projection lens 1111, and then radiated to the observation site 1500.

Here, the illumination device 2100 corresponds to the illumination device 10 according to the first embodiment described above. Several members, however, are omitted from or added to the illumination device when it is mounted in the microscope device 2.

Specifically, the illumination device 2100 includes the first light source unit 101 which radiates white light, the first collimator optical system 103, a second light source unit 120b which includes at least one laser light source that emits light of a predetermined wavelength band, the coupling optical system 105, the optical fiber 107, the third collimator optical system 109, a dichroic mirror 115b, the condenser optical system 117, a laser line filter 1101, a half mirror 1103, a light detector 1105, another half mirror 1107, another light detector 1109, and a control unit 1120.

As described above, the illumination device 2100 corresponds to the illumination device 10 according to the first embodiment to which the laser line filter 1101, the half mirror 1103, the light detector 1105, the half mirror 1107, and the light detector 1109 are added and from which the second collimator optical system 113 and the diffusion member 111 are omitted. In addition, for the illumination device 2100, the optical characteristics of the second light source unit 120 and the dichroic mirror 115 of the illumination device 10 according to the first embodiment are also altered. Since configurations and functions of other members are the same as those of the respective members shown in FIG. 1, detailed description regarding those members will be omitted. In addition, the control unit 1120 corresponds to the control unit which controls driving of the first light source unit 101 and the second light source unit 120, not illustrated in FIG. 1.

Here, since the configurations and functions of the second light source unit 120b, the dichroic mirror 115b, the laser line filter 1101, the half mirror 1103, the light detector 1105, the half mirror 1107, the light detector 1109, and the control unit 1120 are the same as those of the members of the endoscope device 1 illustrated in FIG. 10, detailed description thereof will be omitted.

As illustrated, in the illumination device 2100, laser light emitted from the second light source unit 120b passes through the coupling optical system 105, the optical fiber 107, the third collimator optical system 109, the laser line filter 1101, and the half mirror 1103 in this order, and is incident on the dichroic mirror 115b as substantially parallel light. On the other hand, white light emitted from the first light source unit 101 passes through the first collimator optical system 103 and is incident on the dichroic mirror 115b as substantially parallel light.

The projection lens 1111 is provided in a partial region of a separating wall of the case of the illumination device 2100, and light that has passed through the dichroic mirror 115b is radiated to the observation site 1500 via the projection lens 1111.

As with the endoscope device 1, a configuration and an operation of the microscope device 2 when Laserphyrin is used as a photosensitive pharmaceutical agent will be described below as an example. In addition, the second light source unit 120 multiplexes and emits laser light of three different wavelength bands in the configuration example described in (1. First embodiment) described above; however, in order to simplify description, the second light source unit 120b will be described as only emitting laser light of a wavelength band corresponding to the excitation light wavelength of Laserphyrin. This corresponds to a state in which, among a plurality of laser light sources included in the second light source unit 120b, only a laser light source that can emit laser light corresponding to the excitation light wavelength of Laserphyrin is driven.

Note that the characteristic of the dichroic mirror 115*b* when Laserphyrin is used is the same as that described with reference to FIGS. 11 and 12. That is, light generated by multiplexing white light emitted from the first light source unit 101 and laser light emitted from the second light source unit 120*b* by the dichroic mirror 115*b* is white light (i.e., multiplexed white light) generated by attenuating a component of the wavelength band corresponding to the excitation light wavelength of Laserphyrin or removing the component from the white light emitted from the first light source unit 101 and complementing the attenuated or removed component with the laser light emitted from the second light source unit 120*b*.

An example of radiation ranges on the observation site 1500 when the multiplexed white light is radiated to the observation site 1500 is illustrated in FIG. 15. When the white light emitted from the first light source unit 101 and the laser light emitted from the second light source unit 120*b* are radiated to the observation site 1500 together, it is preferable particularly in the normal/special observation mode to adjust a first radiation range 1501 of the white light from the first light source unit 101 and a second radiation range 1503 of the laser light from the second light source unit 120*b* such that the second radiation range 1503 is included in the first radiation range 1501 as illustrated in FIG. 15. When the radiation ranges 1501 and 1053 are in the relation as illustrated and PDD or PDT is performed, for example, normal observation of the observation site 1500 is performed using white light from the first light source unit 101, and a site targeted in the normal observation can be irradiated with laser light (i.e., excitation light) from the second light source unit 120*b*.

The adjustment of the first radiation range 1501 and the second radiation range 1503 can be controlled by adjusting the core diameter of the optical fiber 107, the focal length of the third collimator optical system 109, and the focal length of the projection lens 1111. At this time, it is desirable to adjust the optical characteristics of the members so that an image on the emission end face of the optical fiber 107 is formed on the observation site 1500. The reason for this is that, since the emission end of the optical fiber 107 can be conjugate with the observation site 1500 in this case, as the intensity and size of laser light on the emission end face of the optical fiber 107 are adjusted, the intensity and size of the laser light radiated to the observation site 1500 can be adjusted.

Here, when PDT is performed, for example, the intensity of excitation light to be radiated to a lesion part (tumor) per unit time and unit area is generally decided according to the type of tumor, the type of photosensitive pharmaceutical agent, or the like. Thus, by appropriately adjusting the intensity and the size of laser light to be radiated to the observation site 1500 using the optical fiber 107 in the microscope device 2 as described above, PDT can be performed more effectively.

Since the optical fiber 107 is provided and the intensity and the size of laser light on the emission end of the optical fiber 107 that can be conjugated with the observation site 1500 are appropriately adjusted in the microscope device 2, the intensity and the size of laser light to be radiated to the observation site 1500 can be adjusted. Thus, in order to control radiation of excitation light to the observation site 1500 with high accuracy when PDT is performed, it is preferable for the microscope device 2 to be provided with the optical fiber 107 as illustrated.

Imaging Unit 2200

The imaging unit 2200 includes the optical filter 1221, the first image sensor 1223, the second image sensor 1225, and an image lens 2227. The image lens 2227 is provided in a partial region of a separating wall of the case of the imaging unit 2200, and guides reflected light from the observation site 1500 into the case. The light guided into the case of the imaging unit 2200 via the image lens 2227 is incident on the optical filter 1221 provided in the case. Note that, in FIG. 14, propagation of light in the imaging unit 2200 is schematically illustrated with dashed-line arrows.

Since the configurations and the functions of the optical filter 1221, the first image sensor 1223, and the second image sensor 1225 are the same as those of the members of the endoscope device 1 illustrated in FIG. 10, detailed description thereof is omitted. In other words, reflected light from the observation site 1500 is separated into, for example, light of a wavelength of 670 nm or longer and light of a wavelength shorter than 670 nm by the optical filter 1221, and the light of a wavelength of 670 nm or longer is incident on the first image sensor 1223 and the light of a wavelength shorter than 670 nm is incident on the second image sensor 1225.

Image Processing Device 1300

The image processing device 1300 generates a captured image (observation image) of the observation site 1500 based on reflected light from the observation site 1500 detected by the imaging unit 2200. Note that, since a configuration and a function of the image processing device 1300 are the same as those of the image processing device 1300 of the endoscope device 1 illustrated in FIG. 10, detailed description thereof is omitted.

Display Device 1400

The display device 1400 displays an image generated by the observation image generation unit 1305 of the image processing device 1300. Note that a configuration and a function of the display device 1400 are the same as those of the display device 1400 of the endoscope device 1 illustrated in FIG. 10, and thus detailed description thereof is omitted.

4-3-2. Operation of the Microscope Device

Operations of the microscope device 2 described above according to the observation modes will be described. In the microscope device 2, any of the normal observation mode, the special observation mode, and the normal/special observation mode can be selected as an observation mode. Note that, since the operations of the microscope device 2 according to respective observation modes are the same as those of the endoscope device 1 illustrated in FIG. 10 according to the respective observation modes, detailed description regarding overlapping points is omitted.

Normal Observation Mode

In the normal observation mode, light of a broad band corresponding to visible light in the range of approximately 400 nm to 750 nm is radiated to the observation site 1500 and an image of the observation site 1500 is acquired.

When the normal observation mode is selected as an observation mode by a user, the first light source unit 101 and the second light source unit 120*b* of the illumination device 2100 are driven together. At this time, output light from the illumination device 2100 is light generated by multiplexing white light from the first light source unit 101 and laser light from the second light source unit 120*b* (multiplexed white light) as shown in FIG. 12. Here, in the normal observation mode, the output of the laser light from the second light source unit 120*b* can be appropriately adjusted so that the multiplexed white light has a similar hue to the original white light output from the first light source unit 101.

In the imaging unit 2200, light of a wavelength of 670 nm or longer is incident on the first image sensor 1223 and light of a wavelength shorter than 670 nm is incident on the second image sensor 1225 as described above. Thus, the long-wavelength band image generation unit 1301 of the image processing device 1300 generates an image as the first image based on light of a red band with a wavelength of 670 nm or longer. In addition, the short-wavelength band image generation unit 1303 generates an image as the second image based on light of a red band, a green band, and a blue band with a wavelength shorter than 670 nm.

In the normal observation mode, the observation image generation unit 1305 generates a combined image by summing up the RGB values of the image generated by the long-wavelength band image generation unit 1301 and the RGB values of the image generated by the short-wavelength band image generation unit 1303. The combined image generated in this way is a normal observation image corresponding to radiation light of a visible light band (about 400 nm to 750 nm).

Special Observation Mode

In the special observation mode, narrow-band light corresponding to the excitation light wavelength of Laserphyrin that is a photosensitive pharmaceutical agent is radiated to the observation site 1500 and an image based on fluorescence from the observation site 1500 is acquired. The special observation mode is an observation mode used when PDD and PDT are performed.

When the special observation mode is selected as an observation mode by a user, only the second light source unit 120b of the illumination device 2100 is driven. At this time, output light from the illumination device 2100 is light without the spectrum of white light in the spectrum shown in FIG. 12, i.e., laser light having the excitation light wavelength of Laserphyrin as the center wavelength. Note that, when PDT is performed in the special observation mode, the output of laser light from the second light source unit 120b is set to be stronger than when PDD is performed.

In the imaging unit 2200, light having a wavelength of 670 nm or longer is incident on the first image sensor 1223 and light having a wavelength shorter than 670 nm is incident on the second image sensor 1225 as described above. Thus, the long-wavelength band image generation unit 1301 of the image processing device 1300 generates an image based on light in a red band with a wavelength of 670 nm or longer as the first image.

Here, since the fluorescence wavelength of Laserphyrin is 672 nm, the first image generated by the long-wavelength band image generation unit 1301 is an image based on fluorescence of Laserphyrin, i.e., an image in which a tumor that is an observation target in the special observation mode is selectively visible. Thus, in the special observation mode, the observation image generation unit 1305 outputs the image generated by the long-wavelength band image generation unit 1301, i.e., the fluorescence observation image to the display device 1400.

Normal/Special Observation Mode

In the normal/special observation mode, by simultaneously performing radiation of white light for normal observation and radiation of excitation light for special observation, recognition of the shape of an operative field based on a normal observation image and fluorescence observation of a tumor based on a special observation image can be simultaneously performed.

When the normal/special observation mode is selected as an observation mode by a user, the first light source unit 101 and the second light source unit 120b of the illumination device 2100 are driven together as in the normal observation mode. At this time, the output light from the illumination device 1100 is light generated by multiplexing the white light from the first light source unit 101 and laser light from the second light source unit 120b (multiplexed white light) as shown in FIG. 12. Unlike in the normal observation mode, however, the output of the laser light from the second light source unit 120b is adjusted to a value according to PDD and PDT in the normal/special observation mode. Note that, in this case, when PDT is performed, the output of laser light from the second light source unit 120b is set to be stronger than when PDD is performed, like in the special observation mode.

In the imaging unit 2200, light of a wavelength of 670 nm or longer is incident on the first image sensor 1223 and light of a wavelength shorter than 670 nm is incident on the second image sensor 1225 as described above. Thus, the long-wavelength band image generation unit 1301 of the image processing device 1300 generates an image as the first image based on light of a red band with a wavelength of 670 nm or longer. In addition, the short-wavelength band image generation unit 1303 generates an image as the second image based on light of a red band, a green band, and a blue band with a wavelength shorter than 670 nm.

Here, since the fluorescence wavelength of Laserphyrin is 672 nm, the first image generated by the long-wavelength band image generation unit 1301 is an image based on fluorescence of Laserphyrin, i.e., an image in which a tumor is selectively visible. On the other hand, a red component of the second image generated by the short-wavelength band image generation unit 1303 is considered to be based on a component corresponding to the excitation light wavelength of Laserphyrin of radiation light. The red component of the second image can be said to be a component that hinders fluorescence observation of a tumor.

Thus, the observation image generation unit 1305 generates a combined image in the normal/special observation mode by summing up an R value of the first image generated by the long-wavelength band image generation unit 1301 and GB values of the second image generated by the short-wavelength band image generation unit 1303. The combined image generated in this manner is an image in which a normal observation image based on the GB values of the second image and a fluorescence observation image based on the R value of the first image overlap. In the image, a tumor is displayed in red in the normal observation image based on the GB values.

The configuration and operations of the microscope device 2 into which the illumination device 2100 having substantially the same configuration as the illumination device 10 according to the first embodiment is incorporated have been described above. According to the microscope device 2, the following effects can be exhibited, like the endoscope device 1 described above.

In the illumination device 2100, white light from the first light source unit 101 and laser light from the second light source unit 120b are multiplexed on the same optical axis. Thus, shadows produced due to undulation of the observation site 1500 are observed in the same shape when white light from the first light source unit 101 is used as radiation light and when laser light from the second light source unit 120b is used as radiation light. Thus, in a portion in which no shadow is produced during normal observation, a shadow is produced during fluorescence observation, and thus a situation in which it is not possible to radiate excitation light to that portion does not occur. Therefore, a user can smoothly perform a series of operations of radiating excitation light in the special observation mode to a spot targeted in the normal observation mode, and user convenience can be improved.

In addition, in the illumination device 2100, the first light source unit 101 is configured with, for example, a white LED and the second light source unit 120*b* is configured with, for example, a semiconductor laser. When the first light source unit 101 and the second light source unit 120*b* are configured with semiconductor light emission elements as above, the output of emitted light from each of the light source units can be independently controlled at an arbitrary timing by appropriately controlling their driving currents. Thus, the output light from the illumination device 1100 can be adjusted at a higher degree of freedom.

Note that, although the case in which only laser light of the wavelength band corresponding to the excitation light wavelength of the photosensitive pharmaceutical agent is emitted from the second light source unit 120*b* has been described in the application examples described above for the sake of simplification, a plurality of laser light beams of different wavelength bands (for example, red laser light, green laser light, and blue laser light corresponding to the three primary colors of light) may be emitted from the second light source unit 120*b* in the illumination device 2100 as in the illumination devices 10, 20, 30, and 40. When the second light source unit 120*b* is configured in this way, a color temperature of multiplexed white light used as radiation light in the normal observation mode and the normal/special observation mode can be adjusted more easily by controlling the outputs of the laser light beams of the respective colors independently of each other.

In addition, the illumination device 2100 is provided with the light detectors 1105 and 1109 for respectively detecting intensities of white light from the first light source unit 101 and laser light from the second light source unit 120*b* before multiplexing. Then, according to the intensities of the white light and the laser light monitored by the light detectors 1105 and 1109, driving of the first light source unit 101 and the second light source unit 120*b* is controlled. Thus, the intensities of the emitted light from the first light source unit 101 and the second light source unit 120*b* can be controlled with high accuracy, and quality of the output light from the illumination device 1100 can be further improved.

In addition, in the illumination device 2100, the dichroic mirror 115*b* attenuates or removes light of a predetermined wavelength band from the white light from the first light source unit 101 and multiplexes the white light with the laser light from the second light source unit 120*b* so that the attenuated or removed component of the wavelength band is complemented. In addition, in this case, the output of the laser light from the second light source unit 120*b* can be appropriately adjusted so that the multiplexed light has a similar hue to the original white light. Thus, a change in the hue of the observation site 1500 sensed by the user can be suppressed to a minimum level when the multiplexed white light is used for observation in the normal observation mode and the normal/special observation mode.

In addition, in the microscope device 2, the imaging unit 2200 is configured such that light of the wavelength band corresponding to excitation light is not incident but light of the wavelength band corresponding to fluorescence is incident on the first image sensor 1223 by the optical filter 1221 in the special observation mode and the normal/special observation mode. In this manner, according to the present application example, with the relatively simple configuration of the optical filter 1221, a weak fluorescence component emitted from the observation site 1500 can be detected with high accuracy and thus a high-definition fluorescence observation image can be obtained.

In addition, as processes by the observation image generation unit 1305 are appropriately switched according to observation modes in the microscope device 2, identification of an operative field based on a normal observation image in the normal observation mode, diagnosis of a tumor based on a fluorescence observation image in the special observation mode, and confirmation of the position of the tumor in the operative field based on an image in which the normal observation image and the fluorescence observation image overlap in the normal/special observation mode can be appropriately performed according to a desire of the user. In the normal/special observation mode, particularly, the image in which the normal observation image and the fluorescence observation image overlap can be obtained while white light and excitation light are radiated simultaneously, rather than in a time sharing manner. Thus, the tumor in the operative field can be observed in real time. Furthermore, in the present application example, such acquisition of an image in the normal/special observation mode can be executed with a relatively simple configuration of the optical filter 1221, the plurality of image sensors (the first image sensor 1223 and the second image sensor 1225), and the respective functions of the image processing device 1300 (the long-wavelength band image generation unit 1301, the short-wavelength band image generation unit 1303, and the observation image generation unit 1305). Therefore, without a size or cost of a device increasing, an observation image of higher quality can be obtained in the normal/special observation mode.

II. Illumination Device that Includes a Multiplexing Unit with a Polarization Conversion Element and a Polarizing Beam Splitter

5. THIRD EMBODIMENT

A configuration of an illumination device according to a third embodiment of the present disclosure will be described with reference to FIGS. 16 to 18. FIG. 16 is a diagram illustrating a configuration example of the illumination device according to the third embodiment. FIG. 17 is an illustrative diagram for describing a configuration of a light guide on which output light from the illumination device illustrated in FIG. 1 is incident. FIG. 18 is a diagram for describing characteristics of light multiplexed by the multiplexing member of the illumination device illustrated in FIG. 1.

Note that the illumination device according to the third embodiment and one according to a fourth embodiment to be described below can be properly applied to a light source unit of an observation device such as an endoscope device or a microscope device for observing an operative field of a patient. Hereinbelow, cases in which the illumination devices according to the third and fourth embodiments are applied to an endoscope device will be described as examples except for (8-3. Endoscope device) described below. When the illumination devices according to the third and fourth embodiments are applied to endoscope devices, light emitted from the illumination devices is incident on an end of a light guide that continues inside a lens barrel of an endoscope, and therefore drawings showing configurations of the illumination devices provided below also illustrate one end of the light guide on which light is incident.

Referring to FIG. 16, the illumination device 50 according to the third embodiment includes a first light source unit 101 that emits white light and a first collimator optical system 103. In addition, the illumination device 50 further includes a second light source unit 120 which includes at least one laser light source that emits light of a predetermined wavelength band, a coupling optical system 105, an optical fiber 107, a third collimator optical system 109, a diffusion member 111, a second collimator optical system 113, a multiplexing member 115c, and a condenser optical system 117. In addition, although not illustrated, the illumination device 50 includes driving control units which control driving of the first light source unit 101 and the second light source unit 120 (which correspond to a first-light-source-unit driving control unit 1121 and a second-light-source-unit driving control unit 1123 shown in FIG. 22 to be described below).

White light emitted from the first light source unit 101 becomes substantially parallel light as it passes through the first collimator optical system 103, and is incident on the multiplexing member 115c. On the other hand, laser light emitted from the second light source unit 120 passes through the coupling optical system 105, the optical fiber 107, the third collimator optical system 109, the diffusion member 111, and the second collimator optical system 113 in this order, thereby turning into substantially parallel light, and is incident on the multiplexing member 115c. The multiplexing member 115c multiplexes the white light and the laser light, and the multiplexed light is incident on an end of a light guide 130 via the condenser optical system 117.

Here, as a laser light source included in the second light source unit 120, one that can emit light of a wavelength band which can function as excitation light in fluorescence observation can be mounted in the illumination device 50 according to an observation purpose. In addition, the illumination device 50 is configured to switch modes including a normal observation mode in which an operative field is observed using white light, a special observation mode in which, by detecting fluorescence excited by light of a predetermined wavelength band (hereinafter also referred to as narrow-band light), a site within an operative field emitting the fluorescence is intensively observed, and a normal/special observation mode in which normal observation and special observation are simultaneously performed (details thereof will be described in (4. Application examples) below). Note that fluorescence observation in the special observation mode and the normal/special observation mode may involve detecting self-fluorescence of a site radiated with excitation light, or detecting chemical fluorescence brought by various fluorescence reagents (photosensitive pharmaceutical agents) introduced into a radiated site.

In the normal observation mode, white light generated by multiplexing white light from the first light source unit 101 and laser light from the second light source unit 120 is radiated to an operative field. Accordingly, a normal observation image based on the white light is obtained. Note that, in description below, white light generated by multiplexing white light from the first light source unit 101 and laser light from the second light source unit 120 will also be referred to as multiplexed white light for the sake of convenience in order to distinguish it from white light from the first light source unit 101. In the normal observation mode, an output of laser light from the second light source unit 120 is appropriately adjusted so that multiplexed white light has a desired hue (for example, a hue similar to original white light emitted from the first light source unit 101, a hue corresponding to an arbitrary standard illuminant, or the like).

In the special observation mode, white light is not emitted from the first light source unit 101 (i.e., the white light source of the first light source unit 101 is turned off), only laser light of a wavelength band set according to an observation purpose is emitted from the second light source unit 120 (i.e., only the laser light source suitable for the observation purpose is turned on), and thus narrow-band light is radiated to an operative field. Accordingly, a fluorescence observation image based on fluorescence is obtained. In the fluorescence observation image, only a site suitable for the observation purpose, for example, a tumor or the like, is shown.

In the normal/special observation mode, multiplexed white light is radiated to an operative field as in the normal observation mode; however, an output of laser light from the second light source unit 120 is adjusted to have an intensity (i.e., intensity suitable for fluorescence observation) according to an observation purpose. Accordingly, an image in which a normal observation image and a special observation image overlap is obtained.

Each constituent member of the illumination device 50 will be described in more detail below.

At least one second light source unit 120 is provided in the illumination device 50. The second light source unit 120 includes at least one laser light source which emits laser light of a predetermined wavelength band. In the illustrated example, the second light source unit 120 includes a laser light source 121R that emits laser light of a red band (for example, laser light having the center wavelength of about 638 nm), a laser light source 121G that emits laser light of a green band (for example, laser light having the center wavelength of about 532 nm), and a laser light source 121B that emits laser light of a blue band (for example, laser light having the center wavelength of about 450 nm). Each of the laser light sources 121R, 121G and 121B is provided with a collimator optical system, and thus laser light of each wavelength band is emitted as a parallel luminous flux.

As the laser light sources 121R, 121G and 121B, various known laser light sources, for example, a semiconductor laser, a solid-state laser, and the like, can be used. Alternatively, as the laser light sources 121R, 121G and 121B, a combination of the laser light sources and a wavelength conversion mechanism may be used. In the second light source unit 120, driving of each of the laser light sources 121R, 121G and 121B can be controlled independently.

As described above, the second light source unit 120 can include the laser light sources 121R, 121G and 121B which emit light of, for example, respective wavelength bands corresponding to the three primary colors of light. By configuring the second light source unit 120 in this manner, outputs of the laser light sources 121R, 121G and 121B corresponding to the respective colors are appropriately adjusted, and thereby a color temperature of multiplexed white light can be adjusted.

The third embodiment, however, is not limited to the above example, and a type of laser light source included in the second light source unit 120 may be appropriately selected according to an observation purpose, a type of observation target, and the like. When various kinds of fluorescence observation are to be performed, for example, the second light source unit 120 can be configured to include laser light sources which emit laser light of wavelength bands corresponding to excitation light according to each fluorescence observation method. When observation using indocyanine green (ICG) fluorescence contrast radiography is performed, for example, the second light source unit 120 is configured to include at least a laser light source that emits laser light of a near-infrared band.

The second light source unit 120 further includes a dichroic mirror 122R that reflects light of a wavelength band corresponding to red laser light from the laser light source 121R, a dichroic mirror 122G that reflects light of a wavelength band corresponding to green laser light from the laser light source 121G and a dichroic mirror 122B that reflects light of a wavelength band corresponding to blue laser light from the laser light source 121B. The dichroic mirrors 122R, 122G, and 122B multiplex laser light emitted from the respective laser light sources 121R, 121G, and 121B becoming a parallel luminous flux, and the light is emitted as one luminous flux toward the coupling optical system 105 in the later stage.

Note that the dichroic mirrors 122R, 122G, and 122B are examples of multiplexing members that multiplex laser light from the laser light sources 121R, 121G and 121B, and as the multiplexing members, other arbitrary members may be used. For example, as a member for multiplexing laser light from each of the laser light sources 121R, 121G and 121B, a dichroic prism may be used when multiplexing is performed based on wavelengths, a polarizing beam splitter (PBS) may be used when multiplexing is performed based on polarization, or a beam splitter may be used when multiplexing is performed based on amplitude.

The coupling optical system 105 includes, for example, a condenser lens (collector lens), and causes laser light emitted from the second light source unit 120 to be optically coupled to an incidence end of the optical fiber 107. Note that, although the coupling optical system 105 is illustrated as one convex lens in the example illustrated in FIG. 16 for the sake of convenience, a detailed configuration of the coupling optical system 105 is not limited thereto. The coupling optical system 105 may have the function of causing laser light to be coupled to the incidence end of the optical fiber 107, and may be configured to be appropriately combined with a known optical element.

The optical fiber 107 guides laser light emitted from the second light source unit 120 to the third collimator optical system 109 provided in the later stage. Since light emitted from the optical fiber 107 is a rotationally symmetric beam, as the optical fiber 107 guides laser light, luminance distribution becomes more uniform within its plane.

A type of the optical fiber 107 is not particularly limited, but as the optical fiber 107, a known multi-mode optical fiber (for example, a step-index multi-mode optical fiber) can be used. In addition, the core diameter of the optical fiber 107 is not particularly limited, and one with a core diameter of about, for example, 1 mm may be used.

In the third embodiment, the laser light is guided to the incidence end of the optical fiber 107 such that the incidence numerical apertures of the laser light from the laser light sources 121R, 121G and 121B coincide with each other at the incidence end of the optical fiber 107. At this time, it is desirable that, by optimizing the focal length of a lens that collimates laser light emitted from the laser light sources 121R, 121G and 121B, adjusting incidence positions of the laser light on the coupling optical system 105 (i.e. collector lens), or the like, laser light emitted from an emission end of the optical fiber 107 be a solid ray of light of which the amount near the central optical axis of the optical fiber 107 is equal to the amount in the peripheral part, rather than a doughnut-shaped ray of light of which the amount near the central optical axis of the optical fiber 107 is smaller than the amount in the peripheral part.

The third collimator optical system 109 is provided in the later stage of the emission end of the optical fiber 107, and converts laser light emitted from the optical fiber 107 into a parallel luminous flux. As the third collimator optical system 109 converts laser light into a parallel luminous flux, a diffusion state of the laser light in the diffusion member 111 provided in the later stage can be easily controlled. Note that, although the third collimator optical system 109 is illustrated as one convex lens in the example illustrated in FIG. 16 for the sake of convenience, a detailed configuration of the third collimator optical system 109 is not limited thereto. The third collimator optical system 109 may have the function of converting laser light into a parallel luminous flux, and may be configured to be appropriately combined with a known optical element.

The diffusion member 111 is provided near a focal position on the rear side of the third collimator optical system 109, and included in a secondary light source by diffusing the laser light that has become the parallel luminous flux output from the third collimator optical system 109. That is to say, a light emission end of the diffusion member 111 functions as a secondary light source. In addition, the angle of light emitted from the optical fiber 107 is generally uneven depending on laser light; however, divergence angles become uniform after light passes the diffusion member 111. As described above, according to the third embodiment, color unevenness at the time of radiation, which is expected to occur in, for example, the general existing illumination devices introduced in above-described PTL 6 to PTL 9, is reduced due to the diffusion member 111.

A size of the secondary light source formed by the diffusion member 111 can be controlled according to a focal length of the third collimator optical system 109. In addition, the NA of emitted light can be controlled according to a diffusion angle of the diffusion member 111. Due to these two effects, both the size of a condensing spot and the incidence NA when light is coupled to the incidence end of the light guide 130 can be controlled independently of each other. Note that, although the actual range of the periphery of a focal position on the rear side of the third collimator optical system 109 at which the diffusion member 111 is to be disposed is not particularly limited, the range is preferably set to, for example, a range of about ±10% of focal distances upstream and downstream from the focal position on the rear side of the third collimator optical system 109.

Note that a specific type of the diffusion member 111 is not particularly limited, and a known diffusion element may be used as the diffusion member 111. As examples of such a diffusion member, for example, a frosted ground glass, an opal diffuser that uses a diffusion characteristic by dispersing light diffusion materials within glass, and a holographic diffuser can be exemplified. A holographic diffuser is made by creating holograph patterns on a predetermined board, and it is particularly preferable to be used as the diffusion member 111 because a diffusion angle of emitted light can be set to an arbitrary angle.

Laser light emitted from the diffusion member 111 is guided to the second collimator optical system 113. The second collimator optical system 113 converts the light from the diffusion member 111 (i.e., light from the secondary light source) into a parallel luminous flux to cause the light to be incident on the multiplexing member 115*c*.

Here, the laser light that has passed through the second collimator optical system 113 may not be completely parallel light, and may be diverging light close to a parallel light state. In other words, the second collimator optical system 113 and the condenser optical system 117 to be described below may be a finite conjugate rather than an infinite conjugate. In the present specification, for the sake of convenience, light that has passed through a collimator optical system and becomes parallel light or light that is closed to a parallel light state will be referred to as substantially parallel light. That is, substantially parallel light is a concept that includes parallel light or diverging light. Note that a configuration example of the illumination device 50 when white light and laser light are multiplexed as diverging light will be described again in (7-1. Modified example in which white light and laser light are multiplexed as diverging light) in detail.

At least one first light source unit 101 is provided in the illumination device 50, and emits white light. A type of white light source included in the first light source unit 101 is not limited as long as it emits white light. As the white light source, for example, an arbitrary light source such as a white light emitting diode (LED), a laser-excited fluorescent substance, a xenon lamp, or a halogen lamp may be used. In the third embodiment, as an example, a so-called fluorescent substance-type white LED that uses a fluorescent substance excited by a blue LED is assumed to be used as the white light source of the first light source unit 101.

White light emitted from the first light source unit 101 is converted into a parallel luminous flux by the first collimator optical system 103, and is incident on the multiplexing member 115c from a direction different from that of the laser light emitted from the diffusion member 111 (in the illustrated example, the direction in which the optical axes are substantially orthogonal to each other). Note that the white light that has passed through the first collimator optical system 103 may not be completely parallel light. In other words, the first collimator optical system 103 and the condenser optical system 117 to be described below may be a finite conjugate rather than an infinite conjugate. That is, the first collimator optical system 103 converts the white light into substantially parallel light and causes it to be incident on the multiplexing member 115c.

Note that, although the first collimator optical system 103 is illustrated as one convex lens in the example shown in FIG. 16 for the sake of convenience, a detailed configuration of the first collimator optical system 103 is not limited thereto. The first collimator optical system 103 may have the function of converting white light into substantially parallel light, and may be configured to be appropriately combined with a known optical element.

The multiplexing member 115c multiplexes white light emitted from the first light source unit 101 and laser light emitted from the second light source unit 120. The multiplexing member 115c includes a polarizing beam splitter 141, a first polarization conversion element 142, and a second polarization conversion element 143.

The first polarization conversion element 142 is disposed on the optical path on which white light is incident on the polarizing beam splitter 141, and white light converted into substantially parallel light by the first collimator optical system 103 passes through the first polarization conversion element 142 and then is incident on the polarizing beam splitter 141. The first polarization conversion element 142 includes, for example, a P/S converter and a fly's-eye lens having a function of aligning polarization of incident light in a fixed direction. In the third embodiment, the first polarization conversion element 142 converts incident white light into, for example, P-polarized light.

The second polarization conversion element 143 is disposed on the optical path on which laser light is incident on the polarizing beam splitter 141, and laser light converted into substantially parallel light by the second collimator optical system 113 passes through the second polarization conversion element 143 and then is incident on the polarizing beam splitter 141. The second polarization conversion element 143 includes, for example, a P/S converter and a fly's-eye lens having a function of aligning polarization of incident light in a fixed direction. In the third embodiment, the second polarization conversion element 143 converts incident laser light into, for example, P-polarized light.

In the illustrated example, the polarizing beam splitter 141 is designed to reflect a P-polarized component of incident light and transmit an S-polarized component. That is, the polarizing beam splitter 141 has the characteristic of reflecting light that has passed through the first polarization conversion element 142 and transmitting light that has passed through the second polarization conversion element 143. In the illumination device 50, the diffusion member 111, the second collimator optical system 113, the second polarization conversion element 143, the polarizing beam splitter 141, and the condenser optical system 117 are disposed in one row in this order. In addition, the first light source unit 101, the first collimator optical system 103, and the first polarization conversion element 142 are disposed such that white light is incident on the polarizing beam splitter 141 from the direction in which the white light is substantially orthogonal to the optical axis of the laser light. Thus, the laser light which has been S-polarized by the second polarization conversion element 143 penetrates the polarizing beam splitter 141 and then is incident on the condenser optical system 117. In addition, the white light which has been P-polarized by the first polarization conversion element 142 is reflected by the polarizing beam splitter 141 and then is incident on the condenser optical system 117.

As described above, the multiplexing member 115c has the function of multiplexing white light emitted from the first light source unit 101 and laser light emitted from the second light source unit 120 by setting the polarization directions of light to be orthogonal to each other. By setting the polarization directions to be orthogonal to each other and multiplexing the white light and the laser light, light beams of the same wavelength can be multiplexed, unlike, for example, multiplexing based on wavelengths using a dichroic mirror or the like. Note that details of a characteristic of light multiplexed by the multiplexing member 115c will be described below with reference to FIG. 18.

Here, although the first polarization conversion element 142 and the second polarization conversion element 143 are disposed respectively on the optical path of white light and the optical path of laser light in the configuration example illustrated in FIG. 16, both the first polarization conversion element 142 and the second polarization conversion element 143 may not necessarily be provided. In the third embodiment, since white light incident on the multiplexing member 115c is white light emitted from a white LED, the light is in a state in which various polarization components are mixed (hereinafter such polarization will be referred to as random polarization). In addition, since light that has passed through an optical fiber is generally known to be subject to random polarization, laser light incident on the multiplexing member 115c via the optical fiber 107 is also of random polarization. Therefore, in the configuration example shown in FIG. 16, since white light and laser light are incident on the polarizing beam splitter 141 with their polarization directions orthogonal to each other, the first polarization conversion element 142 and the second polarization conversion element 143 are provided together.

Thus, when the illumination device 50 is configured such that the first light source unit 101 and/or the second light source unit 120 are configured as light sources that can emit light of predetermined polarization directions and white light and/or laser light are incident on the polarizing beam splitter 141 with the polarization directions maintained, a polarization conversion element may not necessarily be provided on the optical path of light with an aligned polarization direction among the white light and the laser light. In other words, in the illumination device 50, at least a polarization conversion element can be disposed on the optical path of light of random polarization among white light and laser light.

White light emitted from a white LED or a lamp light source, for example, that is highly likely to be used as the first light source unit 101, however, is random polarization light in general. In addition, the polarization direction of light changes only after the light passes through an optical member disposed on the optical path, such as the optical fiber 107 described above. Thus, when the illumination device 50 is actually configured, there is a high possibility of at least any of white light and laser light incident on the multiplexing member being random polarization light. Therefore, the multiplexing member 115c can be suitably configured to include the first polarization conversion element 142 and/or the second polarization conversion element 143.

Note that the type of the polarizing beam splitter 141 is not specifically limited, and as the polarizing beam splitter 141, a polarizing beam splitter with any of various known configurations may be used. In addition, the type of the first polarization conversion element 142 and the second polarization conversion element 143 is not specifically limited, and a first polarization conversion element and a second polarization conversion element with various known configurations may be used as the first polarization conversion element 142 and the second polarization conversion element 143.

The condenser optical system 117 is configured with, for example, a condenser lens (collector lens), and causes light multiplexed by the multiplexing member 115c to form an image on the incidence end of the light guide 130 at a paraxial lateral magnification.

Here, an image-forming magnification of the second collimator optical system 113 and the condenser optical system 117 ([a focal length of the condenser optical system 117]/[a focal length of the second collimator optical system 113]) is set such that a size and a divergence angle of the secondary light source match the core diameter and the incidence NA of the light guide 130. In addition, an image-forming magnification of the first collimator optical system 103 and the condenser optical system 117 ([a focal length of the condenser optical system 117]/[a focal length of the first collimator optical system 103]) is set such that they match the core diameter and the incidence NA of the light guide so that white light forms an image on the incidence end of the light guide 130 with high efficiency.

FIG. 17 illustrates a configuration example of the light guide 130. In FIG. 17, an end of the light guide 130 is illustrated. The light guide 130 includes a bundle of a plurality of optical fibers each including a fiber core and a fiber clad. Here, the condenser optical system 117 according to the third embodiment is configured such that light from the secondary light source forms an image so that the light fills the area of an illumination target (the incidence end of the light guide 130 in the third embodiment) as much as possible, unlike in a general configuration. That is to say, in the third embodiment, the condenser optical system 117 can be configured to condense light from the secondary light source on the incidence end of the light guide 130 so that the size of an image of the secondary light source formed on the incidence end of the light guide 130 becomes substantially the same as the diameter of the incidence end of the light guide 130. Accordingly, speckle noise of the entire illumination device 50 can be reduced.

Speckle noise is known to depend on luminance distribution of a light source. For example, when a light source is an ideal light source, luminance distribution thereof can be regarded as a delta function, and all points on an object surface irradiated with light from the light source interfere with each other, and thus coherence becomes high. Consequently, speckle noise increases. Such a light source (point light source) is called a coherent light source, and speckle noise increases when such a coherent light source is used.

On the other hand, when an infinitely large uniform light source is assumed as a light source, luminance distribution thereof becomes uniform, interference occurs only at the same position on an object surface irradiated with light from the light source, and thus coherence becomes low. Consequently, speckle noise decreases. Such an infinitely large light source is called an incoherent light source, and speckle noise decreases when an incoherent light source is used.

A light source actually mounted in the illumination device 50 is a partially coherent light source that is spatially positioned between a coherent light source and an incoherent light source, and thus, as the size of the light source becomes seemingly larger and luminance distribution of the light source becomes more uniform, coherence and speckle noise are considered to be reduced.

Here, when light from the secondary light source is condensed on the incidence end of the light guide 130 so that an image of the secondary light source is smaller than the diameter of the incidence end of the light guide 130, only some optical fibers included in the light guide 130 contribute to light guidance, and as a result, when emitted light from the light guide 130 is radiated to an observation site, the size of the light source when the observation site is observed from a radiated face becomes seemingly small, and there is concern of speckle noise worsening.

On the other hand, when light from the secondary light source is condensed on the incidence end of the light guide 130 so that an image of the secondary light source is larger than the diameter of the incidence end of the light guide 130, vignetting of laser light arises on the incidence end face of the light guide 130, and there is concern of efficiency in light coupling decreasing.

Thus, by condensing light from the secondary light source on the incidence end of the light guide 130 so that the size of an image of the secondary light source becomes substantially the same as the diameter of the incidence end of the light guide 130 as described above, speckle noise can be reduced while improving efficiency in light coupling to the incidence end face of the light guide 130.

Here, such a configuration for reducing speckle noise is not applied to, for example, existing general illumination devices as introduced in PTL 6 to PTL 9 described above. In this manner, in the illumination device 50 according to the third embodiment, an observation image in which speckle noise is reduced more than in a general illumination device can be obtained.

Note that, although the condenser optical system 117 is illustrated as one convex lens in the example shown in FIG. 16 for the sake of convenience, a detailed configuration of the condenser optical system 117 is not limited thereto. The condenser optical system 117 may have the respective functions as described above, and may be configured to be appropriately combined with a known optical element.

Here, a characteristic of light multiplexed by the multiplexing member 115c will be described with reference to FIG. 18. FIG. 18 shows an example of the spectrum of light obtained after the multiplexing member 115c multiplexes white light emitted from the first light source unit 101 and laser light emitted from the second light source unit 120. In the illustrated example, the spectrum obtained when red laser light, green laser light, and blue laser light are multiplexed with white light is shown. By multiplexing white light and the laser light in this manner, so-called new white light (i.e., multiplexed white light) can be generated in the third embodiment. The multiplexed white light is radiated to an operative field in the normal observation mode and the normal/special observation mode in the third embodiment. Note that, in the special observation mode, only the second light source unit 120 is driven without driving the first light source unit 101, and laser light of a wavelength band corresponding to excitation light at the time of fluorescence observation is radiated to an operative field.

In the existing general illumination devices introduced in, for example, PTLs 6, 8, and 9 described above, however, a multiplexing member guides white light and laser light onto the same optical axis, but any of white light and laser light is selectively radiated to an operative field by appropriately controlling driving of a white light source and a laser light source, or appropriately controlling removal of a filter from an optical path and disposition thereof on the optical path. That is to say, in the technologies of PTLs 6, 8, and 9, white light from the white light source is directly radiated to an operative field in the normal observation mode. In addition, white light generated when a multiplexing member multiplexes white light and laser light is radiated to an operative field in the technology disclosed in PTL 7; however, the multiplexing member has a part configured to be a transmissive unit which transmits components of all wavelength bands of the white light, and as a result, the white light from a white light source that has penetrated the transmissive unit is directly radiated to an operative field.

As described above, in the existing general illumination devices exemplified in PTL 6 to PTL 9 described above, white light from the white light source such as a halogen lamp or a white LED can be radiated directly to an operative field in the normal observation mode. Thus, although the spectrum of the white light radiated to the operative field can be adjusted to some extent by using various filters and the like, the spectrum is basically fixed to the type of the white light source, and thus it is difficult to control the spectrum of the radiated light in detail.

On the other hand, according to the third embodiment, white light generated by multiplexing white light emitted from the first light source unit 101 and laser light emitted from the second light source unit 120 can be radiated to an operative field in the normal observation mode and the normal/special observation mode as described above. In addition, the second light source unit 120 can include the laser light sources 121R, 121G and 121B which emit light of, for example, respective wavelength bands corresponding to the three primary colors of light. According to this configuration, by appropriately adjusting a mixing ratio of laser light emitted from the second light source unit 120, the spectrum of the multiplexed white light can be controlled and a color temperature thereof can be adjusted. In this manner, a color temperature can be adjusted on a light source side, rather than being adjusted by a filter or the like in a later stage of the illumination device according to the third embodiment. By appropriately adjusting the color temperature, color temperatures of white light from various light sources, for example, the standard illuminant D65, the common illuminant D50, or the like can be reproduced in output light from the illumination device 50.

The configuration of the illumination device 50 according to the third embodiment has been described above with reference to FIGS. 16 to 18. According to the third embodiment described above, since divergence angles of a plurality of laser light beams output from the second light source unit 120 become uniform by providing the diffusion member 111 on the optical path of the laser light, color unevenness during radiation of output light from the illumination device 50 is reduced. In addition, by configuring light from the secondary light source to form an image on the incidence end of the light guide 130 so that the light fills the area of the incidence end of the light guide 130 as much as possible, the condenser optical system 117 can reduce speckle noise in the illumination device 50 as a whole. In addition, by adjusting a mixing ratio of laser light of the second light source unit 120, a color temperature of multiplexed white light can be adjusted. Thus, according to the third embodiment, high-quality white light can be more uniformly used as radiation light in observation using white light (i.e., observation in the normal observation mode or the normal/special observation mode), and thus an observation image of higher quality can be obtained.

In addition, by appropriately controlling driving of the first light source unit 101 and the second light source unit 120 in the illumination device 50 according to the third embodiment as described above, the normal observation mode, the special observation mode, and the normal/special observation mode can be switched. As described above, switching of a wavelength band of radiation light and obtaining an observation image of higher quality can be simultaneously achieved according to the third embodiment.

Here, although the white light and the laser light are multiplexed as the polarizing beam splitter 141 of the multiplexing member 115c reflects white light that is S-polarized light and transmits laser light that is P-polarized light in the configuration example described above, the third embodiment is not limited thereto. The illumination device 50 may be configured such that, by setting the reflection characteristic and the transmission characteristic of the polarizing beam splitter 141 to be reversed with respect to the above-described characteristics, white light that has passed through the polarizing beam splitter 141 is multiplexed with laser light that has been reflected by the polarizing beam splitter 141, and the multiplexed light is incident on the light guide 130 via the condenser optical system 117.

In addition, the configuration example shown in FIG. 16 is merely a configuration example of the illumination device 50, and a configuration of the illumination device 50 is not limited thereto. Various optical elements that can be mounted in an existing general illumination device may be further included in the illumination device 50. When a xenon lamp is used as a white light source of the first light source unit 101, for example, a filter that attenuates or removes light of a near-infrared band that can contribute to heating of a biological object during radiation or the like may be provided in the later stage of the first light source unit 101. Alternatively, a filter that attenuates or removes light of a near-infrared band or the like may be provided in the earlier stage of an image sensor used in observation of a subject.

6. FOURTH EMBODIMENT

Another configuration of an illumination device according to the fourth embodiment of the present disclosure will be described with reference to FIG. 19. FIG. 19 is a diagram illustrating a configuration example of the illumination device according to the fourth embodiment. Herein, the illumination device according to the fourth embodiment illustrated in FIG. 19 corresponds to the illumination device 50 according to the third embodiment illustrated in FIG. 16 described above from which the coupling optical system 105, the optical fiber 107, and the third collimator optical system 109 are omitted. Thus, in description regarding the fourth embodiment below, detailed description of overlapping points with the third embodiment will omitted and differences from the third embodiment will mainly be described.

Referring to FIG. 19, the illumination device 60 according to the fourth embodiment includes the first light source unit 101 which radiates white light, the first collimator optical system 103, the second light source unit 120 which includes at least one laser light source that emits light of a predetermined wavelength band, the diffusion member 111, the second collimator optical system 113, the multiplexing member 115c, and the condenser optical system 117. Here, since the configurations and functions of the respective members are the same as those of the respective members shown in FIG. 16, detailed description of the members will be omitted.

In the illumination device 60, white light emitted from the first light source unit 101 is converted into substantially parallel light by the first collimator optical system 103, and is incident on the multiplexing member 115c as in the illumination device 50 according to the fourth embodiment. On the other hand, in the illumination device 60, laser light emitted from the second light source unit 120 is incident directly on the diffusion member 111, and diffused laser light (i.e., laser light from the secondary light source) is converted into substantially parallel light by the second collimator optical system 113 and is incident on the multiplexing member 115c, unlike in the illumination device 50 according to the third embodiment. As in the third embodiment, the effect of improved quality of multiplexed white light can be obtained and thus an observation image can have higher quality even in a more simplified configuration like the illumination device 60.

The configuration of the illumination device 60 according to the fourth embodiment has been described above with reference to FIG. 19. As described above, the same effect as in the third embodiment can be obtained in a more simplified configuration according to the fourth embodiment. Thus, in addition to the effect obtained in the fourth embodiment, miniaturization and reduction in a manufacturing cost of the illumination device 60 can be realized.

As described in the third embodiment above, there is the effect of more uniform luminance distribution of laser light emitted from the optical fiber 107 as the laser light is guided by the optical fiber 107. Thus, it is preferable to provide the optical fiber 107 as in the illumination device 50 according to the third embodiment in order to cause output light to have higher quality. Whether to employ the configuration of the illumination device 50 according to the third embodiment or to employ the configuration of the illumination device 60 according to the fourth embodiment may be appropriately decided by comprehensively taking quality of output light obtained according to applications, a manufacturing cost of a device, and the like into consideration.

7. MODIFIED EXAMPLES

A few modified examples of the third and fourth embodiments described above will be described. Note that, in description regarding the respective modified examples below, a case in which configurations corresponding to the respective modified examples are applied to the illumination device 50 of the third embodiment shown in FIG. 16 will be described as an example; however, the configurations corresponding to the respective modified examples can also be applied to the illumination device 60 of the fourth embodiment likewise.

7-1. Modified Example in which White Light and Laser Light are Multiplexed as Diverging Light A configuration of an illumination device in a modified example in which white light and laser light are multiplexed as diverging light will be described with reference to FIG. 20. FIG. 20 is a diagram illustrating a configuration example of the illumination device when white light and laser light are multiplexed as diverging light.

Herein, the illumination device according to the present modified example shown in FIG. 20 corresponds to the illumination device 50 according to the above-described third embodiment shown in FIG. 16 in which the optical characteristics of the first collimator optical system 103, the second collimator optical system 113, and the condenser optical system 117 are altered. Thus, in description regarding the present modified example below, detailed description of overlapping points with the third embodiment will be omitted, and differences from the third embodiment will mainly be described.

Referring to FIG. 20, the illumination device 70 according to the present modified example includes the first light source unit 101 which radiates white light, a first collimator optical system 103a, the second light source unit 120 which includes at least one laser light source that emits light of a predetermined wavelength band, the coupling optical system 105, the optical fiber 107, the third collimator optical system 109, the diffusion member 111, a second collimator optical system 113a, the multiplexing member 115c, and a condenser optical system 117a. Here, since the configurations and the functions of the first light source unit 101, the second light source unit 120, the coupling optical system 105, the optical fiber 107, the third collimator optical system 109, the diffusion member 111, and the multiplexing member 115c are the same as those of the members shown in FIG. 1, detailed description of the respective members will be omitted.

In the present modified example, the first collimator optical system 103a causes white light emitted from the first light source unit 101 to be incident on the multiplexing member 115c as diverging light rather than completely parallel light. The second collimator optical system 113a causes laser light emitted from the second light source unit 120 and diffused by the diffusion member 111 (i.e., laser light from the secondary light source) to be incident on the multiplexing member 115c as diverging light rather than completely parallel light, along with the white light. The multiplexing member 115c multiplexes the white light and the laser light, both of which are diverging light, and the multiplexed light is coupled to an end of the light guide 130 by the condenser optical system 117a. At this time, the condenser optical system 117a is configured to condense the light from the secondary light source on the incidence end face of the light guide 130 so that the light from the secondary light source fills the area of the incidence end of the light guide 130 as much as possible, as in the third embodiment.

Here, since it is generally necessary to increase a light emitting area of an LED in order to obtain high output, light emitted from an LED has a strong property of being isotropically discharged and does not easily become completely parallel light even when a collimator lens is used. Thus, when a white LED is used as the first light source unit 101 in the third embodiment, it is also difficult to convert white light from the first light source unit 101 into completely parallel light with the first collimator optical system 103. To overcome the difficulty of converting white light into completely parallel light described above, laser light is also set as diverging light along with the white light and both types of light are multiplexed as diverging light in the present embodiment. In light of this point, FIG. 20 can be said to more exactly illustrate the illumination device 70 as the configuration of the illumination device 50 when a white LED is used as the first light source unit 101 in the third embodiment.

In the present modified example, white light and laser light, both of which are set as diverging light, are multiplexed and the multiplexed light is coupled to the end of the light guide 130 by the condenser optical system 117*a*. That is to say, the first collimator optical system 103*a* and the condenser optical system 117*a* are a finite conjugate, as are the second collimator optical system 113*a* and the condenser optical system 117*a*. An optical characteristic of the condenser optical system 117*a* is appropriately designed such that multiplexed light is properly coupled to the incidence end face of the light guide 130 according to optical characteristics of the first collimator optical system 103*a* and the second collimator optical system 113*a*. Accordingly, in the illumination device 70 according to the present modified example, the effect of improving quality of multiplexed white light can be obtained and an observation image can be caused to have higher quality as in the third embodiment.

Note that, although each of the first collimator optical system 103*a*, the second collimator optical system 113*a*, and the condenser optical system 117*a* is illustrated as a convex lens for the sake of convenience in the example illustrated in FIG. 20, a detailed configuration of the optical systems is not limited thereto. The first collimator optical system 103*a*, the second collimator optical system 113*a*, and the condenser optical system 117*a* may each have the above-described functions, and may be configured to be appropriately combined with a known optical element.

The configuration of the illumination device 70 of the modified example in which white light and laser light are multiplexed both as diverging light has been described above. When a white LED is used as the first light source unit 101 and it is difficult to convert white light into completely parallel light as described above, for example, the illumination device 70 which exhibits the same effect as the third embodiment can be configured by appropriately adjusting the optical characteristics of the first collimator optical system 103*a*, the second collimator optical system 113*a*, and the condenser optical system 117*a* as in the present modified example.

7-2. Modified Example in which a Light Source of Another Wavelength Band is Added In the third and fourth embodiments described above, the case in which white light, red laser light, green laser light, and blue laser light are multiplexed has been described. In this configuration, red laser light, green laser light, blue laser light, or mixed light of any of the laser light is used as radiation light in the special observation mode. According to an observation purpose in the special observation mode, however, there can be a desire to use light of another wavelength band that is different from that of the laser light as radiation light. Herein, as a modified example of the third and fourth embodiments, a configuration of an illumination device in a case in which a light source of another wavelength band is added to the illumination device 50 according to the third embodiment will be described.

The configuration of the illumination device of the modified example to which a light source of another wavelength band is added will be described with reference to FIG. 21. FIG. 21 is a diagram illustrating a configuration example of the illumination device when a light source of another wavelength band is added thereto.

Here, the illumination device according to the present modified example illustrated in FIG. 21 corresponds to the illumination device 50 according to the above-described third embodiment shown in FIG. 16 to which a third light source unit 119 to be described below is added. Thus, in description regarding the present modified example below, detailed description regarding overlapping points with the third embodiment will be omitted and differences from the third embodiment will mainly be described.

Referring to FIG. 21, the illumination device 80 according to the present modified example includes the first light source unit 101 which radiates white light, the first collimator optical system 103, the second light source unit 120 which includes at least one laser light source that emits light of a predetermined wavelength band, the coupling optical system 105, the optical fiber 107, the third collimator optical system 109, the diffusion member 111, the second collimator optical system 113, the multiplexing member 115*c*, the condenser optical system 117, the third light source unit 119, and the dichroic mirror 125. Here, since configurations and functions of the respective members other than the third light source unit 119 and the dichroic mirror 125 are the same as those of the members shown in FIG. 16, detailed description regarding those members will be omitted.

As illustrated, the illumination device 80 according to the modified example is provided with the dichroic mirror 125 in the middle of the optical path from the first light source unit 101 to the multiplexing member 115*c*. In addition, the third light source unit 119 is provided such that emitted light is incident on the dichroic mirror 125 from the direction substantially perpendicular to the optical path from the first light source unit 101 to the multiplexing member 115*c*.

The third light source unit 119 emits light of a wavelength band that is different from that of laser light emitted from the second light source unit 120. Here, a case in which the third light source unit 119 is configured as an LED which emits ultraviolet light having the center wavelength of 410 nm will be described as an example. Note that, although not illustrated for the sake of simplification, a collimator lens or the like which causes light emitted from the third light source unit 119 to be substantially parallel light and to be incident on the dichroic mirror 125 is provided in the later stage of the third light source unit 119.

The dichroic mirror 125 has characteristics of transmitting white light emitted from the first light source unit 101 and reflecting ultraviolet light of around the wavelength of 410 nm emitted from the third light source unit 119. Accordingly, the dichroic mirror 125 multiplexes white light and ultraviolet light, and the multiplexed light is incident on the multiplexing member 115*c*.

The polarizing beam splitter 141 of the multiplexing member 115c has the characteristic of reflecting light that has passed through the first polarization conversion element 142 and transmitting light that has passed through the second polarization conversion element 143 as in the third embodiment. Thus, light generated by multiplexing white light and ultraviolet light that have passed through the first polarization conversion element 142 and laser light that has passed through the second polarization conversion element 143 are multiplexed by the polarizing beam splitter 141 in the present modified example. In this manner, in the illumination device 80 according to the present modified example, light generated by superimposing ultraviolet light on output light of the illumination device 50 according to the third embodiment can be output as multiplexed white light.

The configuration of the illumination device 80 of the modified example in which a light source of another wavelength band is added has been described above with reference to FIG. 21. According to the present modified example as described above, light obtained by superimposing emitted light from the third light source unit 119 on output light of the illumination device 50 according to the third embodiment can be output as multiplexed white light. Since the multiplexed white light is generated in the same manner as in the third embodiment except that the emitted light from the third light source unit 119 is added, the effect of improving quality of the multiplexed white light that is used as radiation light in the normal observation mode or the normal/special observation mode can be obtained and an observation image can be caused to have higher quality in the illumination device 80 according to the present modified example as in the third embodiment. On the other hand, in the special observation mode, by driving only the third light source unit 119, ultraviolet light can be radiated to an operative field according to an observation purpose. Since light of a wavelength band can be more properly output according to an observation purpose while realizing the effect obtained in the third embodiment in the present modified example as described above, the illumination device 80 which can correspond to greater diversity of applications is realized.

Here, when a light source of still another wavelength band is added, a configuration in which a laser light source is added to the second light source unit 120 can also be considered. For example, the same output light as that of the illumination device 80 can be obtained even if a laser light source that emits laser light of a wavelength band corresponding to ultraviolet light is added to the second light source unit 120 in the above-described example. A laser light source, however, generally tends to be more expensive than an LED and to be configured in a large size. By configuring the third light source unit 119 with an LED as in the illustrated configuration, the illumination device 80 can be realized with a lower cost in a smaller size.

Note that reflection and transmission characteristics of the dichroic mirror 125 may be set to be reversed with respect to the above-described characteristics. In this case, ultraviolet light that the dichroic mirror 125 transmits and white light reflected by the dichroic mirror 125 are multiplexed and the multiplexed light is incident on the multiplexing member 115c. In addition, as in the third embodiment, reflection and transmission characteristics of the multiplexing member 115c may be set to be reversed with respect to the above-described characteristics.

In addition, the dichroic mirror 125 is an example of a multiplexing member for multiplexing white light and ultraviolet light, and multiplexing of white light and ultraviolet light may also be performed by a multiplexing member of another type, for example, a polarizing beam splitter, or the like.

In addition, the configurations according to the third and fourth embodiments and the respective modified examples described above may be combined with each other in a possible range. Herein, as described in (7-1. Modified example in which white light and laser light are multiplexed as diverging light), it is generally difficult to make emitted light from an LED into completely parallel light even if a collimator lens is used. Thus, in the configuration example illustrated in FIG. 21, when an LED is used as the first light source unit 101 and/or the third light source unit 119, emitted light from the units can be diverging light, rather than completely parallel light. Thus, when an LED is used as the first light source unit 101 and/or the third light source unit 119 in the configuration example illustrated in FIG. 21, it is preferable to appropriately adjust the optical characteristics of the first collimator optical system 103, the second collimator optical system 113, and the condenser optical system 117 in combination with the configuration example illustrated in FIG. 20 in order to deal with diverging light.

8. APPLICATION EXAMPLES

Application examples of the illumination devices 50, 60, 70, and 80 according to the third and fourth embodiments and the respective modified examples described above will be described. Herein, as an application example, a case in which the illumination devices 50, 60, 70, and 80 are applied to an observation device that can execute photodynamic diagnosis (PDD) and photodynamic therapy (PDT) will be described.

First, PDD and PDT will be described below. Then, an existing general observation device that can execute PDD and PDT will be described, and a disadvantage of such a general observation device will be described. Next, a configuration example and an operation example of an observation device to which the illumination device 50, 60, 70, and 80 are applied will be described.

(8-1. Regarding PDD and PDT)

PDD and PDT are for less invasive tumor diagnosis and medical treatment using photosensitive pharmaceutical agents, and have been applied to diagnosis and treatment of early liver cancer, early esophageal cancer, gastric cancer, early cervical cancer, cerebral malignancy, and the like.

In PDD, the property of a photosensitive pharmaceutical agent that emits fluorescence when it is excited by excitation light of a predetermined wavelength band is used. Since a photosensitive pharmaceutical agent administered to a patient has the property of accumulating in a tumor selectively, a tumor site can be diagnosed by radiating excitation light to an operative field and detecting fluorescence emitted from a photosensitive pharmaceutical agent.

In PDT, the property of a photosensitive pharmaceutical agent that generates active oxygen when it is irradiated with excitation light of a predetermined wavelength band is used. Since a photosensitive pharmaceutical agent administered to a patient has the property of accumulating in a tumor selectively as described above, a tumor site can be treated by radiating excitation light to an operative field to generate active oxygen mainly in the tumor site to cause degeneration of the tumor site and eventually cell death. Radiation of excitation light for performing PDD and PDT corresponds to an operation of the illumination device 50, 60, 70, or 80 in the special mode of the above-described embodiments.

When only excitation light is radiated to an operative field, a tumor site can be observed, but it is not possible to observe a normal state of the entire operative field. Thus, there is generally an observation device which can execute PDD and PDT having a function of switching or simultaneously performing radiation of white light for performing normal observation and radiation of excitation light for performing PDD and PDT.

For example, JP 2006-000157A (hereinafter referred to as Reference Literature 1) discloses a light source device for an observation device (endoscope device) that can switch radiation of white light for normal observation and radiation of laser light (excitation light) for fluorescence observation. In the technology described in Reference Literature 1, a dichroic mirror with a characteristic of transmitting white light emitted from a white light source and reflecting most excitation light from a laser light source guides white light and excitation light on the same optical axis. Then, by appropriately controlling movement of a shield plate provided in a later stage of the white light source and driving of the laser light source, the white light or the excitation light is incident on an end of a light guide. In this manner, the light source device described in Reference Literature 1 is configured to be able to switch to the normal observation mode and the special observation mode. Note that Reference Literature 1 is the same literature as PTL 9 described above.

For example, JP 2006-296516A (hereinafter referred to as Reference Literature 2) discloses an observation device (endoscope device) with which bright field observation is possible on a peripheral region of a lesion part emitting fluorescence by providing a white light source for normal observation near an intake of observation light (i.e., fluorescence) at the time of fluorescence observation. In the technology described in Reference Literature 2, the white light source that emits visible light which has an intensity of a wavelength band corresponding to fluorescence emitted from the lesion part relatively shorter than other wavelength bands or is cut by a filter is used as a light source provided in the intake of observation light, and thus the lesion part emitting fluorescence and the peripheral region thereof can be simultaneously observed. In this manner, the observation device described in Reference Literature 2 is configured to perform observation of an operative field in the normal/special observation mode.

For example, JP 2009-226067A (hereinafter referred to as Reference Literature 3) discloses an observation device having a white light source and a rotary filter in which a plurality of filters which each extract light of a predetermined wavelength band from white light emitted from the white light source are provided in different regions within a plane. In the technology described in Reference Literature 3, the rotary filter is provided with a first filter which extracts light from white light according to a wavelength band of excitation light which corresponds to a first photosensitive pharmaceutical agent, a second filter which extracts light from the white light corresponding to a wavelength band of excitation light which corresponds to a second photosensitive pharmaceutical agent, and a third filter which extracts light from the white light according to a wavelength band of visible light. In addition, radiation of excitation light and radiation of visible light are switched by controlling a rotation angle of the rotary filter and switching a filter through which white light passes. In this manner, the observation device disclosed in Reference Literature 3 is configured to switch to the normal observation mode and the special observation mode.

In the technology disclosed in Reference Literature 1, however, a use method of simultaneously radiating white light and excitation light (i.e., use method corresponding to the normal/special observation mode) is not assumed, and white light and excitation light are radiated in a time-sharing manner. Thus, it is necessary to provide a shield plate which shields white light as described above and a driving mechanism of the shield plate, and thus there is a possibility of a device becoming complicated and growing in size. In addition, in terms of a configuration of a device, white light which is incident on a light guide via a dichroic mirror is white light of which a wavelength component corresponding to excitation light is cut or attenuated and has a different hue from original white light, and thus there is concern of a high-quality observation image not being obtained at the time of normal observation. In addition, a light detector which detects an intensity of excitation light is provided in the light source device disclosed in Reference Literature 1 for the purpose of adjusting the output of a laser light source; however, since the light detector is configured such that white light can also reach the light detector, there is concern of a detection value of the light detector including an overlap of the intensity of excitation light and the intensity of white light, the output of the laser light source is not properly controlled, and therefore a high-quality observation image is not obtained at the time of fluorescence observation.

In addition, in the technology disclosed in Reference Literature 2, an optical path of white light for normal observation is different from an optical path of excitation light for fluorescence observation, and radiation angles of both types of light to an operative field are also different. Thus, a shadow appearing in an observation image due to the shape of an operative field can change between normal observation and fluorescence observation. Thus, there is a possibility of a situation in which, during fluorescence observation, a shadow is produced at a site at which a shadow is not found during normal observation. Since a portion in which a shadow is produced during fluorescence observation is one that excitation light does not reach, a portion set for fluorescence observation during normal observation is not observed during actual fluorescence observation, and thus there is concern of it being difficult to perform proper observation in response to a desire of a user.

In addition, in the technology disclosed in Reference Literature 3, a use method of simultaneously radiating white light and excitation light (i.e., a use method corresponding to the normal/special observation mode) is not assumed and white light and excitation light are radiated in a time-sharing manner as in the technology disclosed in Reference Literature 1. Although radiation of white light or excitation light is realized in a time-sharing manner using a rotary filter in the technology disclosed in Reference Literature 3 as described above, the rotary filter and a driving mechanism of the rotary filter are necessary, and thus there is a possibility of a device becoming complicated and growing in size.

As described above, in the existing general technologies, a configuration in which normal observation and/or fluorescence observation are executed in a simpler way and an observation image of higher quality can be acquired in normal observation and/or fluorescence observation was not sufficiently examined. On the other hand, according to an embodiment of the present disclosure, execution of normal observation and/or fluorescence observation with a simpler configuration and obtaining an observation image of higher quality in normal observation and/or fluorescence observation can be simultaneously achieved by applying the illumination devices 50, 60, 70, and 80 according to the third and fourth embodiments and the respective modified examples described above to an observation device. Configuration examples of observation devices to which the illumination devices 50, 60, 70, and 80 are applied will be described in detail below.

8-2. Endoscope Device 8-2-1. Configuration of an Endoscope Device

A configuration of an endoscope device to which the illumination devices 50, 60, 70, and 80 are applied will be described with reference to FIGS. 22 and 23. FIG. 22 is a diagram illustrating a configuration example of the endoscope device to which the illumination devices 50, 60, 70, and 80 according to the third and the fourth embodiments and the respective modified examples are applied. FIG. 23 is a graph for describing a characteristic of light multiplexed by a multiplexing member of the endoscope device illustrated in FIG. 22.

Note that, in description below, a case in which the configuration corresponding to the illumination device 60 according to the fourth embodiment is mounted in the endoscope device will be described as an example. The present application example, however, is not limited thereto, and configurations corresponding to other illumination devices 50, 70, and 80 may be mounted in the endoscope device.

Referring to FIG. 22, the endoscope device 3 includes an illumination device 3100, an endoscope unit 1200, an image processing device 1300, and a display device 1400. Note that, in FIG. 22, an observation site 1500 to which output light from the illumination device 3100 is radiated is also schematically illustrated.

Illumination Device 3100

The illumination device 3100 generates white light (multiplexed white light) for normal observation and excitation light for fluorescence observation. Multiplexed white light and/or excitation light generated by the illumination device 1100 are incident on the light guide 130, guided into a lens barrel 1210 to be described below by the light guide 130, and then radiated to the observation site 1500 from the front end of the lens barrel 1210.

Here, the illumination device 3100 corresponds to the illumination device 60 according to the above-described fourth embodiment. Several members, however, are added to illumination device when it is mounted in the endoscope device 3.

Specifically, the illumination device 3100 includes the first light source unit 101 which radiates white light, the first collimator optical system 103, a second light source unit 120*b* which includes at least one laser light source that emits light of a predetermined wavelength band, the diffusion member 111, the second collimator optical system 113, a multiplexing member 115*c*, the condenser optical system 117, a laser line filter 1101, a half mirror 1103, a light detector 1105, another half mirror 1107, another light detector 1109, and a control unit 1120.

As described above, the illumination device 3100 corresponds to the illumination device 60 according to the fourth embodiment to which the laser line filter 1101, the half mirror 1103, the light detector 1105, the half mirror 1107, and the light detector 1109 are added, and in which the optical characteristics of the second light source unit 120 have been altered. Since the configurations and functions of other members are the same as those of the respective members shown in FIG. 19, detailed description of the respective members is omitted. In addition, the control unit 1120 corresponds to the control unit which controls driving of the first light source unit 101 and the second light source unit 120*b*, not illustrated in FIG. 19.

Here, the second light source unit 120*b* corresponds to the second light source unit 120 of the illumination device 60 in which the wavelength band of emittable laser light is altered. Since other configurations and functions of the second light source unit 120*b* are the same as those of the members of the illumination device 60, detailed description of the second light source unit 120*b* regarding overlapping points with those described above will be omitted.

Note that, although illustration of the second light source unit 120*b* is simplified in FIG. 22, the second light source unit 120*b* includes at least one laser light source, the same as the second light source unit 120 illustrated in FIG. 19. As at least one laser light source included in the second light source unit 120*b*, however, one that can emit laser light of a wavelength band that is used as excitation light in PDD and PDT is mounted.

The laser line filter 1101 is provided between, for example, the third collimator optical system 109 and the diffusion member 111 as illustrated. The laser line filter 1101 is a so-called band-pass filter (BPF) which only transmits light of wavelength bands other than a predetermined wavelength band. The laser line filter 1101 is set to remove the spectrum except for a laser oscillation wavelength (for example, a natural emission light component of a laser light source included in the second light source unit 120 or the like). When laser light emitted from the second light source unit 120*b* passes through the laser line filter 1101, a component of an extra wavelength band which can be noise in an observation image is removed from the laser light, and only a component of a wavelength band corresponding to excitation light is extracted from the laser light.

The half mirror 1103 is provided in the later stage of the laser line filter 1101. Part of laser light demultiplexed by the half mirror 1103 is incident on the light detector 1105. The light detector 1105 has a function of detecting an intensity of light, and the value of detection is provided to a second-light-source-unit driving control unit 1123 of the control unit 1120 to be described below. The second-light-source-unit driving control unit 1123 controls driving of each laser light source of the second light source unit 120*b* based on the detection value so that, for example, a total output of laser light from the second light source unit 120*b* becomes constant. By providing the configuration for monitoring the output of laser light emitted from the second light source unit 120*b* as described above, the output can be set to be more stable.

The half mirror 1107 is provided on the optical path from the first light source unit 101 to the multiplexing member 115*c*. Part of white light demultiplexed by the half mirror 1107 is incident on the light detector 1109. The light detector 1109 has a function of detecting an intensity of light, and the value of the detection is provided to a first-light-source-unit driving control unit 1121 of the control unit 1120 to be described below. The first-light-source-unit driving control unit 1121 controls driving of the white light source of the first light source unit 101 based on the detection value so that, for example, the output of white light from the first light source unit 101 becomes constant. By providing the configuration for monitoring the output of white light from the first light source unit 101 as described above, the output can be set to be more stable.

Note that the half mirrors 1103 and 1107 are an example of a demultiplexing member, and other demultiplexing members may be used in place of the half mirrors 1103 and 1107. In addition, as the light detectors 1105 and 1109, various known light detectors may be used.

The control unit 1120 comprehensively controls operations of the illumination device 3100. The control unit 1120 includes the first-light-source-unit driving control unit 1121 and the second-light-source-unit driving control unit 1123 as its functions. The control unit 1120 includes a processor, for example, a central processing unit (CPU), a digital signal processor (DSP), or the like, a microcomputer in which such a processor is mounted, and the like, and each of the functions of the control unit 1120 is realized when the processor executes an arithmetic operation process according to a predetermined program.

The first-light-source-unit driving control unit 1121 controls the output of light emission of the first light source unit 101. Specifically, the first-light-source-unit driving control unit 1121 can control the output of light emission by changing a driving current of the white light source (for example, a white LED) of the first light source unit 101. As described above, the first-light-source-unit driving control unit 1121 can monitor an intensity of white light based on a detection value of the light detector 1109 and can control driving of the first light source unit 101 so that the intensity of white light becomes constant.

The second-light-source-unit driving control unit 1123 controls the output of light emission of the second light source unit 120b. Specifically, the second-light-source-unit driving control unit 1123 can control the output of light emission by changing a driving current of the laser light source of the second light source unit 120b. As described above, the second-light-source-unit driving control unit 1123 can monitor an intensity of laser light based on a detection value of the light detector 1105 and control driving of the second light source unit 120b so that the intensity of laser light becomes constant.

In addition, the second-light-source-unit driving control unit 1123 may further have a function of controlling an oscillation wavelength of the laser light source to be constantly maintained by constantly maintaining a device temperature of the laser light source of the second light source unit 120b. For example, the device temperature of the laser light source can be constantly maintained by a thermoelectric cooler and a temperature-measuring element included in the laser light source, in which the second-light-source-unit driving control unit 1123 controls driving of the thermoelectric cooler based on temperature measurement information by the temperature-measuring element.

Examples of excitation light wavelengths and fluorescence wavelengths of photosensitive pharmaceutical agents used in PDD and PDT are shown in Table 3 below. In the present configuration example, the second light source unit 120b is configured to emit laser light corresponding to the excitation light wavelength of a photosensitive pharmaceutical agent to be used.

TABLE 3

| Pharmaceutical agent | Excitation light wavelength | Fluorescence wavelength |
|---|---|---|
| 5-ALA | 405 nm | 635 nm |
| Laserphyrin | 664 nm | 672 nm |

A configuration and an operation of the endoscope device 3 when Laserphyrin is used as a photosensitive pharmaceutical agent will be described below as an example. In addition, the second light source unit 120b multiplexes and emits laser light of three different wavelength bands in the configuration example described in (6. Fourth embodiment) described above; however, in order to simplify description, the second light source unit 120b will be described as only emitting laser light of a wavelength band corresponding to the excitation light wavelength of Laserphyrin. This corresponds to a state in which, among a plurality of laser light sources included in the second light source unit 120b, only a laser light source that can emit laser light corresponding to the excitation light wavelength of Laserphyrin is driven.

The characteristic of light multiplexed by the multiplexing member 115c when Laserphyrin is used as a photosensitive pharmaceutical agent will be described with reference to FIG. 23. In FIG. 23, the spectrum of white light emitted from the first light source unit 101 and the spectrum of laser light emitted from the second light source unit 120b are shown.

As shown, the white light emitted from the first light source unit 101 has a wide-band light emission spectrum including the wavelength bands of approximately 400 nm to 750 nm. On the other hand, the laser light emitted from the second light source unit 120b has a narrow-band light emission spectrum in which the oscillation peak wavelength corresponds to the excitation light wavelength of Laserphyrin (664 nm).

The multiplexing member 115c multiplexes the white light emitted from the first light source unit 101 and the laser light emitted from the second light source unit 120b by setting the polarization directions of the light to be orthogonal to each other. Thus, the light multiplexed by the multiplexing member 115c is white light (i.e., multiplexed white light) generated by superimposing the component of the wavelength band corresponding to the excitation light wavelength of Laserphyrin on the white light. The spectrum of the multiplexed light is the overlap of the broadband spectrum of the illustrated white light and the narrowband spectrum corresponding to the excitation light wavelength of Laserphyrin.

Endoscope Unit 1200

The endoscope unit 1200 includes the lens barrel 1210 and an imaging unit 1220. In the present configuration example, the endoscope unit 1200 is configured as a rigid endoscope. The lens barrel 1210 has a substantially cylindrical shape, in which the light guide 130 (i.e., a light guiding member) extends to the front end thereof. When the lens barrel 1210 is inserted into the body cavity of a patient and light guided through the light guide 130 (i.e., output light from the illumination device 3100) is radiated thereto from the front end part, the white light and/or excitation light is radiated to the observation site 1500.

When the white light and/or excitation light is radiated to the observation site 1500, reflected light in the radiation is guided inside the lens barrel 1210 in the reverse direction, and then reaches the imaging unit 1220. In FIG. 22, propagation of the light in the imaging unit 1220 is schematically illustrated with dashed-line arrows.

The imaging unit 1220 includes an optical filter 1221, a first image sensor 1223, and a second image sensor 1225. Upon reaching the imaging unit 1220, the reflected light from the observation site 1500 is incident on the optical filter 1221.

The optical filter 1221 is a spectroscopic element such as a dichroic mirror, and is configured to transmit light of a wavelength of, for example, 670 nm or longer and cause the light to be incident on the first image sensor 1223, and to reflect light of a wavelength band shorter than 670 nm and cause the light to be incident on the second image sensor

1225. Thus, the first image sensor 1223 does not receive excitation light of Laserphyrin (the wavelength of 664 nm), but receives fluorescence of Laserphyrin (the wavelength of 672 nm). In this manner, the optical filter 1221 is configured to cause only fluorescence of a pharmaceutical agent among excitation light of the pharmaceutical agent and fluorescence of the pharmaceutical agent to be incident on one image sensor (the first image sensor 1223 in the illustrated example).

The first image sensor 1223 and the second image sensor 1225 are image sensors with which color imaging is possible. Although types of the first image sensor 1223 and the second image sensor 1225 are not limited, various known image sensors, for example, a charge coupled device (CCD) image sensor, a complementary metal-oxide-semiconductor (CMOS) image sensor, and the like can be used as the first image sensor 1223 and the second image sensor 1225.

The output of the first image sensor 1223 is input to a long-wavelength band image generation unit 1301 of the image processing device 1300 to be described later. In addition, the output of the second image sensor 1225 is input to a short-wavelength band image generation unit 1303 of the image processing device 1300 to be described later.

Image Processing Device 1300

The image processing device 1300 generates a captured image (observation image) of the observation site 1500 based on reflected light from the observation site 1500 detected by the imaging unit 1220. The image processing device 1300 includes the long-wavelength band image generation unit 1301, the short-wavelength band image generation unit 1303, and an observation image generation unit 1305, and an input unit 1307 as its functions. The image processing device 1300 includes a processor, for example, a CPU or a DSP, a microcomputer in which such a processor is mounted, or the like, and each function of the image processing device 1300 is realized as the processor executes an arithmetic operation process according to a predetermined program. For example, the image processing device 1300 may be an information processing device such as a personal computer (PC) in which a processor or a microcomputer is mounted.

The long-wavelength band image generation unit 1301 generates an image of the observation site 1500 based on an output signal from the first image sensor 1223. The image generated by the long-wavelength band image generation unit 1301 is hereinafter also referred to as a first image. Since the first image sensor 1223 receives light of a wavelength of 670 nm or longer using the optical filter 1221, the long-wavelength band image generation unit 1301 generates the first image based on light of a relatively long wavelength band of which the wavelength is 670 nm or longer. In this manner, the long-wavelength band image generation unit 1301 generates the first image based on light of a wavelength band that is a longer wavelength band than the excitation light wavelength including the fluorescence wavelength.

The short-wavelength band image generation unit 1303 generates an image of the observation site 1500 based on an output signal from the second image sensor 1225. The image generated by the short-wavelength band image generation unit 1303 is hereinafter also referred to as a second image. Since the second image sensor 1225 receives light of a wavelength shorter than 670 nm using the optical filter 1221, the short-wavelength band image generation unit 1303 generates the second image based on light of a relatively short wavelength band of which the wavelength is shorter than 670 nm. In this manner, the short-wavelength band image generation unit 1303 generates the second image based on light of a wavelength band that is a shorter wavelength band than the fluorescence wavelength including the excitation light wavelength.

The observation image generation unit 1305 generates an observation image based on at least any of the first image generated by the long-wavelength band image generation unit 1301 and the second image generated by the short-wavelength band image generation unit 1303. The image generated by the observation image generation unit 1305 becomes the observation image of the observation site 1500 that is finally visible to a user. Here, specific processes of the observation image generation unit 1305 differ according to observation modes. Details of the processes of the observation image generation unit 1305 will be described again in (8-2-2. Operation of the endoscope device) below. The observation image generation unit 1305 transmits information regarding the generated image to a display device 1400.

The input unit 1307 is an input interface that receives operation inputs of the user. The input unit 1307 is configured with an input device operated by the user, for example, a mouse, a keyboard, a touch panel, a button, a switch, a lever, or the like. The user can input various kinds of information and various instructions to the endoscope device 3 via the input unit 1307.

For example, the user can input an instruction to select any of the normal observation mode, the special observation mode, and the normal/special observation mode as an observation mode to the endoscope device 3 via the input unit 1307. Information regarding the selected observation mode is input to the observation image generation unit 1305 and the first-light-source-unit driving control unit 1121 and the second-light-source-unit driving control unit 1123 of the illumination device 3100, and the observation image generation unit 1305, the first-light-source-unit driving control unit 1121, and the second-light-source-unit driving control unit 1123 generate an image or drive the first light source unit 101 and the second light source unit 120 according to the selected observation mode.

In addition, for example, the user can input an instruction regarding intensity of emitted light from the first light source unit 101 and the second light source unit 120 of the illumination device 3100 to the endoscope device 1 via the input unit 1307. Information regarding the input intensity is input to the first-light-source-unit driving control unit 1121 and the second-light-source-unit driving control unit 1123 of the illumination device 3100, and the first-light-source-unit driving control unit 1121 and the second-light-source-unit driving control unit 1123 drive the first light source unit 101 and the second light source unit 120 so that the instructed intensity is realized.

Display Device 1400

The display device 1400 displays images generated by the observation image generation unit 1305 of the image processing device 1300. A type of the display device 1400 is not limited, and the display device 1400 may be, for example, a CRT display device, a liquid crystal display device, a plasma display device, an EL display device, or the like. The user performs diagnosis or treatment of the observation site 1500 by visually recognizing an image displayed on the display device 1400.

The configuration example of the endoscope device 3 to which the illumination device 60 is applied has been described above with reference to FIGS. 22 and 23. Note that the configuration of the endoscope device 3 illustrated in FIG. 22 is merely an example, and a detailed configuration of the endoscope device 3 may be appropriately modified within the scope in which the above-described functions are realized. For example, the endoscope device 3 may be further provided with various optical elements included in an existing general endoscope device in addition to the illustrated configuration.

In addition, the functions of the control unit 1120 of the illumination device 3100 and the functions of the image processing device 1300 may not necessarily be provided in each device as illustrated, and the functions may be executed by either device. For example, some or all of the functions of the control unit 1120 may be provided in the image processing device 1300. Alternatively, some or all of the functions of the image processing device 1300 may be provided in the illumination device 3100. In addition, an input of an instruction regarding driving of the illumination device 4100 is performed via the input unit 1307 provided in the image processing device 1300 in the above-described example; however, the same function as the input unit 1307 may be provided in the illumination device 4100 and the user may input various instructions to the illumination device 4100 via the input unit.

8-2-2. Operations of the Endoscope Device

Operations of the endoscope device 3 according to observation modes mentioned above will be described. In the endoscope device 3, any of the normal observation mode, the special observation mode, and the normal/special observation mode can be selected as an observation mode.

Normal Observation Mode

In the normal observation mode, light of a broadband corresponding to visible light in the range of approximately 400 nm to 750 nm is radiated to the observation site 1500 and an image of the observation site 1500 is acquired. When the user inputs an instruction to select the normal observation mode as an observation mode via the input unit 1307, the first-light-source-unit driving control unit 1121 and the second-light-source-unit driving control unit 1123 of the illumination device 3100 drive the first light source unit 101 and the second light source unit 120*b* together according to the instruction.

At this time, output light from the illumination device 3100 is light (multiplexed white light) generated by multiplexing white light from the first light source unit 101 and laser light from the second light source unit 120*b* as illustrated in FIG. 23. Here, in the normal observation mode, the multiplexed white light can be adjusted within a possible range so that the multiplexed white light has a predetermined hue set in advance by a user (for example, a similar hue to white light from various standard illuminants) by, for example, appropriately controlling the output of the white light from the first light source unit 101 and the output of the laser light from the second light source unit 120*b*.

In the imaging unit 1220, light of a wavelength of 670 nm or longer is incident on the first image sensor 1223 and light of a wavelength shorter than 670 nm is incident on the second image sensor 1225 as described above. Thus, the long-wavelength band image generation unit 1301 of the image processing device 1300 generates an image as the first image based on light of a red band with a wavelength of 670 nm or longer. In addition, the short-wavelength band image generation unit 1303 generates an image as the second image based on light of a red band, a green band, and a blue band with a wavelength shorter than 670 nm.

In the normal observation mode, the observation image generation unit 1305 generates a combined image by summing up the RGB values of the first image generated by the long-wavelength band image generation unit 1301 and the RGB values of the second image generated by the short-wavelength band image generation unit 1303. The combined image generated in this way is a normal observation image corresponding to radiation light of a visible light band (about 400 nm to 750 nm).

Note that, although the case in which the first light source unit 101 and the second light source unit 120 are driven together in the normal observation mode has been described in the example described above, an operation of the endoscope device 3 in the normal observation mode is not limited thereto. For example, only the first light source unit 101 may be driven in the normal observation mode. In this case, white light emitted from the first light source unit 101 is radiated to the observation site 1500 as it is.

In addition, although the case in which the second light source unit 120*b* only emits laser light of the wavelength band corresponding to the excitation light wavelength of Laserphyrin has been described in the above example, the present application example is not limited thereto. For example, the second light source unit 120*b* may be configured to be capable of emitting red laser light, green laser light, and blue laser light which correspond to the three primary colors of light in addition to laser light of the wavelength band which corresponds to the excitation light wavelength of Laserphyrin, like the second light source unit 120 of the illumination devices 50, 60, 70, and 80. In this case, by appropriately controlling the output of the laser light of each color, the color temperature of the multiplexed white light can be adjusted so that the hue of white light from any of various light sources is reproduced. Note that such adjustment of color temperature of multiplexed white light using red laser light, green laser light, and blue laser light may also be performed in the normal/special observation mode to be described below.

Special Observation Mode

In the special observation mode, narrow-band light corresponding to the excitation light wavelength of Laserphyrin that is a photosensitive pharmaceutical agent is radiated to the observation site 1500 and an image based on fluorescence from the observation site 1500 is acquired. The special observation mode is an observation mode used when PDD and PDT are performed.

When a user inputs an instruction to select the special observation mode as an observation mode via the input unit 1307, only the second light source unit 120*b* is driven by the second-light-source-unit driving control unit 1123 of the illumination device 3100 according to the instruction.

At this time, the output light from the illumination device 3100 is light without the spectrum of white light in the spectrum shown in FIG. 23, i.e., laser light having the excitation light wavelength of Laserphyrin as the center wavelength. Note that, generally in PDT, excitation light with a stronger intensity is radiated to the observation site 1500 than in PDD. Thus, when PDT is performed in the special observation mode, the output of laser light from the second light source unit 120*b* is set to be stronger than when PDD is performed.

In the imaging unit 1220, light having a wavelength of 670 nm or longer is incident on the first image sensor 1223 and light having a wavelength shorter than 670 nm is incident on the second image sensor 1225 as described above. Thus, the long-wavelength band image generation unit 1301 of the image processing device 1300 generates an image based on light in a red band with a wavelength of 670 nm or longer as the first image.

Here, since the fluorescence wavelength of Laserphyrin is 672 nm, the first image generated by the long-wavelength band image generation unit 1301 is an image based on fluorescence of Laserphyrin, i.e., an image in which a tumor that is an observation target in the special observation mode is selectively visible. Thus, in the special observation mode, the observation image generation unit 1305 outputs the first image generated by the long-wavelength band image generation unit 1301, i.e., the fluorescence observation image to the display device 1400.

Normal/Special Observation Mode

In the normal/special observation mode, by simultaneously performing radiation of white light for normal observation and radiation of excitation light for special observation, recognition of the shape of an operative field based on a normal observation image and fluorescence observation of a tumor based on a special observation image can be simultaneously performed. In this manner, by performing observation in the normal/special observation mode, the position of a tumor in an operative field can be easily determined.

When a user inputs an instruction to select the normal/special observation mode as an observation mode through the input unit 1307, the first-light-source-unit driving control unit 1121 and the second-light-source-unit driving control unit 1123 of the illumination device 3100 drive the first light source unit 101 and the second light source unit 120b together according to the instruction. At this time, the output light from the illumination device 1100 is light generated by multiplexing the white light from the first light source unit 101 and laser light from the second light source unit 120b (multiplexed white light) as shown in FIG. 23. Unlike in the normal observation mode, however, the output of the laser light from the second light source unit 120b is adjusted to a value according to PDD and PDT in the normal/special observation mode. Note that, in this case, when PDT is performed, the output of laser light from the second light source unit 120b is set to be stronger than when PDD is performed, like in the special observation mode.

In the imaging unit 1220, light of a wavelength of 670 nm or longer is incident on the first image sensor 1223 and light of a wavelength shorter than 670 nm is incident on the second image sensor 1225 as described above. Thus, the long-wavelength band image generation unit 1301 of the image processing device 1300 generates an image as the first image based on light of a red band with a wavelength of 670 nm or longer. In addition, the short-wavelength band image generation unit 1303 generates an image as the second image based on light of a red band, a green band, and a blue band with a wavelength shorter than 670 nm.

Here, since the fluorescence wavelength of Laserphyrin is 672 nm, the first image generated by the long-wavelength band image generation unit 1301 is an image based on fluorescence of Laserphyrin, i.e., an image in which a tumor is selectively visible. On the other hand, a red component of the second image generated by the short-wavelength band image generation unit 1303 is considered to be based on a component corresponding to the excitation light wavelength of Laserphyrin of radiation light. The red component of the second image can be said to be a component that hinders fluorescence observation of a tumor.

Thus, the observation image generation unit 1305 generates a combined image in the normal/special observation mode by summing up an R value of the first image generated by the long-wavelength band image generation unit 1301 and GB values of the second image generated by the short-wavelength band image generation unit 1303. The combined image generated in this manner is an image in which a normal observation image based on the GB values of the second image and a fluorescence observation image based on the R value of the first image overlap. In the image, a tumor is displayed in red in the normal observation image based on the GB values.

Note that, although the case in which the first light source unit 101 and the second light source unit 120 are driven together in the normal/special observation mode has been described in the above-described example, an operation of the endoscope device 3 in the normal/special observation mode is not limited thereto. For example, by alternately executing an operation in the normal observation mode and an operation in the special observation mode described above continuously in a time sharing manner to obtain a normal observation image and a fluorescence observation image and combining the images using the observation image generation unit 1305, an image in which the normal observation image and the fluorescence observation image overlap may be acquired.

In addition, in the finally obtained image of the above-described example, a tumor can be displayed in red in the normal observation image based on the GB values. The tumor displayed in red, however, is not necessarily easily visible to the user. Thus, based on a desire of the user, another image process may be performed by the observation image generation unit 1305 to appropriately change a display color of a tumor. Accordingly, visibility of a tumor for the user can be further improved.

The configuration and the operation of the endoscope device 3 with which the illumination device 3100 having substantially the same configuration as the illumination device 60 according to the fourth embodiment is incorporated have been described above. As the illumination device 3100 is used as a light source of the endoscope device 3, the following effect can be obtained as the illumination device 60.

That is to say, in the illumination device 3100, the diffusion member 111 is provided on the optical path of laser light from the second light source unit 120b and a radiation angle of laser light increases due to the diffusion member 111. A white LED generally used in the first light source unit 101 has a greater beam diameter and radiation angle than the laser light source (for example, semiconductor laser) used in the second light source unit 120b. Thus, by causing a radiation angle of laser light from the second light source unit 120b to increase using the diffusion member 111, white light from the first light source unit 101 and laser light from the second light source unit 120b can be ensured to have substantially the same beam diameter and incidence angle on the incidence end face of the light guide 130, i.e., the beam diameter and the radiation angle on the output end of the light guide 130 can be substantially the same. Thus, luminance distribution of radiation light on the observation site 1500 can be substantially the same and color unevenness or the like of the radiation light can be reduced.

In addition, in the illumination device 3100, the condenser optical system 117 is configured to cause light from the secondary light source to form an image such that the light fills the area of the incidence end of the light guide 130. Accordingly, speckle noise can be reduced for the entire illumination device 3100. Thus, an observation image of higher quality with reduced speckle noise can be obtained.

Furthermore, the endoscope device 3 can obtain the following effect.

In the illumination device 3100, white light from the first light source unit 101 and laser light from the second light source unit 120b are multiplexed on the same optical axis. Thus, shadows produced due to undulation of the observation site 1500 are observed in the same shape when white light from the first light source unit 101 is used as radiation light and when laser light from the second light source unit 120*b* is used as radiation light. Thus, in a portion in which no shadow is produced during normal observation, a shadow is produced during fluorescence observation, and thus a situation in which it is not possible to radiate excitation light to that portion does not occur. Therefore, a user can smoothly perform a series of operations of radiating excitation light in the special observation mode to a spot targeted in the normal observation mode, and user convenience can be improved.

In addition, in the illumination device 3100, the first light source unit 101 is configured with, for example, a white LED and the second light source unit 120*b* is configured with, for example, a semiconductor laser. When the first light source unit 101 and the second light source unit 120*b* are configured with semiconductor light emission elements as above, the output of emitted light from each of the light source units can be independently controlled at an arbitrary timing by appropriately controlling their driving currents. Thus, the output light from the illumination device 1100 can be adjusted at a higher degree of freedom.

Note that, although the case in which the second light source unit 120*b* only emits laser light of the wavelength band corresponding to the excitation light wavelength of the photosensitive pharmaceutical agent has been described in the above-described application example for the sake of simplicity, the second light source unit 120*b* of the illumination device 3100 may also emit laser light of a plurality of different wavelength bands as that of the illumination devices 50, 60, 70, and 80. When the second light source unit 120*b* is configured in this manner, the color temperature of multiplexed white light used as radiation light in the normal observation mode and the normal/special observation mode can be easily adjusted by controlling the outputs of the laser light independently of each other.

In addition, the illumination device 3100 is provided with the light detectors 1105 and 1109 for respectively detecting intensities of white light from the first light source unit 101 and laser light from the second light source unit 120*b* before multiplexing. Then, according to the intensities of the white light and the laser light monitored by the light detectors 1105 and 1109, driving of the first light source unit 101 and the second light source unit 120*b* is controlled. Thus, the intensities of the emitted light from the first light source unit 101 and the second light source unit 120*b* can be controlled with high accuracy, and quality of the output light from the illumination device 3100 can be further improved.

In addition, in the endoscope device 3, the imaging unit 1220 is configured such that light of the wavelength band corresponding to excitation light is not incident but light of the wavelength band corresponding to fluorescence is incident on the first image sensor 1223 by the optical filter 1221 in the special observation mode and the normal/special observation mode. In this manner, according to the present application example, with the relatively simple configuration of the optical filter 1221, a weak fluorescence component emitted from the observation site 1500 can be detected with high accuracy and thus a high-definition fluorescence observation image can be obtained.

In addition, as processes by the observation image generation unit 1305 are appropriately switched according to observation modes in the endoscope device 3, identification of an operative field based on a normal observation image in the normal observation mode, diagnosis of a tumor based on a fluorescence observation image in the special observation mode, and confirmation of the position of the tumor in the operative field based on an image in which the normal observation image and the fluorescence observation image overlap in the normal/special observation mode can be appropriately performed according to a desire of the user. In the normal/special observation mode, particularly, the image in which the normal observation image and the fluorescence observation image overlap can be obtained while white light and excitation light are radiated simultaneously, rather than in a time sharing manner. Thus, the tumor in the operative field can be observed in real time. Furthermore, in the present application example, such acquisition of an image in the normal/special observation mode can be executed with a relatively simple configuration of the optical filter 1221, the plurality of image sensors (the first image sensor 1223 and the second image sensor 1225), and the respective functions of the image processing device 1300 (the long-wavelength band image generation unit 1301, the short-wavelength band image generation unit 1303, and the observation image generation unit 1305). Therefore, without a size or cost of a device increasing, an observation image of higher quality can be obtained in the normal/special observation mode.

8-2-3. Another Configuration Example of the Endoscope Device

As a modified example of the endoscope device 3 described above, another configuration example of the endoscope device 3 will be described with reference to FIG. 24. FIG. 24 is a diagram illustrating the other configuration example of the endoscope device 3 illustrated in FIG. 22. Note that the endoscope device according to the present modified example corresponds to the endoscope device 3 illustrated in FIG. 22 in which the configuration of the endoscope unit 1200 is altered. Thus, in FIG. 24, of the configuration of the endoscope device according to the present modified example, only an endoscope unit 1200*c* is illustrated.

Referring to FIG. 24, the endoscope unit 1200*c* of the endoscope device according to the present modified example includes the lens barrel 1210 and an imaging unit 1220*c*. The configuration and the function of this lens barrel 1210 are the same as those of the lens barrel 1210 illustrated in FIG. 22. On the other hand, the imaging unit 1220*c* includes the optical filter 1221, the first image sensor 1223, the second image sensor 1225, and a second optical filter 1227. As described above, the imaging unit 1220*c* corresponds to the imaging unit 1220 of the endoscope device 3 illustrated in FIG. 22 in which the second optical filter 1227 is further provided.

As illustrated, the second optical filter 1227 is provided in the earlier stage of the second image sensor 1225. The second optical filter 1227 is a notch filter which only blocks light corresponding to the wavelength bands of laser light from the second light source unit 120*b* (for example, light of the wavelength band corresponding to the excitation light wavelength (664 nm) of Laserphyrin). By providing the second optical filter 1227, a reception amount of light of the wavelength band corresponding to the excitation light wavelength of Laserphyrin to the second image sensor 1225 can be controlled.

In the present modified example, processes of the observation image generation unit 1305 in the normal observation mode and the special observation mode are the same as those of the endoscope device 3 described above. A process of the observation image generation unit 1305 in the normal/special observation mode, however, is slightly different from the process of the endoscope device 3 described above.

Specifically, in the normal/special observation mode, the first light source unit 101 and the second light source unit 120b are driven together and light generated by multiplexing white light from the first light source unit 101 and laser light from the second light source unit 120b is radiated to the observation site 1500. At this time, the output of the laser light from the second light source unit 120b is adjusted to a value according to PDD and PDT.

In the imaging unit 1220c, light of a wavelength of 670 nm or longer is incident on the first image sensor 1223 and light of a wavelength shorter than 670 nm is incident on the second image sensor 1225. A component of the wavelength band corresponding to the excitation light wavelength of Laserphyrin is cut from the light to be incident on the second image sensor 1225.

The long-wavelength band image generation unit 1301 of the image processing device 1300 generates an image showing a tumor based on light of the red band with a wavelength of 670 nm or longer as the first image. In addition, the short-wavelength band image generation unit 1303 generates an image based on light of a red band, green band, and blue band with a wavelength shorter than 670 nm as the second image. A component of the wavelength band corresponding to the excitation light wavelength of Laserphyrin, however, is cut from the second image generated by the short-wavelength band image generation unit 1303.

In the present modified example, the observation image generation unit 1305 generates a combined image by summing up RGB values of the image generated by the long-wavelength band image generation unit 1301 and RGB values of the image generated by the short-wavelength band image generation unit 1303. Since the component of the wavelength band corresponding to the excitation light wavelength of Laserphyrin is cut from the second image generated by the short-wavelength band image generation unit 1303, merely by summing up the RGB values of both images, an image in which a normal observation image and a fluorescence observation image overlap can be obtained.

Specifically, when PDT is performed, the intensity of laser light from the second light source unit 120b is much higher than the intensity of white light from the first light source unit 101. Thus, when an image is generated based on light corresponding to the wavelength bands of laser light from the second light source unit 120b, the reception amount of light of the wavelength band is saturated, and there is a possibility of a normal image not being generated. Therefore, in the endoscope device 1 described above, a combined image is generated by summing up the R value of the first image and the GB values of the second image and cutting the component corresponding to the wavelength bands of laser light from the second light source unit 120b in the stage of a so-called image process in the normal/special observation mode. On the other hand, in the present modified example, an image in which the component of the wavelength bands of laser light is cut can be obtained by providing the second optical filter 1227 in the earlier stage of the second image sensor 1225 to block incidence of light corresponding to the wavelength band of the laser light from the second light source unit 120b on the second image sensor 1225, and simply summing up the RGB values of the first image and the RGB values of the second image.

8-3. Microscope Device 8-3-1. Configuration of a Microscope Device

A configuration of a microscope device to which the illumination devices 50, 60, 70, and 80 are applied will be described with reference to FIGS. 25 and 26. FIG. 25 is a diagram illustrating a configuration example of the microscope device to which the illumination devices 50, 60, 70, and 80 according to the third and fourth embodiments and the respective modified examples are applied. FIG. 26 is an illustrative diagram for describing a radiation range of radiation light with respect to the observation site 1500.

Note that a case in which the configuration of the illumination device 50 according to the third embodiment is mounted in the microscope device will be described below as an example. As will be described below, when the illumination devices 50, 60, 70, and 80 are applied to the microscope device, a radiation intensity of excitation light to the observation site 1500 is controlled with high accuracy while PDT is performed, and it is preferable to use an illumination device in which the optical fiber 107 is mounted as in the illumination device 50. The present application example, however, is not limited thereto, and a configuration of another illumination device 60, 70, or 80 may be mounted in the microscope device.

Referring to FIG. 25, the microscope device 4 includes an illumination device 4100, an imaging unit 2200, the image processing device 1300, and the display device 1400. Note that, in FIG. 25, the observation site 1500 to which output light from the illumination device 4100 is radiated is also schematically illustrated.

Illumination Device 4100

The illumination device 4100 generates white light (multiplexed white light) for normal observation and excitation light for fluorescence observation. White light and/or excitation light generated by the illumination device 4100 are projected to the outside via the projection lens 1111, and then radiated to the observation site 1500.

Here, the illumination device 4100 corresponds to the illumination device 50 according to the third embodiment described above. Several members, however, are omitted from or added to the illumination device when it is mounted in the microscope device 4.

Specifically, the illumination device 4100 includes the first light source unit 101 which radiates white light, the first collimator optical system 103, a second light source unit 120b which includes at least one laser light source that emits light of a predetermined wavelength band, the coupling optical system 105, the optical fiber 107, the third collimator optical system 109, a multiplexing member 115c, the condenser optical system 117, a laser line filter 1101, a half mirror 1103, a light detector 1105, another half mirror 1107, another light detector 1109, and a control unit 1120.

As described above, the illumination device 4100 corresponds to the illumination device 50 according to the third embodiment to which the laser line filter 1101, the half mirror 1103, the light detector 1105, the half mirror 1107, and the light detector 1109 are added and from which the second collimator optical system 113 and the diffusion member 111 are omitted. In addition, for the illumination device 4100, the optical characteristics of the second light source unit 120 and the dichroic mirror 115 of the illumination device 50 according to the third embodiment are also altered. Since configurations and functions of other members are the same as those of the respective members shown in FIG. 16, detailed description regarding those members will be omitted. In addition, the control unit 1120 corresponds to the control unit which controls driving of the first light source unit 101 and the second light source unit 120b, not illustrated in FIG. 16.

Here, since the configurations and functions of the second light source unit 120b, the laser line filter 1101, the half mirror 1103, the light detector 1105, the half mirror 1107, the light detector 1109, and the control unit 1120 are the same as those of the members of the endoscope device 3 illustrated in FIG. 22, detailed description thereof will be omitted.

As illustrated, in the illumination device 4100, laser light emitted from the second light source unit 120*b* passes through the coupling optical system 105, the optical fiber 107, the third collimator optical system 109, the laser line filter 1101, and the half mirror 1103 in this order, and is incident on the multiplexing member 115*c* as substantially parallel light. On the other hand, white light emitted from the first light source unit 101 passes through the first collimator optical system 103 and is incident on the multiplexing member 115*c* as substantially parallel light.

The projection lens 1111 is provided in a partial region of a separating wall of the case of the illumination device 4100, and light that has passed through the multiplexing member 115*c* is radiated to the observation site 1500 via the projection lens 1111.

As with the endoscope device 3, a configuration and an operation of the microscope device 4 when Laserphyrin is used as a photosensitive pharmaceutical agent will be described below as an example. In addition, the second light source unit 120 multiplexes and emits laser light of three different wavelength bands in the configuration example described in (1. Third embodiment) described above; however, in order to simplify description, the second light source unit 120*b* will be described as only emitting laser light of a wavelength band corresponding to the excitation light wavelength of Laserphyrin. This corresponds to a state in which, among a plurality of laser light sources included in the second light source unit 120*b*, only a laser light source that can emit laser light corresponding to the excitation light wavelength of Laserphyrin is driven.

Note that the characteristic of the light multiplexed by the multiplexing member 115*c* when Laserphyrin is used is the same as that described with reference to FIG. 23. That is, the light generated by the multiplexing member 115*c* multiplexing the white light emitted from the first light source unit 101 and the laser light emitted from the second light source unit 120*b* is white light (i.e., multiplexed white light) generated by superimposing the component of the wavelength band corresponding to the excitation light wavelength of Laserphyrin on the white light.

An example of radiation ranges on the observation site 1500 when the multiplexed white light is radiated to the observation site 1500 is illustrated in FIG. 26. When the white light emitted from the first light source unit 101 and the laser light emitted from the second light source unit 120*b* are radiated to the observation site 1500 together, it is preferable particularly in the normal/special observation mode to adjust a first radiation range 1501 of the white light from the first light source unit 101 and a second radiation range 1503 of the laser light from the second light source unit 120*b* such that the second radiation range 1503 is included in the first radiation range 1501 as illustrated in FIG. 26. When the radiation ranges 1501 and 1053 are in the relation as illustrated and PDD or PDT is performed, for example, normal observation of the observation site 1500 is performed using white light from the first light source unit 101, and a site targeted in the normal observation can be irradiated with laser light (i.e., excitation light) from the second light source unit 120*b*.

The adjustment of the first radiation range 1501 and the second radiation range 1503 can be controlled by adjusting the core diameter of the optical fiber 107, the focal length of the third collimator optical system 109, and the focal length of the projection lens 1111. At this time, it is desirable to adjust the optical characteristics of the members so that an image on the emission end face of the optical fiber 107 is formed on the observation site 1500. The reason for this is that, as the intensity and size of laser light on the emission end face of the optical fiber 107 are adjusted, the intensity and size of the laser light radiated to the observation site 1500 can be adjusted.

Here, when PDT is performed, for example, the intensity of excitation light to be radiated to a lesion part (tumor) per unit time and unit area is generally decided according to the type of tumor, the type of photosensitive pharmaceutical agent, or the like. Thus, by appropriately adjusting the intensity and the size of laser light to be radiated to the observation site 1500 using the optical fiber 107 in the microscope device 4 as described above, PDT can be performed more effectively.

Since the optical fiber 107 is provided and the intensity and the size of laser light on the emission end of the optical fiber that can be conjugated with the observation site 1500 are appropriately adjusted in the microscope device 4, the intensity and the size of laser light to be radiated to the observation site 1500 can be adjusted. Thus, in order to control radiation of excitation light to the observation site 1500 with high accuracy when PDT is performed, it is preferable for the microscope device 4 to be provided with the optical fiber 107 as illustrated.

Imaging Unit 2200

The imaging unit 2200 includes the optical filter 1221, the first image sensor 1223, the second image sensor 1225, and an image lens 2227. The image lens 2227 is provided in a partial region of a separating wall of the case of the imaging unit 2200, and guides reflected light from the observation site 1500 into the case. The light guided into the case of the imaging unit 2200 via the image lens 2227 is incident on the optical filter 1221 provided in the case. Note that, in FIG. 25, propagation of light in the imaging unit 2200 is schematically illustrated with dashed-line arrows.

Since the configurations and the functions of the optical filter 1221, the first image sensor 1223, and the second image sensor 1225 are the same as those of the members of the endoscope device 3 illustrated in FIG. 22, detailed description thereof is omitted. In other words, reflected light from the observation site 1500 is separated into, for example, light of a wavelength of 670 nm or longer and light of a wavelength shorter than 670 nm by the optical filter 1221, and the light of a wavelength of 670 nm or longer is incident on the first image sensor 1223 and the light of a wavelength shorter than 670 nm is incident on the second image sensor 1225.

Image Processing Device 1300

The image processing device 1300 generates a captured image (observation image) of the observation site 1500 based on reflected light from the observation site 1500 detected by the imaging unit 2200. Note that, since a configuration and a function of the image processing device 1300 are the same as those of the image processing device 1300 of the endoscope device 3 illustrated in FIG. 22, detailed description thereof is omitted.

Display Device 1400

The display device 1400 displays an image generated by the observation image generation unit 1305 of the image processing device 1300. Note that a configuration and a function of the display device 1400 are the same as those of the display device 1400 of the endoscope device 3 illustrated in FIG. 22, and thus detailed description thereof is omitted.

8-3-2. Operation of the Microscope Device

Operations of the microscope device 4 described above according to the observation modes will be described. In the microscope device 4, any of the normal observation mode, the special observation mode, and the normal/special observation mode can be selected as an observation mode. Note that, since the operations of the microscope device 4 according to respective observation modes are the same as those of the endoscope device 3 illustrated in FIG. 22 according to the respective observation modes, detailed description regarding overlapping points is omitted.

Normal Observation Mode

In the normal observation mode, light of a broad band corresponding to visible light in the range of approximately 400 nm to 750 nm is radiated to the observation site 1500 and an image of the observation site 1500 is acquired.

When the normal observation mode is selected as an observation mode by a user, the first light source unit 101 and the second light source unit 120b of the illumination device 4100 are driven together. At this time, output light from the illumination device 4100 is light generated by multiplexing white light from the first light source unit 101 and laser light from the second light source unit 120 (multiplexed white light) as shown in FIG. 23. Here, in the normal observation mode, the output of the white light emitted from the first light source unit 101 and the laser light emitted from the second light source unit 120b can be appropriately adjusted in a possible range so that the multiplexed white light has a predetermined hue set in advance by a user.

In the imaging unit 2200, light of a wavelength of 670 nm or longer is incident on the first image sensor 1223 and light of a wavelength shorter than 670 nm is incident on the second image sensor 1225 as described above. Thus, the long-wavelength band image generation unit 1301 of the image processing device 1300 generates an image as the first image based on light of a red band with a wavelength of 670 nm or longer. In addition, the short-wavelength band image generation unit 1303 generates an image as the second image based on light of a red band, a green band, and a blue band with a wavelength shorter than 670 nm.

In the normal observation mode, the observation image generation unit 1305 generates a combined image by summing up the RGB values of the image generated by the long-wavelength band image generation unit 1301 and the RGB values of the image generated by the short-wavelength band image generation unit 1303. The combined image generated in this way is a normal observation image corresponding to radiation light of a visible light band (about 400 nm to 750 nm).

Special Observation Mode

In the special observation mode, narrow-band light corresponding to the excitation light wavelength of Laserphyrin that is a photosensitive pharmaceutical agent is radiated to the observation site 1500 and an image based on fluorescence from the observation site 1500 is acquired. The special observation mode is an observation mode used when PDD and PDT are performed.

When the special observation mode is selected as an observation mode by a user, only the second light source unit 120 of the illumination device 3100 is driven. At this time, output light from the illumination device 3100 is light without the spectrum of white light in the spectrum shown in FIG. 23, i.e., laser light having the excitation light wavelength of Laserphyrin as the center wavelength. Note that, when PDT is performed in the special observation mode, the output of laser light from the second light source unit 120 is set to be stronger than when PDD is performed.

In the imaging unit 2200, light having a wavelength of 670 nm or longer is incident on the first image sensor 1223 and light having a wavelength shorter than 670 nm is incident on the second image sensor 1225 as described above. Thus, the long-wavelength band image generation unit 1301 of the image processing device 1300 generates an image based on light in a red band with a wavelength of 670 nm or longer as the first image.

Here, since the fluorescence wavelength of Laserphyrin is 672 nm, the first image generated by the long-wavelength band image generation unit 1301 is an image based on fluorescence of Laserphyrin, i.e., an image in which a tumor that is an observation target in the special observation mode is selectively visible. Thus, in the special observation mode, the observation image generation unit 1305 outputs the image generated by the long-wavelength band image generation unit 1301, i.e., the fluorescence observation image to the display device 1400.

Normal/Special Observation Mode

In the normal/special observation mode, by simultaneously performing radiation of white light for normal observation and radiation of excitation light for special observation, recognition of the shape of an operative field based on a normal observation image and fluorescence observation of a tumor based on a special observation image can be simultaneously performed.

When the normal/special observation mode is selected as an observation mode by a user, the first light source unit 101 and the second light source unit 120b of the illumination device 3100 are driven together as in the normal observation mode. At this time, the output light from the illumination device 3100 is light generated by multiplexing the white light from the first light source unit 101 and laser light from the second light source unit 120b (multiplexed white light) as shown in FIG. 24. Unlike in the normal observation mode, however, the output of the laser light from the second light source unit 120b is adjusted to a value according to PDD and PDT in the normal/special observation mode. Note that, in this case, when PDT is performed, the output of laser light from the second light source unit 120b is set to be stronger than when PDD is performed, like in the special observation mode.

In the imaging unit 2200, light of a wavelength of 670 nm or longer is incident on the first image sensor 1223 and light of a wavelength shorter than 670 nm is incident on the second image sensor 1225 as described above. Thus, the long-wavelength band image generation unit 1301 of the image processing device 1300 generates an image as the first image based on light of a red band with a wavelength of 670 nm or longer. In addition, the short-wavelength band image generation unit 1303 generates an image as the second image based on light of a red band, a green band, and a blue band with a wavelength shorter than 670 nm.

Here, since the fluorescence wavelength of Laserphyrin is 672 nm, the first image generated by the long-wavelength band image generation unit 1301 is an image based on fluorescence of Laserphyrin, i.e., an image in which a tumor is selectively visible. On the other hand, a red component of the second image generated by the short-wavelength band image generation unit 1303 is considered to be based on a component corresponding to the excitation light wavelength of Laserphyrin of radiation light. The red component of the second image can be said to be a component that hinders fluorescence observation of a tumor.

Thus, the observation image generation unit 1305 generates a combined image in the normal/special observation mode by summing up an R value of the first image generated by the long-wavelength band image generation unit 1301 and GB values of the second image generated by the short-wavelength band image generation unit 1303. The combined image generated in this manner is an image in which a normal observation image based on the GB values of the second image and a fluorescence observation image based on the R value of the first image overlap. In the image, a tumor is displayed in red in the normal observation image based on the GB values.

The configuration and operations of the microscope device 4 into which the illumination device 4100 having substantially the same configuration as the illumination device 50 according to the third embodiment is incorporated have been described above. According to the microscope device 4, the following effects can be exhibited, like the endoscope device 3 described above.

In the illumination device 4100, white light from the first light source unit 101 and laser light from the second light source unit 120b are multiplexed on the same optical axis. Thus, shadows produced due to undulation of the observation site 1500 are observed in the same shape when white light from the first light source unit 101 is used as radiation light and when laser light from the second light source unit 120b is used as radiation light. Thus, in a portion in which no shadow is produced during normal observation, a shadow is produced during fluorescence observation, and thus a situation in which it is not possible to radiate excitation light to that portion does not occur. Therefore, a user can smoothly perform a series of operations of radiating excitation light in the special observation mode to a spot targeted in the normal observation mode, and user convenience can be improved.

In addition, in the illumination device 4100, the first light source unit 101 is configured with, for example, a white LED and the second light source unit 120b is configured with, for example, a semiconductor laser. When the first light source unit 101 and the second light source unit 120b are configured with semiconductor light emission elements as above, the output of emitted light from each of the light source units can be independently controlled at an arbitrary timing by appropriately controlling their driving currents. Thus, the output light from the illumination device 1100 can be adjusted at a higher degree of freedom.

Note that, although the case in which only laser light of the wavelength band corresponding to the excitation light wavelength of the photosensitive pharmaceutical agent is emitted from the second light source unit 120b has been described in the application examples described above for the sake of simplification, a plurality of laser light beams of different wavelength bands (for example, red laser light, green laser light, and blue laser light corresponding to the three primary colors of light) may be emitted from the second light source unit 120b in the illumination device 4100 as in the illumination devices 50, 60, 70, and 80. When the second light source unit 120b is configured in this way, a color temperature of multiplexed white light used as radiation light in the normal observation mode and the normal/special observation mode can be adjusted more easily by controlling the outputs of the laser light beams of the respective colors independently of each other.

In addition, the illumination device 4100 is provided with the light detectors 1105 and 1109 for respectively detecting intensities of white light from the first light source unit 101 and laser light from the second light source unit 120b before multiplexing. Then, according to the intensities of the white light and the laser light monitored by the light detectors 1105 and 1109, driving of the first light source unit 101 and the second light source unit 120b is controlled. Thus, the intensities of the emitted light from the first light source unit 101 and the second light source unit 120b can be controlled with high accuracy, and quality of the output light from the illumination device 4100 can be further improved.

In addition, in the microscope device 4, the imaging unit 2200 is configured such that light of the wavelength band corresponding to excitation light is not incident but light of the wavelength band corresponding to fluorescence is incident on the first image sensor 1223 by the optical filter 1221 in the special observation mode and the normal/special observation mode. In this manner, according to the present application example, with the relatively simple configuration of the optical filter 1221, a weak fluorescence component emitted from the observation site 1500 can be detected with high accuracy and thus a high-definition fluorescence observation image can be obtained.

In addition, as processes by the observation image generation unit 1305 are appropriately switched according to observation modes in the microscope device 4, identification of an operative field based on a normal observation image in the normal observation mode, diagnosis of a tumor based on a fluorescence observation image in the special observation mode, and confirmation of the position of the tumor in the operative field based on an image in which the normal observation image and the fluorescence observation image overlap in the normal/special observation mode can be appropriately performed according to a desire of the user. In the normal/special observation mode, particularly, the image in which the normal observation image and the fluorescence observation image overlap can be obtained while white light and excitation light are radiated simultaneously, rather than in a time sharing manner. Thus, the tumor in the operative field can be observed in real time. Furthermore, in the present application example, such acquisition of an image in the normal/special observation mode can be executed with a relatively simple configuration of the optical filter 1221, the plurality of image sensors (the first image sensor 1223 and the second image sensor 1225), and the respective functions of the image processing device 1300 (the long-wavelength band image generation unit 1301, the short-wavelength band image generation unit 1303, and the observation image generation unit 1305). Therefore, without a size or cost of a device increasing, an observation image of higher quality can be obtained in the normal/special observation mode.

9. SUPPLEMENT

The preferred embodiments of the present disclosure have been described above with reference to the accompanying drawings, whilst the present disclosure is not limited to the above examples, of course. A person skilled in the art may find various alterations and modifications within the scope of the appended claims, and it should be understood that they will naturally come under the technical scope of the present disclosure.

In addition, the effects described in the present description are merely illustrative and demonstrative, and not limitative. In other words, the technology according to an embodiment of the present disclosure can exhibit other effects that are evident to those skilled in the art along with or instead of the effects based on the present specification.

Additionally, the present technology may also be configured as below.

(1) A medical imaging system including:
an illumination device including:
a first light source configured to emit first light having a wavelength range;
a second light source configured to emit second light having at least one predetermined wavelength band, wherein the at least one predetermined wavelength band is within the wavelength range; and
a dichroic mirror configured to attenuate a portion of the wavelength range corresponding to the at least one predetermined wavelength band and to multiplex the second light with the first light such that the portion of the wavelength range of the first light is attenuated, wherein light multiplexed by the dichroic mirror is emitted from the illumination device along an optical axis and irradiates an observation site; and
a medical imaging device including at least one image sensor configured to receive light from the observation site.

(2) The medical imaging system of claim (1), wherein light emitted by the illumination device includes light having a higher intensity within the at least one predetermined wavelength band than in portions of the wavelength range outside the at least one predetermined wavelength band.

(3) The medical imaging system of claim (1), wherein the illumination device further includes a diffusion member positioned between the second light source and the dichroic mirror.

(4) The medical imaging system of claim (1), further including a light guide, wherein light emitted from the illumination device is incident on an end of the light guide.

(5) The medical imaging system of claim (4), further including a condenser optical system positioned along the optical axis and configured to condense light from the dichroic mirror on the end of the light guide.

(6) The medical imaging system of claim (5), wherein a size of an image of the condensed light is substantially the same as the diameter of the end of the light guide.

(7) The medical imaging system of claim (4), further including a lens barrel configured to receive the light guide and radiate light from the illumination device to the observation site.

(8) The medical imaging system of claim (7), wherein the lens barrel is further configured to direct light from the observation site to the image sensor.

(9) The medical imaging system of claim (4), further including a projection lens configured to radiate light from the illumination device to the observation site.

(10) The medical imaging system of claim (1), further including circuitry configured to adjust the intensity of light emitted by the first light source and the intensity of light emitted by the second light source.

(11) The medical imaging system of claim (10), wherein the at least one predetermined wavelength band includes a plurality of predetermined wavelength bands, and the circuitry is further configured to adjust the intensity of light for each predetermined wavelength band of the plurality of predetermined wavelength bands.

(12) The medical imaging system of claim (1), further including a condenser optical system positioned along the optical axis and configured to modulate a size of an area illuminated by light emitted from the illumination device.

(13) The medical imaging system of claim (1), wherein the first light incident on the dichroic mirror is substantially parallel and the second light incident on the dichroic mirror is substantially parallel.

(14) The medical imaging system of claim (1), wherein the first light incident on the dichroic mirror is divergent and the second light incident on the dichroic mirror is divergent.

(15) The medical imaging system of claim (1), wherein the medical imaging device is configured to obtain an image of the observation site that includes fluorescence information of the observation site and white light imaging information.

(16) An illumination device including:
a first light source configured to emit light having a wavelength range;
a second light source configured to emit light having at least one predetermined wavelength band, wherein the at least one predetermined wavelength band is within the wavelength range; and
a dichroic mirror configured to attenuate a portion of the wavelength range corresponding to the at least one predetermined wavelength band and to multiplex the second light with the first light such that the portion of the wavelength range of the first light is attenuated, wherein light multiplexed by the dichroic mirror is emitted from the illumination device along an optical axis and irradiates an observation site.

(17) The illumination device of claim (16), wherein light emitted by the illumination device includes light having a higher intensity within the at least one predetermined wavelength band than in portions of the wavelength range outside the at least one predetermined wavelength band.

(18) The illumination device of claim (16), further including a diffusion member positioned between the second light source and the dichroic mirror.

(19) A method for illuminating an observation site including:
irradiating the observation site with light emitted by an illumination device, wherein the light has a wavelength range; and
adjusting an intensity of at least one predetermined wavelength band within the wavelength range such that the at least one predetermined wavelength band has a higher intensity than portions of the wavelength range outside the at least one predetermined wavelength band.

(20) The method of claim (19), wherein irradiating the observation site with light comprises irradiating light having the at least one predetermined wavelength band corresponding to an excitation wavelength of an object in the observation site.

(21) The method of claim (19), further comprising detecting, by an image sensor, a value corresponding to the intensity of the at least one predetermined wavelength band and controlling adjustment of the intensity of the at least one predetermined wavelength band based on the value.

(22)

An illumination device including:

a first light source unit configured to emit white light;

a second light source unit configured to emit laser light of a plurality of predetermined wavelength bands included in a wavelength band of the white light;

a diffusion member configured to generate a secondary light source by diffusing the laser light emitted from the second light source unit; and a dichroic mirror configured to multiplex the white light emitted from the first light source unit and the laser light emitted from the secondary light source, wherein the dichroic mirror attenuates a component of the white light of a wavelength band corresponding to the laser light and multiplexes the laser light with the white light of which the component of the wavelength band corresponding to the laser light has been attenuated.

(23)

The illumination device according to (22), further including:

a first collimator optical system configured to convert the white light emitted from the first light source unit into substantially parallel light; and a second collimator optical system configured to convert the laser light emitted from the diffusion member into substantially parallel light, wherein the dichroic mirror multiplexes the white light which has been converted into substantially parallel light by the first collimator optical system and the laser light which has been converted into substantially parallel light by the second collimator optical system.

(24)

The illumination device according to (22) or (23), further including:

a coupling optical system configured to couple the laser light emitted from the second light source unit to an optical fiber; and a third collimator optical system configured to convert laser light emitted from the optical fiber into substantially parallel light, wherein the diffusion member generates the secondary light source by diffusing laser light emitted from the third collimator optical system.

(25)

The illumination device according to any one of (22) to (24), further including:

a condenser optical system configured to cause light multiplexed by the dichroic mirror to form an image on an incidence end of a light guide, wherein the condenser optical system causes light from the secondary light source to form an image on the incidence end of the light guide so that a size of an image of the secondary light source formed on the incidence end of the light guide becomes substantially equal to a diameter of the incidence end of the light guide.

(26)

The illumination device according to any one of (22) to (25), wherein the second light source unit includes a plurality of laser light sources, and wherein the plurality of laser light sources include at least a red laser light source which emits red laser light, a green laser light source which emits green laser light, and a blue laser light source which emits blue laser light.

(27)

The illumination device according to any one of (22) to (26), wherein the second light source unit includes the plurality of laser light sources, and wherein a color temperature of light multiplexed by the dichroic mirror is adjusted by controlling driving of the plurality of laser light sources independently of each other.

(28)

The illumination device according to any one of (22) to (27), wherein at least one of laser light sources included in the second light source unit emits laser light of a wavelength band corresponding to excitation light used in fluorescence observation of an observation site.

(29)

The illumination device according to any one of (22) to (28), further including:

a third light source unit configured to emit light of a wavelength band different from the laser light emitted from the second light source unit, wherein light generated by multiplexing the white light emitted from the first light source unit and the light emitted from the third light source unit is incident on the dichroic mirror, and wherein the dichroic mirror further multiplexes the light generated by multiplexing the white light emitted from the first light source unit and the light emitted from the third light source unit with the laser light emitted from the second light source unit.

(30)

The illumination device according to (29), wherein the first light source unit and the third light source unit each include an LED.

(31)

An illuminating method including:

emitting white light from a first light source unit;

emitting, from a second light source unit, laser light of a plurality of predetermined wavelength bands included in a wavelength band of the white light;

generating a secondary light source by diffusing the laser light emitted from the second light source unit with a diffusion member; and multiplexing the white light emitted from the first light source unit and the laser light emitted from the secondary light source with a dichroic mirror, wherein the dichroic mirror attenuates a component of the white light of a wavelength band corresponding to the laser light and multiplexes the laser light with the white light of which the component of the wavelength band corresponding to the laser light has been attenuated.

(32)

An observation device including:

an illumination device configured to output at least one of white light and excitation light to be radiated to an operative field of a patient, wherein the illumination device includes a first light source unit configured to emit white light, a second light source unit configured to emit laser light of a plurality of predetermined wavelength bands including a wavelength band corresponding to the excitation light, the plurality of predetermined wavelength bands being included in a wavelength band of the white light, a diffusion member configured to generate a secondary light source by diffusing the laser light emitted from the second light source unit, and a dichroic mirror configured to multiplex the white light emitted from the first light source unit and the laser light emitted from the secondary light source, wherein the dichroic mirror attenuates a component of the white light of a wavelength band corresponding to the laser light and multiplexes the laser light with the white light of which the component of the wavelength band corresponding to the laser light has been attenuated.

(33)

The observation device according to (32), wherein the observation device is an endoscope device further including a lens barrel which is inserted into a body cavity of a patient and into which output light from the illumination device is guided to be radiated to an operative field inside the body cavity.

(34)

The observation device according to (32) or (33), further including:

a long-wavelength band image generation unit configured to generate a first image based on light which has a longer wavelength band than the excitation light and includes a wavelength band of fluorescence by the excitation light; and a short-wavelength band image generation unit configured to generate a second image based on light which has a shorter wavelength band than the wavelength band the fluorescence and includes the wavelength band of the excitation light.

(35)

The observation device according to (34), wherein, in a normal observation mode in which a normal observation image of an operative field is obtained using white light, the first light source unit and the second light source unit are driven together, and the normal observation image is obtained by combining the first image and the second image.

(36)

The observation device according to (35), wherein, in the normal observation mode, the normal observation image is generated by summing up RGB values of the first image and RGB values of the second image.

(37)

The observation device according to any one of (34) to (36), wherein, in a special observation mode in which a fluorescence observation image of an operative field is obtained using excitation light, only the second light source unit between the first light source unit and the second light source unit is driven, and the second image is obtained as the fluorescence observation image.

(38)

The observation device according to any one of (34) to (37), wherein, in a normal/special observation mode in which a normal observation image of an operative field using white light and a fluorescence observation image of the operative field using excitation light are simultaneously obtained, the first light source unit and the second light source unit are driven together, and an image in which the normal observation image overlaps with the fluorescence observation image is obtained by combining the first image and the second image.

(39)

The observation device according to (38), wherein, in the normal/special observation mode, the image in which the normal observation image overlaps with the fluorescence observation image is generated by summing up an R value of the first image and GB values of the second image.

(40)

The observation device according to (38), wherein the short-wavelength band image generation unit generates the second image based on light of which a component of a wavelength band corresponding to the excitation light has been attenuated or removed, and wherein, in the normal/special observation mode, the image in which the normal observation image overlaps with the fluorescence observation image is generated by summing up RGB values of the first image and RGB values of the second image.

(41)

An illumination device including:

a first light source unit configured to emit white light;

a second light source unit configured to emit laser light of at least one predetermined wavelength band included in a wavelength band of the white light; and a multiplexing member configured to multiplex the white light and the laser light, wherein the multiplexing member includes a polarization conversion element which is at least disposed on an optical path of light that is random polarization light between the white light and the laser light and converts a polarization direction of incidence light into a predetermined direction and a polarizing beam splitter on which light that has passed through the polarization conversion element is incident, and wherein the polarizing beam splitter multiplexes the white light and the laser light of which polarization directions are in a mutually orthogonal state by the polarization conversion element.

(42)

The illumination device according to (41), further including:

a first collimator optical system configured to convert the white light emitted from the first light source unit into substantially parallel light;

a diffusion member configured to generate a secondary light source by diffusing the laser light emitted from the second light source unit; and a second collimator optical system configured to convert laser light emitted from the diffusion member into substantially parallel light, wherein the multiplexing member multiplexes the white light which has been converted into substantially parallel light by the first collimator optical system and the laser light which has been converted into substantially parallel light by the second collimator optical system.

(43)

The illumination device according to (42), further including:

a coupling optical system configured to couple the laser light emitted from the second light source unit to an optical fiber; and a third collimator optical system configured to convert laser light emitted from the optical fiber into substantially parallel light, wherein the diffusion member generates the secondary light source by diffusing laser light emitted from the third collimator optical system.

(44)

The illumination device according to (42) or (43), further including:

a condenser optical system configured to cause light multiplexed by the multiplexing member to form an image on an incidence end of a light guide, wherein the condenser optical system causes light from the secondary light source to form an image on the incidence end of the light guide so that a size of an image of the secondary light source formed on the incidence end of the light guide becomes substantially equal to a diameter of the incidence end of the light guide.

(45)

The illumination device according to any one of (41) to (44), wherein the second light source unit includes a plurality of laser light sources, and wherein the plurality of laser light sources include at least a red laser light source which emits red laser light, a green laser light source which emits green laser light, and a blue laser light source which emits blue laser light.

(46)

The illumination device according to any one of (41) to (45), wherein the second light source unit includes the plurality of laser light sources, and wherein a color temperature of light multiplexed by the multiplexing member is adjusted by controlling driving of the plurality of laser light sources independently of each other.

(47)

The illumination device according to any one of (41) to (46), wherein at least one of laser light sources included in the second light source unit emits laser light of a wavelength band corresponding to excitation light used in fluorescence observation of an observation site.

(48)

The illumination device according to any one of (41) to (47), further including:

a third light source unit configured to emit light of a wavelength band different from the laser light emitted from the second light source unit, wherein light generated by multiplexing the white light emitted from the first light source unit and the light emitted from the third light source unit is incident on the multiplexing member, and wherein the multiplexing member further multiplexes the light generated by multiplexing the white light emitted from the first light source unit and the light emitted from the third light source unit with the laser light emitted from the second light source unit.

(49)

The illumination device according to (48), wherein the first light source unit and the third light source unit each include an LED.

(50)

An illuminating method including:

emitting white light from a first light source unit;

emitting, from a second light source unit, laser light of at least one predetermined wavelength band included in a wavelength band of the white light; and multiplexing the white light and the laser light with a multiplexing member, wherein the multiplexing member includes a polarization conversion element which is at least disposed on an optical path of light that is random polarization light between the white light and the laser light and converts a polarization direction of incidence light into a predetermined direction and a polarizing beam splitter on which light that has passed through the polarization conversion element is incident, and wherein the polarizing beam splitter multiplexes the white light and the laser light of which polarization directions are in a mutually orthogonal state by the polarization conversion element.

(51)

An observation device including:

an illumination device configured to output at least one of white light and excitation light to be radiated to an operative field of a patient, wherein the illumination device includes a first light source unit configured to emit white light, a second light source unit configured to at least emit laser light of a wavelength band corresponding to the excitation light, the wavelength band being included in a wavelength band of the white light, and a multiplexing member configured to multiplex the white light and the laser light, wherein the multiplexing member includes a polarization conversion element which is at least disposed on an optical path of light that is random polarization light between the white light and the laser light and converts a polarization direction of incidence light into a predetermined direction and a polarizing beam splitter on which light that has passed through the polarization conversion element is incident, and wherein the polarizing beam splitter multiplexes the white light and the laser light of which polarization directions are in a mutually orthogonal state by the polarization conversion element.

(52)

The observation device according to (51), wherein the observation device is an endoscope device further including a lens barrel which is inserted into a body cavity of a patient and into which output light from the illumination device is guided to be radiated to an operative field inside the body cavity.

(53)

The observation device according to (51), wherein the observation device is a microscope device in which output light from the illumination device is emitted to an outside via a projection lens to be radiated to an operative field.

(54)

The observation device according to any one of (51) to (53), further including:

a long-wavelength band image generation unit configured to generate a first image based on light which has a longer wavelength band than the excitation light and includes a wavelength band of fluorescence by the excitation light; and a short-wavelength band image generation unit configured to generate a second image based on light which has a shorter wavelength band than the wavelength band the fluorescence and includes the wavelength band of the excitation light.

(55)

The observation device according to (54), wherein, in a normal observation mode in which a normal observation image of an operative field is obtained using white light, the first light source unit and the second light source unit are driven together, and the normal observation image is obtained by combining the first image and the second image.

(56)

The observation device according to (55), wherein, in the normal observation mode, the normal observation image is generated by summing up RGB values of the first image and RGB values of the second image.

(57)

The observation device according to any one of (54) to (56), wherein, in a special observation mode in which a fluorescence observation image of an operative field is obtained using excitation light, only the second light source unit between the first light source unit and the second light source unit is driven, and the second image is obtained as the fluorescence observation image.

(58)

The observation device according to any one of (54) to (57), wherein, in a normal/special observation mode in which a normal observation image of an operative field using white light and a fluorescence observation image of the operative field using excitation light are simultaneously obtained, the first light source unit and the second light source unit are driven together, and an image in which the normal observation image overlaps with the fluorescence observation image is obtained by combining the first image and the second image.

(59)

The observation device according to (58), wherein, in the normal/special observation mode, the image in which the normal observation image overlaps with the fluorescence observation image is generated by summing up an R value of the first image and GB values of the second image.

(60)

The observation device according to (58),
wherein the short-wavelength band image generation unit generates the second image based on light of which a component of a wavelength band corresponding to the excitation light has been attenuated or removed, and
wherein, in the normal/special observation mode, the image in which the normal observation image overlaps with the fluorescence observation image is generated by summing up RGB values of the first image and RGB values of the second image.

REFERENCE SIGNS LIST 1 endoscope device
2 microscope device
10, 20, 30, 40, 50, 60, 70, 80, 1100, 2100, 3100, 4100 illumination device
101 first light source unit
103, 103a first collimator optical system
105 coupling optical system
107 optical fiber
109 third collimator optical system
111 diffusion member
113, 113a second collimator optical system
115, 115b dichroic mirror
115c multiplexing member
117, 117a condenser optical system
119 third light source unit
120, 120b second light source unit
121R, 121G 121B laser light source
122R, 122G, 122B dichroic mirror
125 second dichroic mirror
130 light guide
141 polarizing beam splitter
142 first polarization conversion element
143 second polarization conversion element
1101 laser line filter
1103, 1107 half mirror
1105, 1109 light detector
1111 projection lens
1120 control unit
1121 first-light-source-unit driving control unit
1123 second-light-source-unit driving control unit
1200, 1200c endoscope unit
1210 lens barrel
1220, 1220c, 2200 imaging unit
1221 optical filter
1223 first image sensor
1225 second image sensor
1227 second optical filter
1300 image processing device
1301 long-wavelength band image generation unit
1303 short-wavelength band image generation unit
1305 observation image generation unit
1307 input unit
1400 display device
1500 observation site
1501 first radiation range
1503 second radiation range
2227 image lens

The invention claimed is:

1. A medical imaging system, comprising:
an illumination device comprising:
a first light source configured to emit first light having a first wavelength range;
a first collimator optical system configured to convert the first light emitted from the first light source into second light, wherein the second light is one of parallel light or diverging light;
a second light source configured to emit third light having at least one first wavelength band, wherein the at least one first wavelength band is within the first wavelength range;
a radiation angle adjustment element configured to generate a secondary light source based on adjustment of an angle of the third light emitted from the second light source;
a second collimator optical system configured to convert light corresponding to the secondary light source into fourth light, wherein the fourth light is the one of the parallel light or the diverging light; and
a first light guide configured to guide the second light and the fourth light to a second light guide,
wherein the radiation angle adjustment element is further configured to adjust an emission angle of the third light to reduce a difference between an incident angle of the second light at an incident end surface of the second light guide and an incident angle of the fourth light at the incident end surface of the second light guide.

2. The medical imaging system of claim 1, further comprising the second light guide, wherein the second light and the fourth light are incident at the incident end surface of the second light guide.

3. The medical imaging system of claim 2, further comprising a condenser optical system along an optical axis, wherein
the condenser optical system is configured to condense the second light and the fourth light on the incident end surface of the second light guide, and
the first light and the third light are emitted along the optical axis.

4. The medical imaging system of claim 2, further comprising a lens barrel configured to:
receive the second light and the fourth light from the second light guide; and
radiate the second light and the fourth light to an observation site.

5. The medical imaging system of claim 4, further comprising at least one image sensor, wherein the lens barrel is further configured to direct the second light and the fourth light from the observation site to the at least one image sensor.

6. The medical imaging system of claim 2, further comprising a projection lens configured to radiate the second light and the fourth light to an observation site.

7. The medical imaging system of claim 1, further comprising a processor configured to adjust an intensity of the first light and an intensity of the second light.

8. The medical imaging system of claim 7, wherein
the at least one first wavelength band includes a plurality of second wavelength bands, and
the processor is further configured to adjust the intensity of the second light for each of the plurality of second wavelength bands.

9. The medical imaging system of claim 1, further comprising at least one image sensor configured to obtain an image of an observation site, wherein the image includes fluorescence information of the observation site and white light imaging information of the observation site.

10. The medical imaging system of claim 1, wherein the radiation angle adjustment element includes a diffuser.

11. The medical imaging system of claim 1, wherein the first light guide includes a dichroic mirror or a P/S converter.

12. The medical imaging system of claim 1, wherein the radiation angle adjustment element is further configured to adjust the angle of the second light to reduce a difference between a first beam diameter of the first light at the incident end surface of the first light guide and a second beam diameter of the second light at the incident end surface of the first light guide.

13. A medical imaging system, comprising:
a first light source configured to emit first light having a first wavelength range;
a second light source configured to emit second light having a second wavelength range, wherein the second wavelength range is narrower than the first wavelength range;
a radiation angle adjustment element configured to adjust an angle of the second light to reduce a difference between a first incident angle of the first light at an incident end surface of a first light guide and a second incident angle of the second light at the incident end surface of the first light guide; and
an optical element configured to guide the first light and the second light with adjusted angle to the first light guide.

14. The medical imaging system of claim 13, wherein the second light source includes at least one of a red narrow band light source configured to emit a red narrow band light, a green narrow band light source configured to emit a green narrow band light, or a blue narrow band light source configured to emit a blue narrow band light.

15. The medical imaging system of claim 13, wherein the first light source includes at least one of a white LED, a laser excitation phosphor, a xenon lamp, or a halogen lamp.

16. The medical imaging system of claim 13, wherein the optical element includes at least one of a dichroic mirror, a polarization beam splitter, or a beam splitter.

17. The medical imaging system of claim 13, wherein
the second light source includes a plurality of light sources,
the plurality of light sources is configured to emit a plurality of narrow band lights, and
the radiation angle adjustment element is further configured to adjust radiation angles of the plurality of the narrow band lights to reduce the difference of the radiation angles.

18. The medical imaging system of claim 13, further comprising the first light guide, wherein the first light guide is configured to guide the first light and the second light to a medical observation device.

19. The medical imaging system of claim 18, the medical observation device includes at least one of an endoscope or a microscope.

20. The medical imaging system of claim 13, further comprising:
a medical observation device configured to emit the first light and the second light to an observation site; and
at least one image sensor configured to obtain a light from the observation site.

21. The medical imaging system of claim 13, further comprising
at least one image sensor configured to obtain an image of an observation site, wherein the image includes fluorescence information of the observation site and white light imaging information of the observation site.

22. The medical imaging system of claim 13, the radiation angle adjustment element includes a diffuser.

23. The medical imaging system of claim 13, wherein the second wavelength range corresponds to an excitation wavelength of an object in an observation site.

24. A medical imaging method, comprising:
in a medical imaging system:
emitting, by a first light source, first light having a first wavelength range;
emitting, by a second light source, second light having a second wavelength range, wherein the second wavelength range is narrower than the first wavelength range;
adjusting, by a radiation angle adjustment element, an angle of the second light to reduce a difference between a first incident angle of the first light at an incident end surface of a first light guide and a second incident angle of the second light at the incident end surface of the first light guide; and
guiding, by an optical element, the first light and the second light with adjusted angle to the first light guide.

* * * * *